US010611832B2

(12) United States Patent
Scannon et al.

(10) Patent No.: US 10,611,832 B2
(45) Date of Patent: Apr. 7, 2020

(54) CARDIOVASCULAR RELATED USES OF IL-1β ANTIBODIES AND BINDING FRAGMENTS THEREOF

(71) Applicant: XOMA (US) LLC, Berkeley, CA (US)

(72) Inventors: Patrick J. Scannon, San Francisco, CA (US); Alan M. Solinger, Berkeley, CA (US); Jeffrey D. Feldstein, Livingston, NY (US)

(73) Assignee: XOMA (US) LLC, Berkeley, CA (US)

( * ) Notice: Subject to any disclaimer, the term of this patent is extended or adjusted under 35 U.S.C. 154(b) by 0 days.

(21) Appl. No.: 15/647,203

(22) Filed: Jul. 11, 2017

(65) Prior Publication Data
US 2018/0155420 A1 Jun. 7, 2018

Related U.S. Application Data

(63) Continuation of application No. 12/790,738, filed on May 28, 2010, now abandoned.

(60) Provisional application No. 61/313,001, filed on Mar. 11, 2010, provisional application No. 61/252,571, filed on Oct. 16, 2009, provisional application No. 61/182,679, filed on May 29, 2009.

(51) Int. Cl.
C07K 16/24 (2006.01)
A61K 39/395 (2006.01)
A61P 9/04 (2006.01)
A61K 39/00 (2006.01)

(52) U.S. Cl.
CPC .......... C07K 16/245 (2013.01); A61K 39/395 (2013.01); A61K 2039/505 (2013.01); A61P 9/04 (2018.01)

(58) Field of Classification Search
None
See application file for complete search history.

(56) References Cited

U.S. PATENT DOCUMENTS

| 7,662,772 B2 | 2/2010 | Marchionni et al. |
| 7,988,968 B2 | 8/2011 | Masat et al. |
| 2003/0009145 A1 | 1/2003 | Struijker-Boudier et al. |
| 2004/0106954 A1 | 6/2004 | Whitehurst et al. |
| 2006/0047538 A1 | 3/2006 | Condurso et al. |
| 2006/0171948 A1 | 8/2006 | Weinstein et al. |
| 2007/0004909 A1 | 1/2007 | Johnson et al. |
| 2007/0065439 A1 | 3/2007 | Green et al. |
| 2007/0196379 A1 | 8/2007 | Marchionni et al. |
| 2008/0044414 A1* | 2/2008 | Masat ........... C07K 16/245 424/136.1 |
| 2008/0292640 A1* | 11/2008 | Solinger ........... C07K 16/245 424/158.1 |

FOREIGN PATENT DOCUMENTS

| CN | 101228188 A | 7/2008 |
| CN | 101356286 A | 1/2009 |
| JP | 2009511545 A | 3/2009 |
| TW | 200637873 A | 11/2006 |
| WO | WO 2004100987 A2 | 11/2004 |
| WO | WO 2006081139 A2 | 8/2006 |
| WO | WO 2006084145 A2 | 8/2006 |
| WO | WO 2006084145 A3 | 8/2006 |
| WO | WO 2007002261 A2 | 1/2007 |
| WO | WO 2007002261 A3 | 1/2007 |
| WO | WO 2007042524 A2 | 4/2007 |
| WO | WO 2007061906 A2 | 5/2007 |
| WO | WO 2007061906 A3 | 5/2007 |
| WO | WO 2008077145 A2 | 6/2008 |
| WO | WO 2008077145 A3 | 6/2008 |

OTHER PUBLICATIONS

"Novartis phase III study shows ACZ885 (canakinumab) reduces cardiovascular risk in people who survived a hear attack", https://www.novartis.com/news/media-releases/novartis-phase-iii; Jun. 22, 2017.*
Hwang et al, The Journal of the American College of Cardiology; 2001; vol. 38; pp. 1546-1553.*
Harouki, JACC: Basic to Translational Science; 2017; vol. 2, No. 4; pp. 418-430.*
Ridker et al, The New England Journal of Medicine; 2017; vol. 377; pp. 1119-1131*
Everett et al, (2018; 10.1161/CIRCULATIONAHA.118.038010).*
Guillen et al, American Journal of physiology, 1995; vol. 269, pp. R229-R235.*
Abbate, et al. "Interleukin-1 blockade ameliorates left ventricular remodeling following ST-segment elevation acute myocardial infarction—the VCU-ART pilot study." American College of Cardiology, 2010. Presentation Abstract 1045-278.
Abbate, et al "Anakinra, a recombinant human IL-1 receptor antagonist, inhibits apoptosis in experimental acute myocardial infarction." Circulation. 2008, 117:2670-2683.
Abbate, et al. "Interleukin-1β neutralization ameliorates post-infarction cardiac remodeling in the mouse." American College of Cardiology, 2010. Presentation Abstract 1015-70.
Alten, et al. "The human anti-IL-1 beta monoclonal antibody ACZ885 is effective in joint inflammation models in mice and in a proof-of-concept study in patients with rheumatoid arthritis." Arthritis Research & Therapy. 2008, 10:R67.
Apostolakis, et al. "IL-1 cytokines in cardiovascular disease: diagnostic, prognostic and therapeutic implications." Cardiovasc Hematol Agents Med Chem. 2008, 6(2):150-158.

(Continued)

Primary Examiner — Bridget E Bunner
Assistant Examiner — Fozia Hamud
(74) Attorney, Agent, or Firm — Jones Day

(57) ABSTRACT

Disclosed are methods for the reduction, prevention or treatment of cardiovascular events and/or cardiovascular diseases, including acute cardiovascular disease or chronic cardiovascular disease using anti-IL-1β binding molecules (e.g., IL-1β binding antibodies and fragments thereof). The present disclosure also relates to methods for prevention or treatment of cardiovascular events and/or cardiovascular diseases, including by reducing a cardiovascular event or disease.

48 Claims, 9 Drawing Sheets
Specification includes a Sequence Listing.

(56) References Cited

OTHER PUBLICATIONS

Bhaskar, et al. "XOMA 052, a regulatory monoclonal antibody targeting IL-1β, reduces biomarkers of cardiovascular risk in animal models." Cytokine. 2009; 48(1-2):77-78. Abstract.

Biasucci, "CDC/AHA Workshop on Markers of Inflammation and Cardiovascular Disease: Application to Clinical and Public Health Practice: clinical use of inflammatory markers in patients with cardiovascular diseases: a background paper," Circulation, 110(25):e560-567 (2004).

Blum, et al., "Levels of T-lymphocyte Subpopulations, Interleukin-lb and Soluble Interleukin-2 Receptor in Acute Myocardial Infarction." American Heart Journal 1994, 127(5):1226-1230; table 1; abstract; p. 1228, coil, para 2 to p. 1229. coil, para 1; p. 1230, col. 1, para 3.

Bujak, et al. "Interleukin-1 receptor type I signaling critically regulates infarct healing and cardiac remodeling." Am J Pathol. 2008, 173(1):57-67.

Bujak, et al., "The role of IL-1 in the pathogenesis of heart disease." Arch Immunol Ther Exp. 2009, 57:165-176.

Cacciapaglia et al., "Matters of the heart: the case of TNFalpha-targeting drugs," Mol Interv., 11(2):79-87 (2011).

Calabro, et al, "Release of C-Reactive Protein in Response to Inflammatory Cytokines by Human Adipocytes: Linking Obesity to Vascular Inflammation " Journal of the American College of Cardiology, 2005, vol. 46, No. 6, pp. 1112-1113.

Chamberlain, et al. "IL-1beta and signaling of IL-1 in vascular wall and circulating cells modulates the extent of neointima formation in mice." Am J Pathol. 2006, 168:1396-1403.

Chamberlain, et al. "Interleukin-1 regulates multiple atherogenic mechanisms in response to fat feeding." PLoS ONE. 2009, 4(4):e5073.

Cohen, et al. "A multicentre, double blind, randomized, placebo controlled trial of Anakinra (Kineret), a recombinant interleukin 1 receptor antagonist, in patients with rheumatoid arthritis treated with background methotrexate." Ann Rheum Dis. 2004, 63:1062-1068.

Deckers, "Classification of myocardial infarction and unstable angina. a re-assessment," Int J Cardiol., 167(6):2387-2390 (2013).

DeSouza, et al. "Therapeutic targets to reduce cardiovascular disease in type 2 diabetes." Nature Reviews: Drug Discovery. May 2009, 8:361-367.

D'Ettorre et al., "Functional epitope mapping of human interleukin-1 beta by surface plasmon resonance," Eur Cytokine Netw, 8(2):161-171 (1997).

Dinarello "Biological Basis for Interleukin-1 in Disease." Blood. Mar. 15, 1996, 87(6):2095-2147.

Dinarello "Immunological and inflammatory functions of the interleukin-1 family." Annu Rev Immunol. 2009, 27:519-550.

Djaberi, et al. "Non-invasive cardiac imaging techniques and vascular tools for the assessment of cardiovascular disease in type 2 diabetes mellitus" Diabetolgia (2008) 51:1581-1593.

Duarte, et al. "Overexpression of Interleukin.1β and Interleukin-6 May Play an Important Role in Periodontal Breakdown in Type 2 Diabetic Patients." J Periodont Res. 2007, 42(4):477-481; abstract; p. 377, col. 1, para 1 to col. 3, para 1.

Duewell, et al., "NLRP3 inflammasomes are required for atherogenesis and activated by cholesterol crystals." Nature: Letters; Apr. 29, 2010; 464:1357-1362; MacMillan Publishers Ltd.

Extended European Search Report for EP 10781360.2 (2435073)—dated Feb. 25, 2013; pp. 1-10.

Feldstein, et al. "XOMA 052, a Potential Disease-Modifying Anti-Interleukin-1β (IL-1 beta) Regulatory Antibody, Shows Reductions in hsCRP, HbAlc and FBG After Subcutaneous Injection ina Randomized, Blinded, Placebo-Controlled Trial in Subjects with Type 2 Diabetes Mellitus." International Diabetes Federation (IDF) 20th World Congress 2009, Abstract D-0856:273; XOMA (US) LLC, Berkeley, CA USA.

Gabay, et al. "IL-1 pathways in inflammation and human diseases." Nature Reviews: Rheumatology; Feb. 23, 2010:1-10; MacMillan Publishers Ltd.

Giles, et al. "Diabetes Mellitus and Heart Failure: Basic Mechanisms." Clinical Features, and Therapeutic Considerations. Cardiol Clin. Nov. 2004; 22(4):553-568; p. 553, colt, para 1 to col. 2, para 2; p. 563, col. 1, para 2.

Glynn, et al. "A Randomized Trial of Rosuvastatin in the Prevention of Venous Thromboembolism." N. Engl. J. Med. Apr. 30, 2009; 360:18:1851-1861; Massachusetts Medical Society.

Grundy et al. "Assessment of Cardiovascular Risk by Use of Multiple-Risk-Factor Assessment Equations: A Statement for Healthcare Professionals from the American Heart Association and the American College of Cardiology." J Am Coli Cardiol. vol. 34: 1348-1359, 1999.

Helfand, et al. "Emerging Risk Factors for Coronary Heart Disease: A Summary of Systematic Reviews Conducted for the U.S. Prevention Services Task Force." Oct. 6, 2009; Annals of Int. Med; 151(7):496-507- and W-162-164.

Hoffman et al. "Efficacy and safety of rilonacept (Interleukin-1 Trap) in patients with cryopyrin-associated periodic syndromes." Arthritis & Rheumatism. 2008, 58(8):2443-2452.

Hwang et al. "Neutralization of interleukin-1β in the acute phase of myocardial infarction promotes the progression of left ventricular remodeling", J. of the Amer. College of Cardiology, Nov. 1, 2001, 5(38):1546-1553.

Ikonomidis, et al. "Chronic inhibition of interleukin-1 activity by anakinra is more effective than corticosteroids in improving endothelial function and coronary flow reserve." Circulation. 2008, 118(18, Suppl. 2):S367.

Ikonomidis, et al "Inhibition of IL-1 by anakinra improves vascular and left ventricular function in patients with rheumatoid arthritis." Circulation. 2008, 117:2662-2669.

International Preliminary Report on Patentability (IPRP) for PCT/US2010/036761—dated Nov. 29, 2011; pp. 1-14.

International Search Report for PCT/US2010/036761—dated Sep. 7, 2010; pp. 1-3.

Isoda, et al. "Deficiency of interleukin-1 receptor antagonist promotes neointimal formation after injury." Circulation. 2003, 108:516-518.

Isoda, et al. "Lack of interleukin-1 receptor antagonist modulates plaque composition in apolipoprotein E-deficient mice." Arterioscler Thromb Vasc Biol. 2004, 24(6):1068-1073.

Kastrati, et al. "Protective role against restenosis from an interleukin-1 receptor antagonist gene polymorphism in patients treated with coronary stenting." J Am Coll Cardiol. 2000, 36:2168-2173.

Kavsak, et al. "Elevated C-reactive protein in Acute Coronary Syndrome Presentation is an Independent Predictor of Long-Term Mortality and Heart Failure." Clinical Biochem. 2007, 40(56):326-329; abstract; p. 328, col. 2, para 2; p. 329, coil, para 4.

Kirii, et al."Lack of interleukin-1beta decreases the severity of atherosclerosis in ApoE-deficient mice." Arterioscler Thromb Vasc Biol. 2003, 23:656-660.

Kramer, et al. "Interleukin•1β Stimulates Acute Phase Response and C-Reactive Protein and Synthesis by Inducing an NFB- and C/EB-Dependent Autocrine Interleukin-6 Loop." Molecular Immunology 2008, 45(9):2678-2689; Fig 6; abstract; p. 2686, col. 1 para 2; p. 2688, col. 1, para 2.

Kusukara, et al., "Interleukin-1 and occlusive arterial diseases." Cardiovasc Hematol Agents Med Chem. 2006, 4(3):229-235.

Lachmann, et al. "Use of canakinumab in the cryopyrin-associated periodic syndrome." N Engl J Med. 2009, 360(23):2416-2425.

Lachmann, et al., "In vivo regulation of interleukin 1β in patients with cryopyrin-associated periodic syndromes." J Exp Med. 2009, 206(5):1029-1036.

Lane et al., "Infusion of pharmaceutical-grade natural human C-reactive protein is not proinflammatory in healthy adult human volunteers," Circ Res., 114(4):672-676 (2014) (Epub Dec. 12, 2013).

Larsen, et al. "Interleukin-1-Receptor Antagonist in Type 2 Diabetes Mellitus." N.Engl. J Med. Apr. 12, 2007, 356(15);1517-1526.

Marculescu, et al. "Interleukin-1 Receptor Antagonist Genotype is Associated with Coronary Atherosclerosis in Patients with Type 2 Diabetes." Diabetes; Dec 2002; 51:3582-3585.

May, et al. "Homocysteine Levels are Associated with Increased Risk of Congestive Heart Failure in Patients with and without

(56) References Cited

OTHER PUBLICATIONS

Coronary Artery Disease." Cardiology 2007; 107:178-184. abstract; p. 183, col. 1, para 2 to col. 2, para 1; S. Karger AG.

Mei, et al. "Study on the Relationship of Apache III and Levels of Cytokines in Patients with Systemic Inflammatory Response Syndrome after Coronary Artery Bypass Grafting." Bioi. Pharm. Bull. 2007, 30(3):410-414; abstract; p. 413, col. 1, para 1 to col. 2, para 2.

Merhi-Soussi, et al. "Interleukin-1 Plays a Major Role in Vascular Inflammation and Atherosclerosis in Male Apolipoprotein E-knockout Mice." Cardiovasc Res.; Jan. 2005, 66:583-593.

Mizushima, et al. "Reduced Postischemic Apoptosis in the Hippocampus of Mice Deficient in lnterleukin-1." The J. of Comparative Neurology; May 2002, 448(2):203-216; abstract; p. 207, col. 1, para 2.

Morton, et al. "Interleukin-1 Receptor Antagonist Alters the Response to Vessel Wall Injury in a Porcine Coronary Artery Model." Cardiovasc Res.; 2005, 68:493-501.

Muniyappa, et al. "Cardiovascular Actions of Insulin." Endocrine Reviews; Aug. 2007; 28(5):463-491.

Murtuza, et al. "Transplantation of Skeletal Myoblasts Secreting an IL-1 Inhibitor Modulates Adverse Remodeling in Infarcted Murine Myocardium." PNAS; Mar. 23, 2004, 101(12):4216-4221.

Nabata, et al. "C-reactive protein induces endothelial cell apoptosis and matrix metalloproteinase-9 production in human mononuclear cells: Implications for the destabilization of atherosclerotic plaque." Atherosclerosis; Jan. 2008; 196(1):129-135.

Nicklin, et al. "Arterial Inflammation in Mice Lacking the Interleukin 1 Receptor Antagonist Gene." J. Exp Med.; Jan. 17, 2000; 191(2):303-312; The Rockefeller University Press.

Osherovich, L. "Athero-Inflammation Link Crystallizes. " SciBX: Science-Business eXchange; 2010; p. 1-2.

Ozeran, et al. "Levels of Serum IL-1β, IL-2, IL-8 and Tumor Necrosis Factor-α in Patients with Unstable Angina Pectoris." Mediators of Inflammation 2003, 12(6):361-365; Table 2; abstract; p. 363, col. 1, para 2-3.

Persson, et al. "Interleukin-1beta and Tumour Necrosis Factor-Alpha Impede Neutral Lipid Turnover in Macrophage-Derived Foam Cells." BioMedCentral (BMC) Immunology 2008; 9(70)129.

Picco, et al. "Successful Treatment of Idiopathic Recurrent Pericarditis in Children with Interleukin-1 Receptor Antagonist (Anakinra). " Arthritis & Rheumatism. 2009, 60(1):264-268.

Prabhu, et al. "Cytokine-Induced Modulation of Cardiac Function." Circ. Res. 2004; 95; 1140-1153.

Recienwald, et al. "Direct Evidence for Cytokine Involvement in Neointimal Hyperplasia." Cicrulation. 2000; 102; 1697-1702.

Roifman et al., "Chronic inflammatory diseases and cardiovascular risk: a systematic review,"Can J Cardiol., 27(2):174-182 (2011).

Salloum, et al "Anakinra in Experimental Acute Myocardial Infarction—Does Dosage or Duration of Treatment Matter?" Cardiovasc Drugs Ther. Nov. 2009, 23:129-135. Springer Science.

Sattar, et al. "Are Markers of Inflammation More Strongly Associated with Risk for Fatal Than for Nonfatal Vascular Events?" PLoS Medicine; Jun. 2009; 6(6):1-10.

Schlager, et al. "C-Reactive Protein Predicts Future Cardiovascular Events in Patients with Carotid Stenosis." Stroke: J. of the Amer. Heart Assoc.; Feb. 22, 2007; 38:1263-1268.

Simon, et al. "Circulating Levels of IL-1β, a Prothrombotic Cytokine, are Elevated in Unstable Angina Versus Stable Angina." J. of Thrombosis and Thrombolysis, 2000, 9:217-222.

Sims, et al. "The IL-1 Family: Regulators of Immunity." Nature Reviews: Immunology; AOP; Jan. 18, 2010; 1-14.

Song, et al."Pretreatment with Aspirin for Protection against Heat Stroke in Rats." J. First Mil Med Univ.; 2004, 24(6):631-635; Abstract in English.

Sun, et al. "Inflammation of Different Tissues in Spontaneously Hypertensive Rats." Acta Physiologica Sinica 2006, 58(4):318-323; Abstract in English.

Suzuki, et al. "Overexpression of Interleukin-1 Receptor Antagonist Provides Cardioprotection Against Ischemia-Reperfusion Injury Associated with Reduction in Apoptosis." Circulation: J. of the Amer. Heart Assoc.; 2001; 104; I-308 to I-313.

Toldo et al., "Interleukin-1 Blockade in Acute Myocardial Infarction and Heart Failure: Ready for Clinical Translation?" Translational Medicine, 3(1):1000e114 (5 pages) (2013).

Van Tassell, et al. "Interleukin-1 Trap Attenuates Cardiac Remodeling After Experimental Acute Myocardial Infarction in Mice." J. Cardiovasc Pharmacol; Feb. 2010; 55(2):117-122.

Vicenova, et al. "Emerging Role of Interleukin-1 in Cardiovascular Diseases." Physiol. Res.; 2009; 58:48-498.

Wang, et al. "Expression of Interleukin-1β, Interleukin-1 Receptor, and Interleukin-1 Receptor Antagonist mRNA in Rat Carotid Artery after Balloon Angioplasty." Biochem Biophys Res Commun.; 2000, 271:138-143.

Bhaskar, et al. 2009, "XOMA 052, a regulatory monoclonal antibody targeting IL-1β, reduces biomarkers of cardiovascular risk in animal models," TriSociety Poster; XOMA (US) LLC, Berkeley, CA USA.

Griselli et al., 1999, "C-reactive protein and complement are important mediators of tissue damage in acute myocardial infarction," J Exp Med., 190(12):1733-1740.

Ridker, 2003, "Clinical application of C-reactive protein for cardiovascular disease detection and prevention," Circulation, 107(3):363-369.

Shimokawa et al., 1996, "Chronic treatment with interleukin-1 beta induces coronary intimal lesions and vasospastic responses in pigs in vivo. The role of platelet-derived growth factor," J Clin Invest., 97(3):769-776.

* cited by examiner $T_\alpha$ = 1.6 days
$T_\beta$ = 22.7 days
CL = 2.4 mL/day/kg
$V_c$ = 40.7 mL/kg
$F_{alpha}$ = 0.068

LOQ = Limit of Quantification

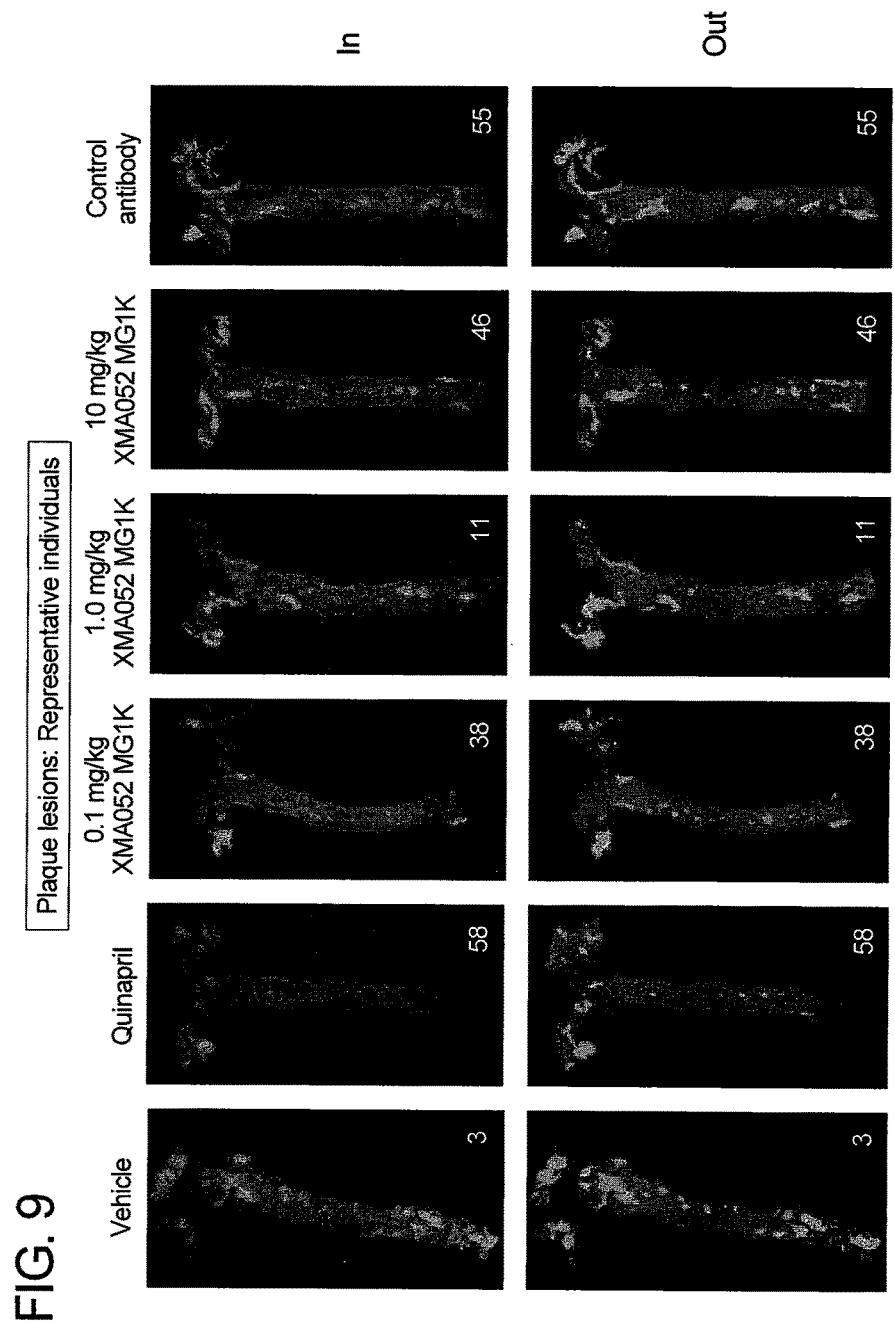

SEQUENCE LISTING

```
<160> NUMBER OF SEQ ID NOS: 5

<210> SEQ ID NO 1
<211> LENGTH: 107
<212> TYPE: PRT
<213> ORGANISM: Artificial
<220> FEATURE:
<223> OTHER INFORMATION: Synthesized: AB7 light chain

<400> SEQUENCE: 1

Asp Ile Gln Met Thr Gln Ser Thr Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Lys Ala Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Gln
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys
            100                 105

<210> SEQ ID NO 2
<211> LENGTH: 120
<212> TYPE: PRT
<213> ORGANISM: Artificial
```

```
<220> FEATURE:
<223> OTHER INFORMATION: Synthesized: AB7 heavy chain

<400> SEQUENCE: 2

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 3
<211> LENGTH: 23
<212> TYPE: PRT
<213> ORGANISM: Artificial
<220> FEATURE:
<223> OTHER INFORMATION: Synthesized: Epitope corresponding to residues
      83-105 of the mature IL-1 protein

<400> SEQUENCE: 3

Glu Ser Val Asp Pro Lys Asn Tyr Pro Lys Lys Lys Met Glu Lys Arg
1               5                   10                  15

Phe Val Phe Asn Lys Ile Glu
            20

<210> SEQ ID NO 4
<211> LENGTH: 107
<212> TYPE: PRT
<213> ORGANISM: Artificial
<220> FEATURE:
<223> OTHER INFORMATION: Synthesized: AB5 light chain

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Leu Gln Gly Lys Met Leu Pro Trp
                85                  90                  95

Thr Phe Gly Gly Gly Thr Lys Leu Glu Ile Lys
            100                 105

<210> SEQ ID NO 5
```

```
<211> LENGTH: 120
<212> TYPE: PRT
<213> ORGANISM: Artificial
<220> FEATURE:
<223> OTHER INFORMATION: Synthesized: AB5 heavy chain

<400> SEQUENCE: 5

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
            115                 120
```

CARDIOVASCULAR RELATED USES OF IL-1β ANTIBODIES AND BINDING FRAGMENTS THEREOF

RELATED APPLICATIONS

This application is a continuation of U.S. application Ser. No. 12/790,738, filed May 28, 2010, which claims the benefit of U.S. Provisional Application No. 61/313,001, filed Mar. 11, 2010, U.S. Provisional Application No. 61/252,571 filed Oct. 16, 2009, and U.S. Provisional Application No. 61/182,679 filed May 29, 2009, the disclosures of which are herein incorporated by reference herein in their entirety.

FIELD OF INVENTION

The present disclosure relates generally to IL-1β binding molecules (e.g., IL-1β binding antibodies and fragments thereof) for the reduction, prevention or treatment of cardiovascular events and/or cardiovascular diseases (e.g., acute cardiovascular disease or chronic cardiovascular disease).

BACKGROUND OF THE INVENTION

Inflammation has become a central theme in the pathogenesis of cardiovascular disease over the past decade, and a wide range of cardiac diseases has been associated with inflammation and cytokine modulation (Mehra et al., 2005, J. Leukocyte Biol. 78:805-818). Proinflammatory cytokines may be secreted by every nucleated cell type in the myocardium, including the cardiac myocyte, in response to various forms of stress/injury. They are elevated in conditions as diverse as inflammatory myocarditis, allograft rejection, cardiac ischemic states, congestive heart failure (CHF), and reperfusion injury.

IL-1β is a pro-inflammatory cytokine secreted by a number of different cell types including monocytes and macrophages. When released as part of an inflammatory reaction, IL-1β produces a range of biological effects, mainly mediated through induction of other inflammatory mediators such as corticotrophin, platelet factor-4, prostaglandin E2 (PGE2), IL-6, and IL-8. IL-1β induces both local and systemic inflammatory effects through the activation of the IL-1 receptor found on almost all cell types. The interleukin-1 (IL-1) family of cytokines has been implicated in a number of disease states. IL-1 family members include IL-1α, IL-1β, and IL-1Ra. Although related by their ability to bind to IL-1 receptors (IL-1R1 and IL-1R2), each of these cytokines is different, being expressed by a different gene and having a different primary amino acid sequence. Furthermore, the physiological activities of these cytokines can be distinguished from each other.

SUMMARY OF THE INVENTION

The present disclosure relates generally to IL-1β binding molecules (e.g., IL-1β binding antibodies and fragments thereof) for the reduction, prevention or treatment of cardiovascular events and/or cardiovascular diseases, including acute cardiovascular disease or chronic cardiovascular disease. The present disclosure also relates to methods for prevention or treatment of cardiovascular events and/or cardiovascular diseases, including by reducing a cardiovascular event or disease.

The present disclosure provides methods of reducing a cardiovascular event in a subject, comprising administering to said subject a therapeutically effective amount of an anti-IL-1β binding antibody or binding fragment thereof, wherein the subject is a subject with a history of a previous cardiovascular event or a history of at least one risk factor for cardiovascular disease, and wherein the cardiovascular event is myocardial infarction, stroke, cardiovascular death, congestive heart failure, cardiac arrest, acute coronary syndrome, angina, or a revascularization procedure.

The present disclosure provides methods of reducing a cardiovascular event (e.g., delaying time to event, reducing likelihood or risk of event, preventing an event, reducing severity of event, reducing time to recovery) in a subject with a history of at least one risk factor for cardiovascular disease, comprising administering to said subject a therapeutically effective amount of an anti-IL-1β binding antibody or binding fragment thereof, and wherein the cardiovascular event is myocardial infarction, stroke, cardiovascular death, congestive heart failure, cardiac arrest, acute coronary syndrome, angina, or a revascularization procedure.

The present disclosure also provides methods of reducing a cardiovascular event (e.g., delaying time to event, reducing likelihood or risk of event, preventing an event, reducing severity of event, reducing time to recovery) in a subject with a history of a previous cardiovascular event, comprising administering to said subject a therapeutically effective amount of an anti-IL-1β binding antibody or binding fragment thereof, and wherein said cardiovascular event is myocardial infarction, stroke, cardiovascular death, congestive heart failure, cardiac arrest, acute coronary syndrome, angina or a revascularization procedure. In some embodiments, the previous cardiovascular event is a first cardiovascular event. In some embodiments, the previous or first cardiovascular event is selected from the group consisting of myocardial infarction, stroke, congestive heart failure, acute coronary syndrome, angina and a revascularization procedure. In some embodiments, the previous or first cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG). In some embodiments, the method of reducing a cardiovascular event is a method of reducing a second or subsequent cardiovascular event. In some embodiments, the cardiovascular event (e.g., second or subsequent cardiovascular event) is selected from the group consisting of myocardial infarction, stroke, cardiovascular death, congestive heart failure, cardiac arrest, acute coronary syndrome, angina and a revascularization procedure. In some embodiments, the first cardiovascular event and second cardiovascular event are the same types of cardiovascular events. In some embodiments, the first cardiovascular event and second cardiovascular event are different types of cardiovascular events.

In some embodiments, the revascularization procedure is a coronary, carotid or peripheral arterial revascularization procedure. In some embodiments, the coronary, carotid or peripheral arterial revascularization procedure is a percutaneous coronary intervention (PCI), a stent implant, coronary artery bypass graft (CABG), carotid endarterectomy, peripheral vascular disease bypass surgery, or peripheral angioplasty surgery.

In some embodiments, said subject also has a history of at least one risk factor for cardiovascular disease. In some embodiments, the risk factor is manifest coronary heart disease, coronary artery disease, thrombosis, transient ischaemic attack, left ventricular hypertrophy, arteriosclerosis, restenosis, tobacco smoking or peripheral vascular disease. In some embodiments, the risk factor is elevated triglycerides, systemic inflammation, high blood phosphorus levels, high parathyroid hormone levels, microalbuminuria, or high homocysteine levels. In some embodiments, the risk factor is obesity, hyperglycemia, chronic renal failure, high blood glucose, chronic kidney disease, or metabolic syndrome. In some embodiments, the risk factor is end stage renal disease. In some embodiments, the risk factor is hypertension, dyslipidemia, hyperlipidemia, elevated total cholesterol, elevated LDL cholesterol, or low HDL cholesterol or atherosclerosis. In some embodiments, the hypertension is manifested as a blood pressure of greater than or equal to 180/110 mm Hg. In some other embodiments, the hypertension is mild-to-moderate, with systolic blood pressure (SBP) of 140 to 180 mm Hg and/or diastolic blood pressure (DBP) of 90 to 110 mm Hg.

In some embodiments, the subject has elevated levels of C-reactive protein (CRP).

In some embodiments, the subject is older than 55 years.

In some embodiments, the subject is older than 65 years.

In some embodiments, the subject is non-hypertensive.

In some embodiments, the subject has poorly controlled hypertension.

In some embodiments, the subject has an arrhythmia.

In some embodiments, the subject has a "Type A" personality.

In some embodiments, the subject has a sedentary lifestyle.

In some embodiments, the subject has diabetes mellitus. In some embodiments, said diabetes mellitus is Type 2 diabetes.

In some embodiments, the subject has a history of two or more said risk factors.

In some embodiments, the subject has a history of three or more said risk factors.

In some embodiments, administering said therapeutically effective amount of an anti-IL-1β binding antibody or binding fragment thereof is sufficient to achieve a decrease in CRP levels.

The present disclosure also provides methods of reducing mortality following a cardiovascular event in a subject, comprising administering to said subject a therapeutically effective amount of an anti-IL-1β binding antibody or binding fragment thereof.

In some embodiments, the cardiovascular event is myocardial infarction, stroke, congestive heart failure, acute coronary syndrome, angina or a revascularization procedure. In some embodiments, the cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG). In some embodiments, the revascularization procedure is a coronary, carotid or peripheral arterial revascularization procedure. In some embodiments, the coronary, carotid or peripheral arterial revascularization procedure is a percutaneous coronary intervention (PCI), a stent implant, coronary artery bypass graft (CABG), carotid endarterectomy, peripheral vascular disease bypass surgery, or peripheral angioplasty surgery.

In some embodiments, the subject does not have Type 2 diabetes.

In some embodiments, the subject has survived a previous cardiovascular event of myocardial infarction or stroke.

In some embodiments, the occurrence of said cardiovascular event is a reoccurrence of a cardiovascular event of myocardial infarction or stroke.

In some embodiments, the subject has a history of one or more risk factors for cardiovascular disease. In some embodiments, the risk factor is manifest coronary heart disease, coronary artery disease, thrombosis, transient ischaemic attack, left ventricular hypertrophy, arteriosclerosis, restenosis, tobacco smoking or peripheral vascular disease. In some embodiments, the risk factor is elevated triglycerides, systemic inflammation, high blood phosphorus levels, high parathyroid hormone levels, microalbuminuria, or high homocysteine levels. In some embodiments, the risk factor is obesity, hyperglycemia, chronic renal failure, high blood glucose, chronic kidney disease, or metabolic syndrome. In some embodiments, the risk factor is end stage renal disease. In some embodiments, the risk factor is hypertension, dyslipidemia, hyperlipidemia, elevated total cholesterol, elevated LDL cholesterol, or low HDL cholesterol or atherosclerosis. In some embodiments, the hypertension is manifested as a blood pressure of greater than or equal to 180/110 mm Hg. In some other embodiments, the hypertension is mild-to-moderate, with systolic blood pressure (SBP) of 140 to 180 mm Hg and/or diastolic blood pressure (DBP) of 90 to 110 mm Hg.

In some embodiments, the subject is non-hypertensive.

In some embodiments, the subject has poorly controlled hypertension.

In some embodiments, the subject has an arrhythmia.

In some embodiments, the subject has a "Type A" personality.

In some embodiments, the subject has a sedentary lifestyle.

In some embodiments, the subject has a history of two or more said risk factors.

In some embodiments, the subject has a history of three or more said risk factors.

In some embodiments, the subject is a patient with cardiovascular disease, including acute cardiovascular disease (e.g., not associated with congestive heart failure) or chronic cardiovascular disease (e.g., associated with multiple risk factors for atherosclerotic cardiovascular disease).

In some embodiments, administering said therapeutically effective amount of an anti-IL-1β binding antibody or binding fragment thereof is sufficient to achieve a decrease in CRP levels.

The present disclosure also provides methods of reducing a cardiovascular event in a subject with a history of at least one risk factor for cardiovascular disease, comprising administering to said subject a therapeutically effective amount of an anti-IL-1β binding antibody or binding fragment thereof, and wherein said risk factor is not Type 2 diabetes, obesity, hyperglycemia, dyslipidemia, hyperlipidemia, chronic renal failure, high blood glucose, chronic kidney disease, hypertension, atherosclerosis or metabolic syndrome.

In some embodiments, the cardiovascular event is myocardial infarction, stroke, cardiac arrest, congestive heart failure, cardiovascular death, acute coronary syndrome (e.g., diagnosed), angina or a revascularization procedure. In some embodiments, the revascularization procedure is a coronary, carotid or peripheral arterial revascularization procedure. In some embodiments, the coronary, carotid or peripheral arterial revascularization procedure is a percutaneous coronary intervention (PCI), a stent implant, coronary artery bypass graft (CABG), carotid endarterectomy, peripheral vascular disease bypass surgery, or peripheral angioplasty surgery.

In some embodiments, the risk factor is manifest coronary heart disease, coronary artery disease, thrombosis, transient ischaemic attack, left ventricular hypertrophy, arteriosclerosis, restenosis, tobacco smoking or peripheral vascular disease. In some embodiments, the risk factor is elevated triglycerides, systemic inflammation, high blood phosphorus levels, high parathyroid hormone levels, microalbuminuria, or high homocysteine levels.

In some embodiments, the subject has elevated levels of C-reactive protein (CRP).

In some embodiments, the subject is older than 55 years.

In some embodiments, the subject is older than 65 years.

In some embodiments, the subject has a history of two or more said risk factors.

In some embodiments, the subject has a history of three or more said risk factors.

In some embodiments, the subject is a patient with cardiovascular disease, including acute cardiovascular disease (e.g., not associated with congestive heart failure) or chronic cardiovascular disease (e.g., associated with multiple risk factors for atherosclerotic cardiovascular disease).

In some embodiments, administering said therapeutically effective amount of an anti-IL-1β binding antibody or binding fragment thereof is sufficient to achieve a decrease in CRP levels.

The present disclosure also provides methods of treating a cardiovascular event in a subject, wherein the cardiovascular event is myocardial infarction, stroke, congestive heart failure, acute coronary syndrome or angina, comprising administering to said subject a therapeutically effective amount of an anti-IL-1β binding antibody or binding fragment thereof and at least one other pharmaceutical composition comprising an active agent other than an IL-1β antibody or fragment.

In some embodiments, the cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG).

In some embodiments, the active agent of said at least one other pharmaceutical composition is a cholesterol lowering agent, a statin, an HMG-CoA reductase inhibitor, a calcium channel blocker, a beta blocker, an antihypertensive, a diuretic, aspirin, niacin, an angiotensin-converting enzyme (ACE) inhibitor, an angiotensin II receptor blocker, a vasodilator, an anticoagulant, a inhibitor of platelet aggregation, a thrombolytic or digitalis.

The present disclosure also provides methods of treating a cardiovascular event in a subject, wherein the cardiovascular event is myocardial infarction, stroke, congestive heart failure, acute coronary syndrome or angina, comprising administering to said subject a therapeutically effective amount of an anti-IL-1β binding antibody or binding fragment thereof and (e.g., in conjunction with) a revascularization procedure.

In some embodiments, the cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG).

In some embodiments, the revascularization procedure is a coronary, carotid or peripheral arterial revascularization procedure.

The present disclosure also provides methods of treating cardiovascular disease, including, for example, acute cardiovascular disease or chronic cardiovascular disease, in a subject, comprising administering to said subject a therapeutically effective amount of an anti-IL-1β binding antibody or binding fragment thereof and (e.g., in conjunction with) a revascularization procedure.

In some embodiments, administering said therapeutically effective amount of an anti-IL-1β binding antibody or binding fragment thereof is sufficient to achieve a reduction in the relative risk (e.g., lower risk, frequency, incidence, severity) of MACE (major adverse cardiac event, e.g., myocardial infarction, stroke, death, such as CV death, and/or composite thereof), including, for example, in patients with cardiovascular disease, such as acute cardiovascular disease or chronic cardiovascular disease, or in patients with multiple risk factors for atherosclerotic cardiovascular disease (e.g., age 55, age 65, plus one or more of: CABG, NSTEMI, hypertension, elevated cholesterol or on statins, elevated CRP, prior history of Myocardial infarction/stroke no less than 6 months, prior history of ACS or TIA, smoking, history of PCI, type 2 diabetes).

In some embodiments, administering said therapeutically effective amount of an anti-IL-1β binding antibody or binding fragment thereof is sufficient to achieve an in time to first MACE event, revascularization procedures (e.g., CABG), all cause mortality, peripheral vascular disease, first documented angina endpoint, hospitalization for congestive heart failure (CHF), decrease in number of hospital visits, duration of hospital stay, rehospitalization for ischemic events (e.g., angina and/or CHF), infarct size, diastolic volume, ejection fraction or use of diuretics.

In some embodiments, administering said therapeutically effective amount of an anti-IL-1β binding antibody or binding fragment thereof is sufficient to achieve plaque regression, plaque stabilization and/or inhibition of plaque rupture.

In some embodiments, administering said therapeutically effective amount of an anti-IL-1β binding antibody or binding fragment thereof is sufficient to achieve a decrease in CRP levels, BNP levels, troponin levels, C-peptide levels, LDL levels, blood pressure or blood sugar (HbA1c).

In some embodiments, administering said therapeutically effective amount of an anti-IL-1β binding antibody or binding fragment thereof is sufficient to achieve a decrease or no increase in SAE, malignancy, hypoglycemia, serious infection rate, infection rate, immunogenicity or heart failure.

The present disclosure also provides methods of reducing restenosis in a subject following a revascularization procedure, comprising administering to said subject a therapeutically effective amount of an anti-IL-1β binding antibody or binding fragment thereof.

In some embodiments, the revascularization procedure is a coronary, carotid or peripheral arterial revascularization procedure.

In some embodiments, administering said therapeutically effective amount of an anti-IL-1β binding antibody or binding fragment thereof is sufficient to achieve a decrease in CRP levels.

The present disclosure also provides methods of treating acute hypertension in a subject comprising administering to said subject a therapeutically effective amount of an anti-IL-1β binding antibody or binding fragment thereof and one or more antihypertensive agents. In some embodiments, the subject has a blood pressure of greater than or equal to 180/110 mm Hg. In some other embodiments, the subject has mild-to-moderate hypertension, with systolic blood pressure (SBP) of 140 to 180 mm Hg and/or diastolic blood pressure (DBP) of 90 to 110 mm Hg. In some embodiments, the antihypertensive agent is administered intravenously. In some embodiments, the antihypertensive agent is selected from the group consisting of alpha/beta-adrenergic blocking agents, angiotensin-converting enzyme inhibitors, angiotensin II receptor antagonists, antiadrenergic agents, beta-adrenergic blocking agents, calcium-channel blocking agents, diuretics, and vasodilators. In some embodiments, the antihypertensive agent is carvedilol, labetalol, benazepril, captopril, enalapril, fosinopril, lisinopril, moexipril, perindopril, quinapril, ramipril, trandolapril, candesartan, eprosartan, irbesartan, losartan, telmisartan, valsartan, clonidine, doxazosin, guanabenz, guanadrel, guanethidine, guanfacine, mecamylamine, methyldopa, prazosin, reserpine, terazosin, acebutolol, atenolol, betaxolol, bisoprolol, carteolol, metoprolol, nadolol, penbutolol, pindolol, propranolol, timolol, amlodipine, diltiazem, felodipine, isradipine, nicardipine, nifedipine, nisoldipine, verapamil, amiloride, benzthiazide, chlorothiazide, chlorthalidone, furosemide, hydrochlorothiazide, indapamide, metolazone, polythiazide, spironolactone, torsemide, trichlormethiazide, hydralazine, nitroglycerin, sodium nitroprusside, clevidipine or minoxidil. In some embodiments, the antihypertensive agent is labetalol, metoprolol, hydralazine, nitroglycerin, nicardipine, sodium nitroprusside or clevidipine.

The present disclosure also provides methods of reducing, preventing or treating a cardiovascular event or disease (e.g., acute cardiovascular disease or chronic cardiovascular disease) in a subject comprising administering to the subject an anti-IL-1β binding antibody or binding fragment thereof in combination with (e.g., in conjunction with) (e.g., before, during or after) a medical or surgical intervention. Such antibodies may be administered in therapeutically effective amounts. Such interventions may be therapeutically effective. In some embodiments, a medical intervention is an active agent, such as a drug or a biologic, including, for example, any one or more of the active agents described herein. In some embodiments, a medical intervention is an out-patient medical treatment or procedure. In some embodiments, a medical intervention is an in-patient hospitalization. In some embodiments, a surgical intervention is a revascularization procedure, including, for example, any one or more of the revascularization procedures described herein. In some embodiments, a surgical intervention involves a heart valve repair or replacement, coronary bypass surgery, heart transplant or heart pump. In some embodiments, a surgical intervention involves a biventricular cardiac pacemaker, internal cardiac defibrillator (ICD) or myectomy. In some embodiments, a medical intervention is smoking cessation medication or smoking cessation counseling.

The present disclosure also provides methods of reducing a cardiovascular event in a subject with a history of at least one risk factor for cardiovascular disease, comprising (a) identifying, diagnosing or selecting the subject with the history of at least one risk factor for cardiovascular disease and (b) administering to the subject a therapeutically effective amount of an anti-IL-1β binding antibody or binding fragment thereof, and wherein the cardiovascular event is myocardial infarction, stroke, cardiovascular death, congestive heart failure, cardiac arrest, acute coronary syndrome, angina, or a revascularization procedure.

The present disclosure also provides methods of reducing a cardiovascular event in a subject with a history of a previous cardiovascular event, comprising (a) identifying, diagnosing or selecting the subject with the history of the previous cardiovascular event and (b) administering to the subject a therapeutically effective amount of an anti-IL-1β binding antibody or binding fragment thereof, and wherein the cardiovascular event is myocardial infarction, stroke, acute coronary syndrome, angina or a revascularization procedure. In some embodiments, the previous cardiovascular event is a first cardiovascular event. In some embodiments, the previous or first cardiovascular event is selected from the group consisting of myocardial infarction, stroke, congestive heart failure, acute coronary syndrome, angina and a revascularization procedure. In some embodiments, the previous or first cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG). In some embodiments, the method of reducing a cardiovascular event is a method of reducing a second or subsequent cardiovascular event. In some embodiments, the cardiovascular event (e.g., second or subsequent cardiovascular event) is selected from the group consisting of myocardial infarction, stroke, cardiovascular death, congestive heart failure, cardiac arrest, acute coronary syndrome, angina and a revascularization procedure. In some embodiments, the first cardiovascular event and second cardiovascular event are the same types of cardiovascular events. In some embodiments, the first cardiovascular event and second cardiovascular event are different types of cardiovascular events.

The present disclosure also provides methods of reducing mortality following a cardiovascular event in a subject, comprising (a) identifying, diagnosing or selecting the subject having the cardiovascular event and (b) administering to the subject a therapeutically effective amount of an anti-IL-1β binding antibody or binding fragment thereof. In some embodiments, the cardiovascular event is selected from the group consisting of myocardial infarction, stroke, congestive heart failure, acute coronary syndrome, angina and a revascularization procedure. In some embodiments, the cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG).

The present disclosure also provides methods of reducing a cardiovascular event in a subject with a history of at least one risk factor for cardiovascular disease, comprising (a)

identifying, diagnosing or selecting the subject with the history of at least one risk factor for cardiovascular disease and (b) administering to the subject a therapeutically effective amount of an anti-IL-1β binding antibody or binding fragment thereof, and wherein the risk factor is not Type 2 diabetes, obesity, hyperglycemia, dyslipidemia, hyperlipidemia, chronic renal failure, high blood glucose, chronic kidney disease, hypertension, atherosclerosis or metabolic syndrome. In some embodiments, the cardiovascular event is selected from the group consisting of myocardial infarction, stroke, cardiovascular death, congestive heart failure, cardiac arrest, acute coronary syndrome, angina and a revascularization procedure.

The present disclosure also provides methods of treating a cardiovascular event in a subject, wherein the cardiovascular event is myocardial infarction, stroke, congestive heart failure, acute coronary syndrome or angina, comprising (a) identifying, diagnosing or selecting the subject with the cardiovascular event and (b) administering to the subject a therapeutically effective amount of an anti-IL-1β binding antibody or binding fragment thereof and at least one other pharmaceutical composition comprising an active agent other than an IL-1β antibody or fragment. In some embodiments, the previous or first cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG).

The present disclosure also provides methods for treating a cardiovascular event in a subject, wherein the cardiovascular event is myocardial infarction, stroke, congestive heart failure, acute coronary syndrome or angina, comprising (a) identifying, diagnosing or selecting the subject with the cardiovascular event and (b) administering to the subject a therapeutically effective amount of an anti-IL-1β binding antibody or binding fragment thereof and (e.g., in conjunction with) a revascularization procedure. In some embodiments, the previous or first cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG).

The present disclosure also provides methods of reducing restenosis in a subject following a revascularization procedure, comprising (a) identifying, diagnosing or selecting the subject with the revascularization procedure and (b) administering to the subject a therapeutically effective amount of an anti-IL-1β binding antibody or binding fragment thereof.

The present disclosure also provides methods of treating acute hypertension in a subject comprising (a) identifying, diagnosing or selecting the subject with acute hypertension and (b) administering to the subject a therapeutically effective amount of an anti-IL-1β binding antibody or binding fragment thereof and one or more antihypertensive agents. In some embodiments, the hypertension is manifested as a blood pressure of greater than or equal to 180/110 mm Hg. In some other embodiments, the hypertension is mild-to-moderate, with systolic blood pressure (SBP) of 140 to180 mm Hg and/or diastolic blood pressure (DBP) of 90 to 110 mm Hg.

In any and/or all of the aforementioned embodiments, administering said therapeutically effective amount of an anti-IL-1β binding antibody or binding fragment thereof may be sufficient to achieve a decrease in CRP levels.

The present disclosure also provides pharmaceutical compositions for use in any and/or all of the aforementioned methods, including for example, for the reduction, prevention or treatment of cardiovascular events and/or cardiovascular diseases, including acute cardiovascular disease or chronic cardiovascular disease, by administering a therapeutically effective amount of an anti-IL-1β binding antibody or binding fragment thereof.

Various methods and pharmaceutical compositions are provided herein, including for example, those described above. The present disclosure further provides IL-1β binding antibodies and binding fragments thereof, as well as suitable dose amounts and dosing regimens that may be used in or with any and/or all of the aforementioned methods and pharmaceutical compositions.

In some embodiments of any and/or all of the methods and pharmaceutical compositions described above, the antibody or fragment binds to human IL-1β with a dissociation constant of about 1 nM or less. In some embodiments, the antibody or fragment binds to human IL-1β with a dissociation constant of about 500 pM or less. In some embodiments, the anti-IL-1β binding antibody or binding fragment thereof binds to human IL-1β with a dissociation constant of about 250 pM or less. In some embodiments, the anti-IL-1β binding antibody or binding fragment thereof binds to human IL-1β with a dissociation constant of about 100 pM or less. In some embodiments of any of the methods described above, the anti-IL-1β binding antibody or binding fragment thereof binds to human IL-1β with a dissociation constant of about 50 pM or less. In some embodiments of any of the methods described above, the anti-IL-1β binding antibody or binding fragment thereof binds to human IL-1β with a dissociation constant of about 5 pM or less. In some embodiments, the anti-IL-1β binding antibody or binding fragment thereof binds to human IL-2β with a dissociation constant of about 1 pM or less. In some embodiments, the anti-IL-1β binding antibody or binding fragment thereof binds to human IL-1-β with a dissociation constant of about 0.3 pM or less.

In some embodiments of any and/or all of the methods described above, the anti-IL-1β binding antibody or binding fragment thereof is a neutralizing antibody.

In some embodiments of any and/or all of the methods described above, the anti-IL-1β binding antibody or binding fragment thereof binds to an IL-1β epitope such that the bound antibody or fragment substantially permits the binding of IL-1β to IL-1 receptor I (IL-1RI).

In some embodiments of any and/or all of the methods described above, the anti-IL-1β binding antibody or binding fragment thereof does not detectably bind to IL-1α, IL-1R or IL-1Ra.

In some embodiments of any and/or all of the methods described above, the anti-IL-1β binding antibody or binding fragment thereof competes with the binding of an antibody having the light chain variable region of SEQ ID NO:1 and the heavy chain variable region of SEQ ID NO:2. In some embodiments of any and/or all of the methods described above, the anti-IL-1β binding antibody or binding fragment thereof binds to an epitope that is the same or substantially the same as an epitope that is bound by an antibody having the light chain variable region of SEQ ID NO:1 and the heavy chain variable region of SEQ ID NO:2. In some embodiments of any and/or all of the methods described above, the anti-IL-1β binding antibody or binding fragment thereof comprises a light chain variable region of SEQ ID NO:1 and a heavy chain variable region of SEQ ID NO:2.

In some embodiments of any and/or all of the methods described above, the anti-IL-1β binding antibody or binding fragment thereof binds to an epitope incorporating Glu64 of IL-1β.

In some embodiments of any and/or all of the methods described above, the anti-IL-1β binding antibody or binding fragment thereof binds to amino acids 1-34 of the N terminus of IL-1β.

In some embodiments of any and/or all of the methods described above, the anti-IL-1β binding antibody or binding fragment thereof is humanized or human.

In some embodiments of any and/or all of the methods described above, the anti-IL-1β binding antibody or binding fragment thereof is administered in one or more doses of 3 mg/kg of antibody or fragment. In some embodiments, the anti-IL-1β binding antibody or binding fragment thereof is administered in one or more doses of 1 mg/kg or less of antibody or fragment. In some embodiments, the anti-IL-1β binding antibody or binding fragment thereof is administered in one or more doses of 0.3 mg/kg or less of antibody or fragment. In some embodiments, the anti-IL-1β binding antibody or binding fragment thereof is administered in one or more doses of 0.1 mg/kg or less of antibody or fragment. In some embodiments, the anti-IL-1β binding antibody or binding fragment thereof is administered in one or more doses of 0.03 mg/kg or less of antibody or fragment. In some embodiments, the one or more doses are at least 0.01 mg/kg of antibody or fragment. In some embodiments of any of the methods described above, the anti-IL-1β binding antibody or binding fragment thereof is administered in one or more doses of 0.03 mg/kg to 1 mg/kg.

In some embodiments of any and/or all of the methods described above, the anti-IL-1β binding antibody or binding fragment thereof is administered as a fixed dose, independent of a dose per subject weight ratio. In some embodiments, the anti-IL-1β binding antibody or binding fragment thereof is administered in one or more doses of 100 mg or less of antibody or fragment. In some embodiments, the anti-IL-1β binding antibody or binding fragment thereof is administered in one or more doses of 25 mg or less of antibody or fragment In some embodiments, the anti-IL-1β binding antibody or binding fragment thereof is administered in one or more doses of 10 mg or less of antibody or fragment. In some embodiments, the anti-IL-1β binding antibody or binding fragment thereof is administered in one or more doses of at least 0.5 mg of antibody or fragment. In some embodiments, the anti-IL-1β binding antibody or binding fragment thereof is administered in one or more doses of 1 mg to 100 mg of antibody or fragment. In some embodiments, said fixed dose of anti-IL-1β binding antibody or binding fragment thereof is administered using a pre-filled syringe or delivery device.

In some embodiments of any and/or all of the methods described above, the anti-IL-1β binding antibody or binding fragment thereof is administered by subcutaneous, intravenous or intramuscular injection.

In some embodiments of any and/or all of the methods described above, administration of an initial dose of anti-IL-1β binding antibody or binding fragment thereof is followed by the administration of one or more subsequent doses. In some embodiments, said initial dose and one or more subsequent doses are administered at an interval of about once every week to about once every 12 months. In some embodiments, said initial dose and one or more subsequent doses are administered at an interval of about once every two weeks to about once every 6 months. In some embodiments, said initial dose and one or more subsequent doses are administered at an interval of about once every month to about once every 6 months. In some embodiments, said initial dose and one or more subsequent doses are administered at an interval of about once every month to about once every 3 months. In some embodiments, said initial dose and one or more subsequent doses are administered at an interval of about once every 3 months to about once every 6 months.

In some embodiments of any and/or all of the aforementioned methods dosing regimens are provided, wherein the dosing regimen comprises more than one dosing interval for administration of an IL-1β binding antibody or binding fragment thereof. In some embodiments, the dosage regimen comprises at least two (e.g., two, three, four, five, six) different dosing intervals for administration of the IL-1β antibody or fragment thereof. In some embodiments, the dosage regimen comprises two different dosing intervals for administration of the IL-1β antibody or fragment thereof. In some embodiments, the dosing regimen comprises two different dosing intervals for administration of the IL-1β binding antibody or binding fragment thereof, wherein a first dosing interval comprises administration of one or more doses of the IL-1β antibody or fragment thereof and a second dosing interval comprises administration of one or more doses of the IL-1β antibody or fragment thereof, and wherein the first dosing interval is shorter in time than the second dosing interval. For example, the first dosing interval may be days or weeks, and the second dosing interval may be months. In some embodiments, the first dosing interval is about 5 days to about 28 days, about 7 days to about 21 days, about 12 days to about 16 days, or about 14 days. In some embodiments, the second dosing interval is about 1 month to about 3 months, about 1 month to about 2 months, or about 1 month. In some embodiments, the first dosing interval is about 7 days and the second dosing interval is about 1 month.

In some embodiments, administration of an initial dose of anti-IL-1β binding antibody or binding fragment thereof is followed by administration of one or more subsequent doses, and wherein the dosing intervals between administration of the initial dose and a second dose, and the second dose and a third dose are about 7 days to about 21 days, and wherein the dosing intervals between administration of subsequent doses is about 1 month to about 3 months. In some embodiments, the dosing intervals between administration of the initial dose and a second dose, and the second dose and a third dose are about 12 to 16 days, and the dosing intervals between administration of subsequent doses is about 1 month to about 2 months. In some embodiments, the dosing intervals between administration of the initial dose and a second dose, and the second dose and a third dose are about 14 days, and the dosing intervals between administration of subsequent doses is about 1 month.

In some preferred embodiments of any and/or all of the aforementioned methods, dose amounts and/or dosing regimens, the IL-1β binding antibody or binding fragment thereof (e.g., therapeutically effective amount of an anti-IL-1β binding antibody or binding fragment thereof) is first administered within 1 week of the cardiovascular event, within 96 hours of the cardiovascular event, within 72 hours of the cardiovascular event, within 48 hours of the cardiovascular event, within 24 hours of the cardiovascular event, or within 12 hours of the cardiovascular event.

In some embodiments of any and/or all of the methods described above, administration of an initial dose of the anti-IL-1β binding antibody or binding fragment thereof is followed by the administration of one or more subsequent doses, and wherein said one or more subsequent doses are in an amount that is approximately the same or less than the initial dose.

In some embodiments of any and/or all of the methods described above, administration of an initial dose of the anti-IL-1β binding antibody or binding fragment thereof is followed by the administration of one or more subsequent doses, and wherein at least one of the subsequent doses is in an amount that is more than the initial dose.

In some embodiments of any and/or all of the methods described above, the anti-IL-1β binding antibody or binding fragment thereof thereof has a lower $IC_{50}$ than an IL-1β receptor antagonist in a human whole blood IL-1β inhibition assay that measures IL-1β induced production of IL-8. In some embodiments, the IL-1β receptor antagonist is anakinra.

In some embodiments, any and/or all of the methods described above may further comprise administering at least one other pharmaceutical composition comprising an active agent other than an anti-IL-1β binding antibody or binding fragment thereof. In some embodiments, the active agent of said at least one other pharmaceutical composition is a cholesterol lowering agent. In some embodiments, the active agent of said at least one other pharmaceutical composition is a statin or an HMG-CoA reductase inhibitor (e.g., lovastatin, pravastatin, simvastatin, fluvastatin, atorvastatin, cerivastatin, mevastatin, pitavastatin, rosuvastatin or mixtures thereof or mixtures with Ezetimibe, niacin, Amlodipine Besylate). In some embodiments, the active agent of said at least one other pharmaceutical composition is a calcium channel blocker (e.g., amlodipine, diltiazem, nifedipine, nicardipine, verapamil) or a beta blocker (e.g., esmolol, metoprolol, nadolol, penbutolol). In some embodiments, the active agent of said at least one other pharmaceutical composition is an antihypertensive (e.g., labetalol, metoprolol, hydralazine, nitroglycerin, nicardipine, sodium nitroprusside, clevidipine), a diuretic (e.g., a thiazide diuretic, chlorthalidone, furosemide, hydrochlorothiazide, indapamide, metolazone, amiloride hydrochloride, spironolactone, triamterene) or aspirin. In some embodiments, the active agent of said at least one other pharmaceutical composition is an angiotensin-converting enzyme (ACE) inhibitor (e.g. ramipril, ramiprilat, captopril, lisinopril) or an angiotensin II receptor blocker (e.g., losartan, olmesartan, valsartan). In some embodiments, the active agent of said at least one other pharmaceutical composition is a vasodilator. In some embodiments, the active agent of said at least one other pharmaceutical composition is an anticoagulant (e.g., acenocoumarol, phenprocoumon, warfarin heparin, low molecular weight heparin) or inhibitor of platelet aggregation (e.g., clopidogrel, ticlopidine, cilostazol, dipyridamole, eptifibatide, aspirin, abciximab, eptifibatide, tirofiban). In some embodiments, the active agent of said at least one other pharmaceutical composition is a thrombolytic (e.g., streptokinase, urokinase, alteplase, reteplase, tenecteplase). In some embodiments, the active agent of said at least one other pharmaceutical composition is digitalis. In some embodiments, the active agent of said at least one other pharmaceutical composition is digoxin or nesiritide. In some embodiments, the active agent of said at least one other pharmaceutical composition is oxygen. In some embodiments, the active agent of said at least one other pharmaceutical composition is a thrombin inhibitor (e.g., hirudin, bivalirudin). In some embodiments, the active agent of said at least one other pharmaceutical composition is a nitrate (e.g., glyceryl trinitrate (GTN)/nitroglycerin, isosorbide dinitrate, isosorbide mononitrate). In some embodiments, the active agent of said at least one other pharmaceutical composition is an analgesic (e.g., morphine sulfate). In some embodiments, the active agent of said at least one other pharmaceutical composition is a renin inhibitor. In some embodiments, the active agent of said at least one other pharmaceutical composition is an endothelin A receptor inhibitor. In some embodiments, the active agent of said at least one other pharmaceutical composition is an aldosterone inhibitor.

The present disclosure also provides uses of an anti-IL-1β binding antibody or binding fragment thereof which has a lower $IC_{50}$ than an IL-1β receptor antagonist in a human whole blood IL-1β inhibition assay that measures IL-1β induced production of IL-8, in the manufacture of a composition for use in the reduction, prevention or treatment of a cardiac event or a cardiovascular disease.

These IL-1β binding antibodies and binding fragments thereof, as well as suitable dose amounts and dosing regimens and/or other pharmaceutical compositions comprising an active agent other than an anti-IL-1β antibody or fragment thereof, as provided herein, may be used in or with any of the aforementioned methods and/or pharmaceutical compositions, including for example:

Methods and/or pharmaceutical compositions for use in reducing a cardiovascular event (e.g., delaying time to event, reducing likelihood or risk of event, preventing an event, reducing severity of event, reducing time to recovery) in a subject with a history of at least one risk factor for cardiovascular disease, comprising administering to said subject a therapeutically effective amount of an anti-IL-1β binding antibody or binding fragment thereof, and wherein the cardiovascular event is myocardial infarction, stroke, cardiovascular death, congestive heart failure, cardiac arrest, acute coronary syndrome, angina, or a revascularization procedure;

Methods and/or pharmaceutical compositions for use in reducing a cardiovascular event (e.g., delaying time to event, reducing likelihood or risk of event, preventing an event, reducing severity of event, reducing time to recovery) in a subject with a history of a previous cardiovascular event, comprising administering to said subject a therapeutically effective amount of an anti-IL-1β binding antibody or binding fragment thereof, and wherein said cardiovascular event is myocardial infarction, stroke, cardiovascular death, congestive heart failure, cardiac arrest, acute coronary syndrome, angina or a revascularization procedure;

Methods and/or pharmaceutical compositions for use in reducing mortality following a cardiovascular event in a subject, comprising administering to said subject a therapeutically effective amount of an anti-IL-1β binding antibody or binding fragment thereof;

Methods and/or pharmaceutical compositions for use in reducing a cardiovascular event in a subject with a history of at least one risk factor for cardiovascular disease, comprising administering to said subject a therapeutically effective amount of an anti-IL-1β binding antibody or binding fragment thereof, and wherein said risk factor is not Type 2 diabetes, obesity, hyperglycemia, dyslipidemia, hyperlipidemia, chronic renal failure, high blood glucose, chronic kidney disease, hypertension, atherosclerosis or metabolic syndrome;

Methods and/or pharmaceutical compositions for use in treating a cardiovascular event in a subject, wherein the cardiovascular event is myocardial infarction, stroke, congestive heart failure, acute coronary syndrome or angina, comprising administering to said subject a therapeutically effective amount of an anti-IL-1β binding antibody or binding fragment thereof and at least one other pharmaceutical composition comprising an active agent other than an IL-1β antibody or fragment;

Methods and/or pharmaceutical compositions for use in treating a cardiovascular event in a subject, wherein the cardiovascular event is myocardial infarction, stroke, congestive heart failure, acute coronary syndrome or angina, comprising administering to said subject a therapeutically effective amount of an anti-IL-1β binding antibody or binding fragment thereof and a revascularization procedure;

Methods and/or pharmaceutical compositions for use in treating cardiovascular disease, including, for example, acute cardiovascular disease or chronic cardiovascular disease, in a subject, comprising administering to said subject a therapeutically effective amount of an anti-IL-1β binding antibody or binding fragment thereof and a revascularization procedure;

Methods and/or pharmaceutical compositions for use in reducing restenosis in a subject following a revascularization procedure, comprising administering to said subject a therapeutically effective amount of an anti-IL-1β binding antibody or binding fragment thereof;

Methods and/or pharmaceutical compositions for use in treating acute hypertension in a subject, comprising administering to said subject a therapeutically effective amount of an anti-IL-1β binding antibody or binding fragment thereof and one or more antihypertensive agents;

Methods and/or pharmaceutical compositions for use in reducing, preventing or treating a cardiovascular event or disease (e.g., acute cardiovascular disease or chronic cardiovascular disease) in a subject, comprising administering to the subject an anti-IL-1β binding antibody or binding fragment thereof in combination with a medical or surgical intervention;

Methods and/or pharmaceutical compositions for use in inhibiting platelet activity in a subject, comprising administering to said subject a therapeutically effective amount of an anti-IL-1β binding antibody or binding fragment thereof;

Methods and/or pharmaceutical compositions for use in reducing a cardiovascular event in a subject with a history of at least one risk factor for cardiovascular disease, comprising (a) identifying, diagnosing or selecting the subject with the history of at least one risk factor for cardiovascular disease and (b) administering to the subject a therapeutically effective amount of an anti-IL-1β binding antibody or binding fragment thereof, and wherein the cardiovascular event is myocardial infarction, stroke, cardiovascular death, congestive heart failure, cardiac arrest, acute coronary syndrome, angina, or a revascularization procedure;

Methods and/or pharmaceutical compositions for use in reducing a cardiovascular event in a subject with a history of a previous cardiovascular event, comprising (a) identifying, diagnosing or selecting the subject with the history of the previous cardiovascular event and (b) administering to the subject a therapeutically effective amount of an anti-IL-1β binding antibody or binding fragment thereof, and wherein the cardiovascular event is myocardial infarction, stroke, acute coronary syndrome, angina or a revascularization procedure;

Methods and/or pharmaceutical compositions for use in reducing mortality following a cardiovascular event in a subject, comprising (a) identifying, diagnosing or selecting the subject having the cardiovascular event and (b) administering to the subject a therapeutically effective amount of an anti-IL-1β binding antibody or binding fragment thereof;

Methods and/or pharmaceutical compositions for use in reducing a cardiovascular event in a subject with a history of at least one risk factor for cardiovascular disease, comprising (a) identifying, diagnosing or selecting the subject with the history of at least one risk factor for cardiovascular disease and (b) administering to the subject a therapeutically effective amount of an anti-IL-1β binding antibody or binding fragment thereof, and wherein the risk factor is not Type 2 diabetes, obesity, hyperglycemia, dyslipidemia, hyperlipidemia, chronic renal failure, high blood glucose, chronic kidney disease, hypertension, atherosclerosis or metabolic syndrome;

Methods and/or pharmaceutical compositions for use in treating a cardiovascular event in a subject, wherein the cardiovascular event is myocardial infarction, stroke, congestive heart failure, acute coronary syndrome or angina, comprising (a) identifying, diagnosing or selecting the subject with the cardiovascular event and (b) administering to the subject a therapeutically effective amount of an anti-IL-1β binding antibody or binding fragment thereof and at least one other pharmaceutical composition comprising an active agent other than an IL-1β antibody or fragment;

Methods and/or pharmaceutical compositions for use in treating a cardiovascular event in a subject, wherein the cardiovascular event is myocardial infarction, stroke, congestive heart failure, acute coronary syndrome or angina, comprising (a) identifying, diagnosing or selecting the subject with the cardiovascular event and (b) administering to the subject a therapeutically effective amount of an anti-IL-1β binding antibody or binding fragment thereof and (e.g., in conjunction with) a revascularization procedure;

Methods and/or pharmaceutical compositions for use in reducing restenosis in a subject following a revascularization procedure, comprising (a) identifying, diagnosing or selecting the subject with the revascularization procedure and (b) administering to the subject a therapeutically effective amount of an anti-IL-1β binding antibody or binding fragment thereof;

Methods and/or pharmaceutical compositions for use in treating acute hypertension in a subject comprising (a) identifying, diagnosing or selecting the subject with acute hypertension and (b) administering to the subject a therapeutically effective amount of an anti-IL-1β binding antibody or binding fragment thereof and one or more antihypertensive agents.

It should be understood that where the present specification provides methods of using IL-1β antibodies or binding fragments thereof with certain properties (such as Kd values or $IC_{50}$ values), such as for example, for the reduction, prevention or treatment of cardiovascular events and/or cardiovascular diseases, including acute cardiovascular disease or chronic cardiovascular disease, this also means to embody the use of such antibodies or fragments thereof in the manufacture of a medicament for use in these methods. Further, the disclosure also encompasses IL-1β antibodies or binding fragments thereof having these properties as well as pharmaceutical compositions comprising these antibodies or fragments thereof for use in the methods provided herein, such as for example, for the reduction, prevention or treatment of cardiovascular events and/or cardiovascular diseases, including acute cardiovascular disease or chronic cardiovascular disease.

BRIEF DESCRIPTION OF THE DRAWINGS

FIG. 9 is photographs of en face analysis showing reduction in the formation of atherosclerotic lesions in the aortas of ApoE knockout mice.

DETAILED DESCRIPTION

Figure 1:
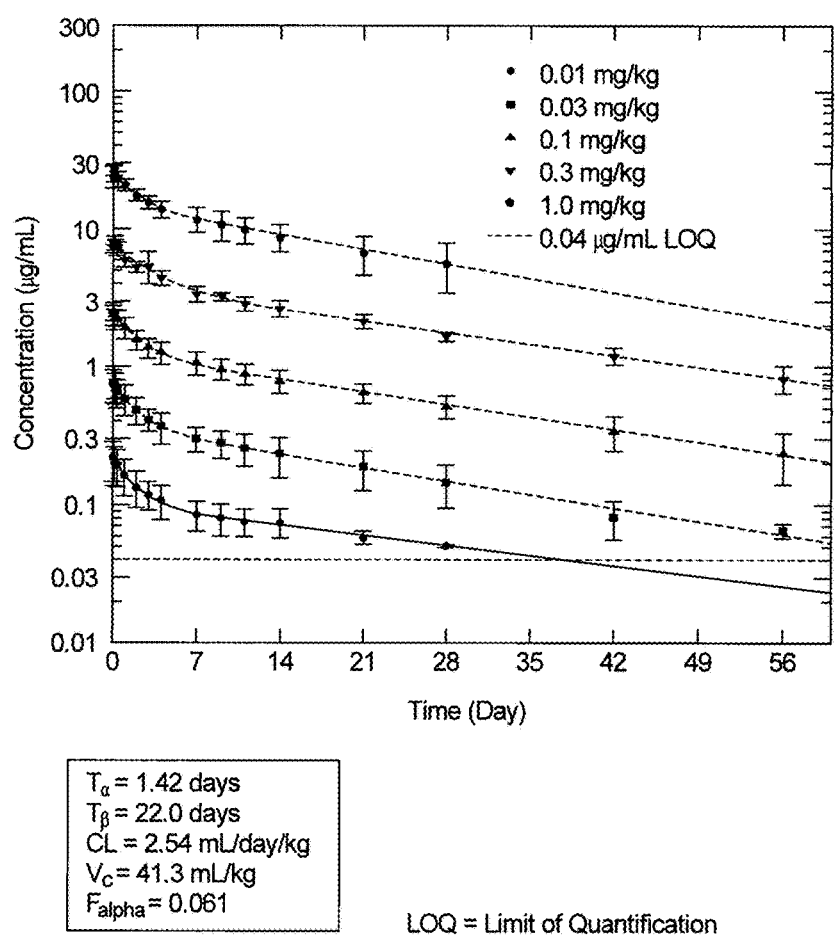
FIG. 1 is a graph showing serum concentrations following IV administration of 0.01, 0.03, 0.1, 0.3, or 1.0 mg/kg of an anti-IL-1β antibody in human subjects.

The present disclosure relates to methods and related articles of manufacture for the treatment and/or prevention of cardiovascular disease, including, for example, acute cardiovascular disease or chronic cardiovascular disease. The methods may be used for reducing, treating or preventing a cardiovascular event, such as myocardial infarction, stroke, cardiovascular death, congestive heart failure, cardiac arrest, acute coronary syndrome, angina, or a revascularization procedure in a subject, including in a subject with a history of a risk factor for cardiovascular disease. The methods may also be used to reduce mortality following a cardiovascular event in a subject. Use of anti-IL-1β binding antibodies or binding fragments as disclosed herein, offers potential advantages over previously available options, such as for example greater safety (e.g., reduced side effects), greater efficacy, targeting of the inflammatory component of disease, and/or less frequent dosing.

The interleukin-1 (IL-1) family of cytokines has been implicated in several disease states such as rheumatoid arthritis (RA), osteoarthritis, Crohn's disease, ulcerative colitis (UC), septic shock, chronic obstructive pulmonary disease (COPD), asthma, graft versus host disease, atherosclerosis, adult T-cell leukemia, multiple myeloma, multiple sclerosis, stroke, and Alzheimer's disease. IL-1 family members include IL-1α, IL-1β, and IL-1Ra. Although related by their ability to bind to IL-1 receptors (IL-1R1, IL-1R2), each of these cytokines is expressed by a different gene and has a different primary amino acid sequence. Furthermore, the physiological activities of these cytokines can be distinguished from each other.

Compounds that disrupt IL-1 receptor signaling have been investigated as therapeutic agents to treat IL-1 mediated diseases, such as for example some of the aforementioned diseases. These compounds include recombinant IL-1Ra (Amgen Inc., Thousand Oaks, Calif.), IL-1 receptor "trap" peptide (Regeneron Inc., Tarrytown, N.Y.), as well as animal-derived IL-1β antibodies and recombinant IL-1β antibodies and fragments thereof. Compounds that directly target the IL-1β ligand are believed to provide a superior strategy, particularly when administering an IL-1β antibody with high affinity.

Antibodies, Humanized Antibodies, and Human Engineered Antibodies

IL-1 (e.g., IL-1β) binding antibodies may be provided as polyclonal antibodies, monoclonal antibodies (mAbs), recombinant antibodies, chimeric antibodies, CDR-grafted antibodies, fully human antibodies, single chain antibodies, and/or bispecific antibodies, as well as fragments, including variants and derivatives thereof, provided by known techniques, including, but not limited to enzymatic cleavage, peptide synthesis or recombinant techniques.

Antibodies generally comprise two heavy chain polypeptides and two light chain polypeptides, though single domain antibodies having one heavy chain and one light chain, and heavy chain antibodies devoid of light chains are also contemplated. There are five types of heavy chains, called alpha, delta, epsilon, gamma and mu, based on the amino acid sequence of the heavy chain constant domain. These different types of heavy chains give rise to five classes of antibodies, IgA (including $IgA_1$ and $IgA_2$), IgD, IgE, IgG and IgM, respectively, including four subclasses of IgG, namely $IgG_1$, $IgG_2$, $IgG_3$ and $IgG_4$. There are also two types of light chains, called kappa (κ) or lambda (λ) based on the amino acid sequence of the constant domains. A full-length antibody includes a constant domain and a variable domain. The constant region need not be present in an antigen binding fragment of an antibody. Antigen binding fragments of an antibody disclosed herein can include Fab, Fab', F(ab')$_2$, and F(v) antibody fragments. As discussed in more detail below, IL-1β binding fragments encompass antibody fragments and antigen-binding polypeptides that will bind IL-1β.

Each of the heavy chain and light chain sequences of an antibody, or antigen binding fragment thereof, includes a variable region with three complementarity determining regions (CDRs) as well as non-CDR framework regions (FRs). The terms "heavy chain" and "light chain," as used herein, mean the heavy chain variable region and the light chain variable region, respectively, unless otherwise noted. Heavy chain CDRs are referred to herein as CDR-H1, CDR-H2, and CDR-H3. Light chain CDRs are referred to herein as CDR-L1, CDR-L2, and CDR-L3. Variable regions and CDRs in an antibody sequence can be identified (i) according to general rules that have been developed in the art or (ii) by aligning the sequences against a database of known variable regions. Methods for identifying these regions are described in Kontermann and Dubel, eds., *Antibody Engineering*, Springer, New York, N.Y., 2001, and Dinarello et al., *Current Protocols in Immunology*, John Wiley and Sons Inc., Hoboken, N.J., 2000. Databases of antibody sequences are described in and can be accessed through "The Kabatman" database at www.bioinf.org.uk/abs (maintained by A. C. Martin in the Department of Biochemistry & Molecular Biology University College London, London, England) and VBASE2 at www.vbase2.org, as described in Retter et al., *Nucl. Acids Res.*, 33(Database issue): D671-D674 (2005). The "Kabatman" database web site also includes general rules of thumb for identifying CDRs. The term "CDR," as used herein, is as defined in Kabat et al., *Sequences of Immunological Interest*, 5th ed., U.S. Department of Health and Human Services, 1991, unless otherwise indicated.

Polyclonal antibodies are preferably raised in animals by multiple subcutaneous (sc) or intraperitoneal (ip) immunizing injections of the relevant antigen and an adjuvant, using standard techniques known in the art. An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against different determinants (epitopes). In addition to their specificity, the monoclonal antibodies are advantageous in that they are synthesized by the homogeneous culture, uncontaminated by other immunoglobulins with different specificities and characteristics.

Monoclonal antibodies to be used in accordance with the present disclosure may be made by the hybridoma method first described by Kohler et al., (*Nature*, 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (*Nature* 352:624-628, 1991) and Marks et al., (*J. Mol. Biol.* 222:581-597, 1991).

It is further contemplated that antibodies of the present disclosure may be used as smaller antigen binding fragments of the antibody well-known in the art and described herein. The present disclosure encompasses IL-1 (e.g., IL-1β) binding antibodies that include two full length heavy chains and two full length light chains. Alternatively, the IL-1β binding antibodies can be constructs such as single chain antibodies or "mini" antibodies that retain binding activity to IL-1β. Such constructs can be prepared by methods known in the art such as, for example, the PCR mediated cloning and assembly of single chain antibodies for expression in *E. coli* (as described in Antibody Engineering, The practical approach series, J. McCafferty, H. R. Hoogenboom, and D. J. Chiswell, editors, Oxford University Press, 1996). In this type of construct, the variable portions of the heavy and light chains of an antibody molecule are PCR amplified from cDNA. The resulting amplicons are then assembled, for example, in a second PCR step, through a linker DNA that encodes a flexible protein linker composed of the amino acids Gly and Ser. This linker allows the variable heavy and light chain portions to fold in such a way that the antigen binding pocket is regenerated and antigen is bound with affinities often comparable to the parent full-length dimeric immunoglobulin molecule.

The IL-1 (e.g., IL-1β) binding antibodies and fragments encompass variants of the exemplary antibodies, fragments and sequences disclosed herein. Variants include peptides and polypeptides comprising one or more amino acid sequence substitutions, deletions, and/or additions that have the same or substantially the same affinity and specificity of epitope binding as one or more of the exemplary antibodies, fragments and sequences disclosed herein. Thus, variants include peptides and polypeptides comprising one or more amino acid sequence substitutions, deletions, and/or additions to the exemplary antibodies, fragments and sequences disclosed herein where such substitutions, deletions and/or additions do not cause substantial changes in affinity and specificity of epitope binding. For example, a variant of an antibody or fragment may result from one or more changes to an antibody or fragment, where the changed antibody or fragment has the same or substantially the same affinity and specificity of epitope binding as the starting sequence. Variants may be naturally occurring, such as allelic or splice variants, or may be artificially constructed. Variants may be prepared from the corresponding nucleic acid molecules encoding said variants. Variants of the present antibodies and IL-1β binding fragments may have changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of IL-1 (e.g., IL-1β) binding antibodies and binding fragments may also be prepared by mutagenesis techniques. For example, amino acid changes may be introduced at random throughout an antibody coding region and the resulting variants may be screened for binding affinity for IL-1β or for another property. Alternatively, amino acid changes may be introduced in selected regions of an IL-1β antibody, such as in the light and/or heavy chain CDRs, and/or in the framework regions, and the resulting antibodies may be screened for binding to IL-1β or some other activity. Amino acid changes encompass one or more amino acid substitutions in a CDR, ranging from a single amino acid difference to the introduction of multiple permutations of amino acids within a given CDR, such as CDR3. In another method, the contribution of each residue within a CDR to IL-1β binding may be assessed by substituting at least one residue within the CDR with alanine. Lewis et al. (1995), Mol. Immunol. 32: 1065-72. Residues which are not optimal for binding to IL-1β may then be changed in order to determine a more optimum sequence. Also encompassed are variants generated by insertion of amino acids to increase the size of a CDR, such as CDR3. For example, most light chain CDR3 sequences are nine amino acids in length. Light chain sequences in an antibody which are shorter than nine residues may be optimized for binding to IL-1β by insertion of appropriate amino acids to increase the length of the CDR.

Variants may also be prepared by "chain shuffling" of light or heavy chains. Marks et al. (1992), Biotechnology 10: 779-83. A single light (or heavy) chain can be combined with a library having a repertoire of heavy (or light) chains and the resulting population is screened for a desired activity, such as binding to IL-1β. This permits screening of a greater sample of different heavy (or light) chains in combination with a single light (or heavy) chain than is possible with libraries comprising repertoires of both heavy and light chains.

The IL-1 (e.g., IL-1β) binding antibodies and fragments of the present disclosure encompass derivatives of the exemplary antibodies, fragments and sequences disclosed herein. Derivatives include polypeptides or peptides, or variants, fragments or derivatives thereof, which have been chemically modified. Examples include covalent attachment of one or more polymers, such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The IL-1β binding antibodies and fragments can be bispecific. Bispecific antibodies or fragments can be of several configurations. For example, bispecific antibodies may resemble single antibodies (or antibody fragments) but have two different antigen binding sites (variable regions). Bispecific antibodies can be produced by chemical techniques (Kranz et al. (1981), Proc. Natl. Acad. Sci. USA, 78: 5807), by "polydoma" techniques (U.S. Pat. No. 4,474,893) or by recombinant DNA techniques. Bispecific antibodies of the present disclosure can have binding specificities for at least two different epitopes, at least one of which is an epitope of IL-1β. The IL-1β binding antibodies and fragments can also be heteroantibodies. Heteroantibodies are two or more antibodies, or antibody binding fragments (Fab) linked together, each antibody or fragment having a different specificity.

Techniques for creating recombinant DNA versions of the antigen-binding regions of antibody molecules which bypass the generation of monoclonal antibodies are contemplated for the present IL-1 (e.g., IL-1β) binding antibodies and fragments. DNA is cloned into a bacterial expression system. One example of such a technique suitable for the practice of the present disclosure uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind IL-1β. Such IL-1β binding agents (Fab fragments with specificity for an IL-1β polypeptide) are specifically encompassed within the IL-1β binding antibodies and fragments of the present disclosure.

The present IL-1 (e.g., IL-1β) binding antibodies and fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment is a non-human (e.g., mouse) antibody that has been engineered by modifying (e.g., deleting, inserting, or substituting) amino acids at specific positions so as to reduce or eliminate any detectable immunogenicity of the modified antibody in a human.

Humanized antibodies include chimeric antibodies and CDR-grafted antibodies. Chimeric antibodies are antibodies that include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad Sci. USA,* 81: 6841-6855 (1984), Boulianne, et al., *Nature,* 312: 643-646 (1984), and PCT Application Publication WO 86/01533. Although, they can be less immunogenic than a mouse monoclonal antibody, administrations of chimeric antibodies have been associated with human anti-mouse antibody responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), Proc. Natl. Acad. Sci., 81: 6851; Neuberger et al. (1984), Nature, 312: 604. One example is the replacement of a Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody of the present disclosure can comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., *Nature,* 321: 522-525 (1986), Riechmann et al., *Nature,* 332: 323-327 (1988), and Verhoeyen et al., *Science,* 239: 1534-1536 (1988)). Methods that can be used to produce humanized antibodies also are described in U.S. Pat. Nos. 4,816,567, 5,721,367, 5,837,243, and 6,180,377. CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., *Nature,* 332: 323-327 (1988), and Verhoeyen et al., *Science,* 239: 1534-1536 (1988).

Human engineered antibodies include for example "veneered" antibodies and antibodies prepared using HUMAN ENGINEERING™ technology (U.S. Pat. No. 5,869,619). HUMAN ENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or antigen-binding properties. Thus, a low risk position is one for which a substitution is predicted to be beneficial because it is predicted to reduce immunogenicity without significantly affecting antigen binding properties. A moderate risk position is one for which a substitution is predicted to reduce immunogenicity, but is more likely to affect protein folding and/or antigen binding. High risk positions contain residues most likely to be involved in proper folding or antigen binding. Generally, low risk positions in a non-human antibody are substituted with human residues, high risk positions are rarely substituted, and humanizing substitutions at moderate risk positions are sometimes made, although not indiscriminately. Positions with prolines in the non-human antibody variable region sequence are usually classified as at least moderate risk positions.

The particular human amino acid residue to be substituted at a given low or moderate risk position of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., *Protein Engineering*, 7: 805-814 (1994), U.S. Pat. Nos. 5,766,886, 5,770,196, 5,821,123, and 5,869,619, and PCT Application Publication WO 93/11794.

"Veneered" antibodies are non-human or humanized (e.g., chimeric or CDR-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody and replacing at least one of them with the corresponding surface residues from a human framework region. Veneering can be accomplished by any suitable engineering technique, including the use of the above-described HUMAN ENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (ii) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., *Antibody Engineering*, Springer, New York, N.Y., 2001.

Exemplary humanized or human engineered antibodies include IgG, IgM, IgE, IgA, and IgD antibodies. The present antibodies can be of any class (IgG, IgA, IgM, IgE, IgD, etc.) or isotype and can comprise a kappa or lambda light chain. For example, a human antibody can comprise an IgG heavy chain or defined fragment, such as at least one of isotypes, IgG1, IgG2, IgG3 or IgG4. As a further example, the present antibodies or fragments can comprise an IgG1 heavy chain and an IgG1 light chain.

The present antibodies and fragments can be human antibodies, such as antibodies which bind IL-1β polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851, 1996), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102, 2002) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TC MOUSE™ with various human antigens produces antibody responses comprising human antibodies.

See also Jakobovits et al., *Proc. Natl. Acad. Sci. USA*, 90:2551 (1993); Jakobovits et al., *Nature*, 362:255-258 (1993); Bruggermann et al., *Year in Immunol.*, 7:33 (1993); and U.S. Pat. Nos. 5,591,669, 5,589,369, 5,545,807; and U.S Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human antibodies can also be generated through the in vitro screening of antibody display libraries. See Hoogenboom et al. (1991), J. Mol. Biol. 227: 381; and Marks et al. (1991), J. Mol. Biol. 222: 581. Various antibody-containing phage display libraries have been described and may be readily prepared. Libraries may contain a diversity of human antibody sequences, such as human Fab, Fv, and scFv fragments, that may be screened against an appropriate target. Phage display libraries may comprise peptides or proteins other than antibodies which may be screened to identify selective binding agents of IL-1β.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The present disclosure contemplates a method for producing target-specific antibody or antigen-binding portion thereof comprising the steps of synthesizing a library of human antibodies on phage, screening the library with target protein or a portion thereof, isolating phage that bind target, and obtaining the antibody from the phage. By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the present disclosure may be obtained in this way.

Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the present disclosure can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) *Hum. Antibod. Hybridomas* 3:81-85; Huse et al. (1989) Science 246:1275-1281; McCafferty et al., Nature (1990) 348:552-554; Griffiths et al. (1993) *EMBO J* 12:725-734; Hawkins et al. (1992) *J. Mol. Biol.* 226:889-896; Clackson et al. (1991) Nature 352:624-628; Gram et al. (1992) *Proc. Natl. Acad. Sci. USA* 89:3576-3580; Garrad et al. (1991) *Bio/Technology* 9:1373-1377; Hoogenboom et al. (1991) Nuc Acid Res 19:4133-4137; and Barbas et al. (1991) *Proc. Natl. Acad. Sci. USA* 88:7978-7982.

In one embodiment, to isolate human antibodies specific for the target antigen with the desired characteristics, a human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (*Nature* 348:552-554, 1990); and Griffiths et al., (*EMBO J* 12:725-734, 1993). The scFv antibody libraries preferably are screened using target protein as the antigen.

Alternatively, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol*, 222:581-597 (1991); U.S. Pat. Nos. 5,565,332 and 5,573,905; Clackson, T., and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); Winter, G., et al., *Annu. Rev. Immunol.* 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178: 187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, Ike, ZJ/Z, Ff and one of the class II phages Xf, Pf1 and Pf3. The phage may be M13, or fd or a derivative thereof.

Once initial human $V_L$ and $V_H$ segments are selected, "mix and match" experiments, in which different pairs of the initially selected $V_L$ and $V_H$ segments are screened for target binding, are performed to select preferred $V_L N_H$ pair combinations. Additionally, to further improve the quality of the antibody, the $V_L$ and $V_H$ segments of the preferred $V_L/V_H$ pair(s) can be randomly mutated, preferably within the any of the CDR1, CDR2 or CDR3 region of $V_H$ and/or $V_L$, in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to target antigen.

Following screening and isolation of an target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the present disclosure, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (Bio/Technology, 10:779-783, 1992).

Methods for display of peptides on the surface of yeast and microbial cells have also been used to identify antigen specific antibodies. See, for example, U.S. Pat. No. 6,699,658. Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial cell display methods. Selection of polypeptide using ribosome display is described in Hanes et al., (Proc. Natl Acad Sci USA, 94:4937-4942, 1997) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

The IL-1 (e.g., IL-1β) binding antibodies and fragments may comprise one or more portions that do not bind IL-1β but instead are responsible for other functions, such as circulating half-life, direct cytotoxic effect, detectable labeling, or activation of the recipient's endogenous complement cascade or endogenous cellular cytotoxicity. The antibodies or fragments may comprise all or a portion of the constant region and may be of any isotype, including IgA (e.g., IgA1 or IgA2), IgD, IgE, IgG (e.g. IgG1, IgG2, IgG3 or IgG4), or IgM. In addition to, or instead of, comprising a constant region, antigen-binding compounds of the present disclosure may include an epitope tag, a salvage receptor epitope, a label moiety for diagnostic or purification purposes, or a cytotoxic moiety such as a radionuclide or toxin.

The constant region (when present) of the present antibodies and fragments may be of the γ1, γ2, γ3, γ4, μ, β2, or δ or ε type, preferably of the γ type, more preferably of the y, type, whereas the constant part of a human light chain may be of the κ or λ type (which includes the $\lambda_1$, $\lambda_2$ and $\lambda_3$ subtypes) but is preferably of the κ type.

Variants also include antibodies or fragments comprising a modified Fc region, wherein the modified Fc region comprises at least one amino acid modification relative to a wild-type Fc region. The variant Fc region may be designed, relative to a comparable molecule comprising the wild-type Fc region, so as to bind Fc receptors with a greater or lesser affinity.

For example, the present IL-1β binding antibodies and fragments may comprise a modified Fc region. Fe region refers to naturally-occurring or synthetic polypeptides homologous to the IgG C-terminal domain that is produced upon papain digestion of IgG. IgG Fc has a molecular weight of approximately 50 kD. In the present antibodies and fragments, an entire Fe region can be used, or only a half-life enhancing portion. In addition, many modifications in amino acid sequence are acceptable, as native activity is not in all cases necessary or desired.

The Fc region can be mutated, if desired, to inhibit its ability to fix complement and bind the Fc receptor with high affinity. For murine IgG Fc, substitution of Ala residues for Glu 318, Lys 320, and Lys 322 renders the protein unable to direct ADCC. Substitution of Glu for Leu 235 inhibits the ability of the protein to bind the Fe receptor with high affinity. Various mutations for human IgG also are known (see, e.g., Morrison et al., 1994, The Immunologist 2: 119 124 and Brekke et al., 1994, The Immunologist 2: 125).

In some embodiments, the present an antibodies or fragments are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fe region of an IgG molecule (e.g., $IgG_1$, $IgG_2$, $IgG_3$, or $IgG_4$) that is responsible for increasing the in vivo serum half-life of the IgG molecule.

A salvage receptor binding epitope can include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Mutation of residues within Fc receptor binding sites can result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position). For example it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., *Mol Immunol.* 30:105-8, 1993).

Antibody fragments are portions of an intact full length antibody, such as an antigen binding or variable region of the intact antibody. Examples of antibody fragments include Fab, Fab', $F(ab')_2$, and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), adnectins, binding-domain immunoglobulin fusion proteins; camelized antibodies; $V_{HH}$ containing antibodies; and any other polypeptides formed from antibody fragments.

The present disclosure includes IL-1β binding antibody fragments comprising any of the foregoing heavy or light chain sequences and which bind IL-1β. The term fragments as used herein refers to any 3 or more contiguous amino acids (e.g., 4 or more, 5 or more 6 or more, 8 or more, or even 10 or more contiguous amino acids) of the antibody and encompasses Fab, Fab', $F(ab')_2$, and F(v) fragments, or the individual light or heavy chain variable regions or portion thereof. IL-1β binding fragments include, for example, Fab, Fab', $F(ab')_2$, Fv and scFv. These fragments lack the Fc fragment of an intact antibody, clear more rapidly from the circulation, and can have less non-specific tissue binding than an intact antibody. See Wahl et al. (1983), J. Nucl. Med., 24: 316-25. These fragments can be produced from intact antibodies using well known methods, for example by proteolytic cleavage with enzymes such as papain (to produce Fab fragments) or pepsin (to produce $F(ab')_2$ fragments).

In vitro and cell based assays are well described in the art for use in determining binding of IL-1β to IL-1 receptor type I (IL-1R1), including assays that determining in the presence of molecules (such as antibodies, antagonists, or other inhibitors) that bind to IL-1β or IL-1RI. (see for example Evans et al., (1995), J. Biol. Chem. 270:11477-11483; Vigers et al., (2000), J. Biol. Chem. 275:36927-36933; Yanofsky et al., (1996), Proc. Natl. Acad. Sci. USA 93:7381-7386; Fredericks et al., (2004), Protein Eng. Des. Sel. 17:95-106; Slack et al., (1993), J. Biol. Chem. 268:2513-2524; Smith et al., (2003), Immunity 18:87-96; Vigers et al., (1997), Nature 386:190-194; Ruggiero et al., (1997), J. Immunol. 158:3881-3887; Guo et al., (1995), J. Biol. Chem. 270:27562-27568; Svenson et al., (1995), Eur. J. Immunol. 25:2842-2850; Arend et al., (1994), J. Immunol. 153:4766-4774). Recombinant IL-1 receptor type I, including human IL-1 receptor type I, for such assays is readily available from a variety of commercial sources (see for example R&D Systems, SIGMA). IL-1 receptor type I also can be expressed from an expression construct or vector introduced into an appropriate host cell using standard molecular biology and transfection techniques known in the art. The expressed IL-1 receptor type I may then be isolated and purified for use in binding assays, or alternatively used directly in a cell associated form.

For example, the binding of IL-1β to IL-1 receptor type I may be determined by immobilizing an IL-1β binding antibody, contacting IL-1β with the immobilized antibody and determining whether the IL-1β was bound to the antibody, and contacting a soluble form of IL-1β with the bound IL-1β/antibody complex and determining whether the soluble IL-1RI was bound to the complex. The protocol may also include contacting the soluble IL-1RI with the immobilized antibody before the contact with IL-1β, to confirm that the soluble IL-1RI does not bind to the immobilized antibody. This protocol can be performed using a Biacore® instrument for kinetic analysis of binding interactions. Such a protocol can also be employed to determine whether an antibody or other molecule permits or blocks the binding of IL-1β to IL-1 receptor type I.

For other IL-1β/IL-1RI binding assays, the permitting or blocking of IL-1β binding to IL-1 receptor type I may be determined by comparing the binding of IL-1β to IL-1RI in the presence or absence of IL-1β antibodies or IL-1β binding fragments thereof. Blocking is identified in the assay readout as a designated reduction of IL-1β binding to IL-1 receptor type I in the presence of anti-IL-1β antibodies or IL-1β binding fragments thereof, as compared to a control sample that contains the corresponding buffer or diluent but not an IL-1β antibody or IL-1β binding fragment thereof. The assay readout may be qualitatively viewed as indicating the presence or absence of blocking, or may be quantitatively viewed as indicating a percent or fold reduction in binding due to the presence of the antibody or fragment.

Alternatively or additionally, when an IL-1β binding antibody or IL-1β binding fragment substantially blocks IL-1β binding to IL-1RI, the IL-1β binding to IL-1RI is reduced by at least 10-fold, alternatively at least about 20-fold, alternatively at least about 50-fold, alternatively at least about 100-fold, alternatively at least about 1000-fold, alternatively at least about 10000-fold, or more, compared to binding of the same concentrations of IL-1β and IL-1RI in the absence of the antibody or fragment. As another example, when an IL-1β binding antibody or IL-1β binding fragment substantially permits IL-1β binding to IL-1RI, the IL-1β binding to IL-1RI is at least about 90%, alternatively at least about 95%, alternatively at least about 99%, alternatively at least about 99.9%, alternatively at least about 99.99%, alternatively at least about 99.999%, alternatively at least about 99.9999%, alternatively substantially identical to binding of the same concentrations of IL-1β and IL-1R1 in the absence of the antibody or fragment.

The present disclosure may in certain embodiments encompass IL-1β binding antibodies or IL-1β binding fragments that bind to the same epitope or substantially the same epitope as one or more of the exemplary antibodies described herein. Alternatively or additionally, the IL-1β binding antibodies or IL-1β binding fragments compete with the binding of an antibody having variable region sequences of AB7, described in U.S. application Ser. No. 11/472,813 (sequences shown below). Alternatively or additionally, the present disclosure encompasses IL-1β binding antibodies and fragments that bind to an epitope contained in the amino acid sequence ESVDPKNYPKKKMEKRFVFNKIE (SEQ ID NO: 3). As contemplated herein, one can readily determine if an IL-1β binding antibody or fragment binds to the same epitope or substantially the same epitope as one or more of the exemplary antibodies, such as for example the antibody designated AB7, using any of several known methods in the art.

For example, the key amino acid residues (epitope) bound by an IL-1β binding antibody or fragment may be determined using a peptide array, such as for example, a PepSpot™ peptide array (JPT Peptide Technologies, Berlin, Germany), wherein a scan of twelve amino-acid peptides, spanning the entire IL-1β amino acid sequence, each peptide overlapping by 11 amino acid to the previous one, is synthesized directly on a membrane. The membrane carrying the peptides is then probed with the antibody for which epitope binding information is sought, for example at a concentration of 2 µg/ml, for 2 hr at room temperature. Binding of antibody to membrane bound peptides may be detected using a secondary HRP-conjugated goat anti-human (or mouse, when appropriate) antibody, followed by enhanced chemiluminescence (ECL). The peptides spot(s) corresponding to particular amino acid residues or sequences of the mature IL-1β protein, and which score positive for antibody binding, are indicative of the epitope bound by the particular antibody.

Alternatively or in addition, antibody competition experiments may be performed and such assays are well known in the art. For example, to determine if an antibody or fragment binds to an epitope contained in a peptide sequence comprising the amino acids ESVDPKNYPKKKMEKRFVF-NKIE (SEQ ID NO: 3), which corresponds to residues 83-105 of the mature IL-1β protein, an antibody of unknown specificity may be compared with any of the exemplary of antibodies (e.g., AB7) of the present disclosure. Binding competition assays may be performed, for example, using a Biacore® instrument for kinetic analysis of binding interactions or by ELISA. In such an assay, the antibody of unknown epitope specificity is evaluated for its ability to compete for binding against the known comparator antibody (e.g., AB7). Competition for binding to a particular epitope is determined by a reduction in binding to the IL-1β epitope of at least about 50%, or at least about 70%, or at least about 80%, or at least about 90%, or at least about 95%, or at least about 99% or about 100% for the known comparator antibody (e.g., AB7) and is indicative of binding to substantially the same epitope.

In view of the identification in this disclosure of IL-1β binding regions in exemplary antibodies and/or epitopes recognized by the disclosed antibodies, it is contemplated that additional antibodies with similar binding characteristics and therapeutic or diagnostic utility can be generated that parallel the embodiments of this disclosure.

Antigen-binding fragments of an antibody include fragments that retain the ability to specifically bind to an antigen, generally by retaining the antigen-binding portion of the antibody. It is well established that the antigen-binding function of an antibody can be performed by fragments of a full-length antibody. Examples of antigen-binding portions include (i) a Fab fragment, which is a monovalent fragment consisting of the VL, VH, CL and CH1 domains; (ii) a F(ab')$_2$ fragment, which is a bivalent fragment comprising two Fab fragments linked by a disulfide bridge at the hinge region; (iii) a Fd fragment which is the VH and CH1 domains; (iv) a Fv fragment which is the VL and VH domains of a single arm of an antibody, (v) a dAb fragment (Ward et al., (1989) Nature 341:544-546), which is a VH domain; and (vi) an isolated complementarity determining region (CDR). Single chain antibodies are also encompassed within the term antigen-binding portion of an antibody. The IL-1β binding antibodies and fragments of the present disclosure also encompass monovalent or multivalent, or monomeric or multimeric (e.g. tetrameric), CDR-derived binding domains with or without a scaffold (for example, protein or carbohydrate scaffolding).

The present IL-1β binding antibodies or fragments may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibodies and fragments comprising immunoadhesion molecules can be obtained using standard recombinant DNA techniques, as described herein. Preferred antigen binding portions are complete domains or pairs of complete domains.

The IL-1β binding antibodies and fragments of the present disclosure also encompass domain antibody (dAb) fragments (Ward et al., Nature 341:544-546, 1989) which consist of a $V_H$ domain. The IL-1β binding antibodies and fragments of the present disclosure also encompass diabodies, which are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *Proc. Natl. Acad. Sci. USA* 90:6444-6448, 1993, and Poljak et al., *Structure* 2:1121-1123, 1994). Diabodies can be bispecific or monospecific.

The IL-1β binding antibodies and fragments of the present disclosure also encompass single-chain antibody fragments (scFv) that bind to IL-1β. An scFv comprises an antibody heavy chain variable region ($V_H$) operably linked to an antibody light chain variable region ($V_L$) wherein the heavy chain variable region and the light chain variable region, together or individually, form a binding site that binds IL-1β. An scFv may comprise a $V_H$ region at the amino-terminal end and a $V_L$ region at the carboxy-terminal end. Alternatively, scFv may comprise a $V_L$ region at the amino-terminal end and a $V_H$ region at the carboxy-terminal end. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883).

An scFv may optionally further comprise a polypeptide linker between the heavy chain variable region and the light chain variable region. Such polypeptide linkers generally comprise between 1 and 50 amino acids, alternatively between 3 and 12 amino acids, alternatively 2 amino acids. An example of a linker peptide for linking heavy and light chains in an scFv comprises the 5 amino acid sequence Gly-Gly-Gly-Gly-Ser (SEQ ID NO: 6). Other examples comprise one or more tandem repeats of this sequence (for example, a polypeptide comprising two to four repeats of Gly-Gly-Gly-Gly-Ser (SEQ ID NO: 6) to create linkers.

The IL-1β binding antibodies and fragments of the present disclosure also encompass heavy chain antibodies (HCAb). Exceptions to the $H_2L_2$ structure of conventional antibodies occur in some isotypes of the immunoglobulins found in camelids (camels, dromedaries and llamas; Hamers-Casterman et al., 1993 Nature 363: 446; Nguyen et al., 1998 J. Mol. Biol. 275: 413), wobbegong sharks (Nuttall et al., *Mol Immunol.* 38:313-26, 2001), nurse sharks (Greenberg et al., Nature 374:168-73, 1995; Roux et al., 1998 Proc. Nat. Acad. Sci. USA 95: 11804), and in the spotted ratfish (Nguyen, et al., "Heavy-chain antibodies in Camelidae; a case of evolutionary innovation," 2002 Immunogenetics 54(1): 39-47). These antibodies can apparently form antigen-binding regions using only heavy chain variable regions, in that these functional antibodies are dimers of heavy chains only (referred to as "heavy-chain antibodies" or "HCAbs"). Accordingly, some embodiments of the present IL-1β binding antibodies and fragments may be heavy chain antibodies that specifically bind to IL-1β. For example, heavy chain antibodies that are a class of IgG and devoid of light chains are produced by animals of the genus Camelidae which includes camels, dromedaries and llamas (Hamers-Casterman et al., Nature 363:446-448 (1993)). HCAbs have a molecular weight of about 95 kDa instead of the about 160 kDa molecular weight of conventional IgG antibodies. Their binding domains consist only of the heavy-chain variable domains, often referred to as $V_{HH}$ to distinguish them from conventional $V_H$. Muyldermans et al., J. Mol. Recognit. 12:131-140 (1999). The variable domain of the heavy-chain antibodies is sometimes referred to as a nanobody (Cortez-Retamozo et al., Cancer Research 64:2853-57, 2004). A nanobody library may be generated from an immunized dromedary as described in Conrath et al., (*Antimicrob Agents Chemother* 45: 2807-12, 2001) or using recombinant methods.

Since the first constant domain ($C_{H1}$) is absent (spliced out during mRNA processing due to loss of a splice consensus signal), the variable domain ($V_{HH}$) is immediately followed by the hinge region, the $C_{H2}$ and the $C_{H3}$ domains (Nguyen et al., Mol. Immunol. 36:515-524 (1999); Woolven et al., Immunogenetics 50:98-101 (1999)). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains.

Although the HCAbs are devoid of light chains, they have an antigen-binding repertoire. The genetic generation mechanism of HCAbs is reviewed in Nguyen et al. Adv. Immunol 79:261-296 (2001) and Nguyen et al., Immunogenetics 54:39-47 (2002). Sharks, including the nurse shark, display similar antigen receptor-containing single monomeric V-domains. Irving et al., J. Immunol. Methods 248: 31-45 (2001); Roux et al., Proc. Natl. Acad. Sci. USA 95:11804 (1998).

$V_{HH}$s comprise small intact antigen-binding fragments (for example, fragments that are about 15 kDa, 118-136 residues). Camelid $V_{HH}$ domains have been found to bind to antigen with high affinity (Desmyter et al., *J. Biol. Chem.* 276:26285-90, 2001), with $V_{HH}$ affinities typically in the nanomolar range and comparable with those of Fab and scFv fragments. $V_{HH}$s are highly soluble and more stable than the corresponding derivatives of scFv and Fab fragments. $V_H$ fragments have been relatively difficult to produce in soluble form, but improvements in solubility and specific binding can be obtained when framework residues are altered to be more $V_{HH}$-like. (See, for example, Reichman et al., J Immunol Methods 1999, 231:25-38.) $V_{HH}$s carry amino acid substitutions that make them more hydrophilic and prevent prolonged interaction with BiP (immunoglobulin heavy-chain binding protein), which normally binds to the H-chain in the Endoplasmic Reticulum (ER) during folding and assembly, until it is displaced by the L-chain. Because of the $V_{HH}$s' increased hydrophilicity, secretion from the ER is improved.

Functional $V_{HH}$s may be obtained by proteolytic cleavage of HCAb of an immunized camelid, by direct cloning of $V_{HH}$ genes from B-cells of an immunized camelid resulting in recombinant $V_{HH}$s, or from naive or synthetic libraries. $V_{HH}$s with desired antigen specificity may also be obtained through phage display methodology. Using $V_{HH}$s in phage display is much simpler and more efficient compared to Fabs or scFvs, since only one domain needs to be cloned and expressed to obtain a functional antigen-binding fragment. Muyldermans, Biotechnol. 74:277-302 (2001); Ghahroudi et al., FEBS Lett. 414:521-526 (1997); and van der Linden et al., J. Biotechnol. 80:261-270 (2000). Methods for generating antibodies having camelid heavy chains are also described in U.S. Patent Publication Nos. 20050136049 and 20050037421.

Ribosome display methods may be used to identify and isolate scFv and/or $V_{HH}$ molecules having the desired binding activity and affinity. Irving et al., J. Immunol. Methods 248:31-45 (2001). Ribosome display and selection has the potential to generate and display large libraries ($10^{14}$).

Other embodiments provide $V_{HH}$-like molecules generated through the process of camelisation, by modifying non-Camelidae $V_H$s, such as human $V_H$s, to improve their solubility and prevent non-specific binding. This is achieved by replacing residues on the $V_L$s side of $V_H$s with $V_{HH}$-like residues, thereby mimicking the more soluble $V_{HH}$ fragments. Camelised $V_H$ fragments, particularly those based on the human framework, are expected to exhibit a greatly reduced immune response when administered in vivo to a patient and, accordingly, are expected to have significant advantages for therapeutic applications. Davies et al., FEBS Lett. 339:285-290 (1994); Davies et al., Protein Eng. 9:531-537 (1996); Tanha et al., J. Biol. Chem. 276:24774-24780 (2001); and Riechmann et al., Immunol. Methods 231:25-38 (1999).

A wide variety of expression systems are available for the production of IL-1β fragments including Fab fragments, scFv, and $V_{HH}$s. For example, expression systems of both prokaryotic and eukaryotic origin may be used for the large-scale production of antibody fragments and antibody fusion proteins. Particularly advantageous are expression systems that permit the secretion of large amounts of antibody fragments into the culture medium.

Production of bispecific Fab-scFv ("bibody") and trispecific Fab-(scFv)(2) ("tribody") are described in Schoonjans et al. (*J ImmunoL* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab. A "minibody" consisting of scFv fused to CH3 via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

The IL-1β binding antibodies and fragments of the present disclosure also encompass antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

The IL-1β binding antibodies and fragments of the present disclosure also encompass immunoadhesins. One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs disclosed herein permit the immunoadhesin to specifically bind to IL-1β.

The IL-1β binding antibodies and fragments of the present disclosure also encompass antibody mimics comprising one or more IL-1β binding portions built on an organic or molecular scaffold (such as a protein or carbohydrate scaffold). Proteins having relatively defined three-dimensional structures, commonly referred to as protein scaffolds, may be used as reagents for the design of antibody mimics. These scaffolds typically contain one or more regions which are amenable to specific or random sequence variation, and such sequence randomization is often carried out to produce libraries of proteins from which desired products may be selected. For example, an antibody mimic can comprise a chimeric non-immunoglobulin binding polypeptide having an immunoglobulin-like domain containing scaffold having two or more solvent exposed loops containing a different CDR from a parent antibody inserted into each of the loops and exhibiting selective binding activity toward a ligand bound by the parent antibody. Non-immunoglobulin protein scaffolds have been proposed for obtaining proteins with novel binding properties. (Tramontano et al., J. Mol. Recognit. 7:9, 1994; McConnell and Hoess, J. Mol. Biol. 250:460, 1995). Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164:243, 1995; Wang et al., J. Biol. Chem. 270:12250, 1995). Methods for employing scaffolds for antibody mimics are disclosed in U.S. Pat. No. 5,770,380 and US Patent Publications 2004/0171116, 2004/0266993, and 2005/0038229.

The anti-IL-1β binding antibodies or binding fragments thereof for use in the methods herein generally bind to IL-1β with high affinity (e.g., as determined with BIACORE). In preferred embodiments, the antibody or fragment thereof binds to IL-1β with an equilibrium binding dissociation constant ($K_D$) of about 10 nM or less, about 5 nM or less, about 1 nM or less, about 500 pM or less, about 250 pM or less, about 100 pM or less, about 50 pM or less, or about 25 pM or less. In particularly preferred embodiments, the antibody or antibody fragment binds to human IL-1β with a dissociation constant of about 100 pM or less, about 50 pM or less, about 10 pM or less, about 5 pM or less, about 3 pM or less, about 1 pM or less, about 0.75 pM or less, about 0.5 pM or less, about 0.3 pM or less, about 0.2 pM or less, or about 0.1 pM or less. In particularly preferred embodiments, the antibody or antibody fragment binds to human IL-1β with a dissociation constant of about 10 pM or less.

Antibodies or fragments of the present disclosure may, for example, bind to IL-1β with an $IC_{50}$ of about 10 nM or less, about 5 nM or less, about 2 nM or less, about 1 nM or less, about 0.75 nM or less, about 0.5 nM or less, about 0.4 nM or less, about 0.3 nM or less, or even about 0.2 nM or less, as determined by enzyme linked immunosorbent assay (ELISA). Preferably, the antibody or antibody fragment of the present disclosure does not cross-react with any target other than IL-1. For example, the present antibodies and fragments may bind to IL-1β, but do not detectably bind to IL-1α, or have at least about 100 times (e.g., at least about 150 times, at least about 200 times, or even at least about 250 times) greater selectivity in its binding of IL-1β relative to its binding of IL-1α. Antibodies or fragments used according to the present disclosure may, in certain embodiments, inhibit IL-1β induced expression of serum IL-6 in an animal by at least 50% (e.g., at least 60%, at least 70%, or even at least 80%) as compared to the level of serum IL-6 in an IL-1β stimulated animal that has not been administered an antibody or fragment of the present disclosure. Antibodies may bind IL-1β but permit or substantially permit the binding of the bound IL-1β ligand to IL-1 receptor type I (IL-1RI). In contrast to many known IL-1β binding antibodies that block or substantially interfere with binding of IL-1β to IL-1RI, the antibodies designated AB5 and AB7 (U.S. application Ser. No. 11/472,813) selectively bind to the IL-1β ligand, but permit the binding of the bound IL-1β ligand to IL-1RI. For example, the antibody designated AB7 binds to an IL-1β epitope but still permits the bound IL-1β to bind to IL-1RI. In certain embodiments, the antibody may decrease the affinity of interaction of bound IL-1β to bind to IL-1RI. Accordingly, the disclosure provides, in a related aspect, use of an IL-1β binding antibody or IL-1β binding antibody fragment that has at least one of the aforementioned characteristics. Any of the foregoing antibodies, antibody fragments, or polypeptides of the disclosure can be humanized or human engineered, as described herein.

A variety of IL-1 (e.g., IL-1β) antibodies and fragments known in the art may be used according the methods provided herein, including for example antibodies described in or derived using methods described in the following patents and patent applications: U.S. Pat. No. 4,935,343; US 2003/0026806; US 2003/0124617 (e.g., antibody AAL160); WO 2006/081139 (e.g., antibody 9.5.2); WO 03/034984; WO 95/01997 (e.g., antibody SK48-E26 VTKY); U.S. Pat. No. 7,446,175 (e.g., antibody ACZ 885); WO 03/010282 (e.g., antibody Hu007); WO 03/073982 (e.g., antibody N55S), U.S. Pat. No. 7,541,033 (e.g., W17, U43, W13, W18, W20), U.S. Pat. No. 7,491,392, WO 2004/072116, WO 2004/067568, EP 0 267 611 B1, EP 0 364 778 B1, and U.S. application Ser. No. 11/472,813. As a non-limiting example, antibodies AB5 and AB7 (U.S. application Ser. No. 11/472, 813, WO2007/002261) may be used in accordance with the present disclosure. Variable region sequences of AB5 and AB7 are as follows:

AB7
LIGHT CHAIN
(SEQ ID NO: 1)
DIQMTQSTSSLSASVGDRVTITC<u>RASODISNYLS</u>WYQQKPGKAVKLLIY<u>Y</u>

<u>TSKLHS</u>GVPSRFSGSGSGTDYTLTISSLQQEDFATYFC<u>LQGICMLPWT</u>FG

QGTKLEIK

The underlined sequences depict (from left to right) CDR1, 2 and 3.

HEAVY CHAIN
(SEQ ID NO: 2)
QVQLQESGPGLVKPSQTLSLTCSFSGFSLS<u>TSGMGVG</u>WIRQPSGKGLEWL

<u>AHIWWDGDESYNPSLKS</u>RLTISKDTSKNQVSLKITSVTAADTAVYFCAR<u>N</u>

<u>RYDPPWFVDW</u>GQGTLVTVSS

The underlined sequences depict (from left to right) CDR1, 2 and 3.

AB5
LIGHT CHAIN
(SEQ ID NO: 4)
DIQMTQTTSSLSASLGDRVTISC<u>RASQDISNYLS</u>WYQQKPDGTVKLLIY<u>Y</u>

<u>TSKLHS</u>GVPSRFSGSGSGTDYSLTISNLEQEDIATYFC<u>LQGKNILPWT</u>FG

GGTKLEIK

The underlined sequences depict (from left to right) CDR1, 2 and 3.

HEAVY CHAIN
(SEQ ID NO: 5)
QVTLKESGPGILKPSQTLSLTCSFSGFSLS<u>TSGMGVG</u>WIRQPSGKGLEWL

<u>AHIWWDGDESYNPSLK</u>TQLTISKDTSRNQVFLKITSVDTVDTATYFCAR<u>N</u>

<u>RYDPPWFVDW</u>GQGTLVTVSS

The underlined sequences depict (from left to right) CDR1, 2 and 3.

In some embodiments, IL-1β antibodies or fragments thereof for use in any and/or all of the methods disclosed herein may bind to human IL-1β with a dissociation constant of about 1 nM or less. In some embodiments, the antibody or fragment binds to human IL-1β with a dissociation constant of about 500 pM or less. In some embodiments, the anti-IL-1β binding antibody or binding fragment thereof binds to human IL-1β with a dissociation constant of about 250 pM or less. In some embodiments, the anti-IL-1β binding antibody or binding fragment thereof binds to human IL-1β with a dissociation constant of about 100 pM or less. In some embodiments, the antibody or fragment binds to human IL-1β with a dissociation constant of about 50 pM or less. In some embodiments, the antibody or fragment binds to human IL-1β with a dissociation constant of about 10 pM or less. In some embodiments, the antibody or fragment binds to human IL-1β with a dissociation constant of about 5 pM or less. In some embodiments, the antibody or fragment binds to human IL-1β with a dissociation constant of about 1 pM or less. In some embodiments, the antibody or fragment binds to human IL-1β with a dissociation constant of about 0.3 pM or less.

In some embodiments, the anti-IL-1β binding antibody or binding fragment thereof is a neutralizing antibody.

In some embodiments, the anti-IL-1β binding antibody or binding fragment thereof binds to an IL-1β epitope such that the bound antibody or fragment substantially permits the binding of IL-1β to IL-1 receptor I (IL-1RI).

In some embodiments, the anti-IL-1β binding antibody or binding fragment thereof does not detectably bind to IL-1α, IL-1R or IL-1Ra.

In some embodiments, the anti-IL-1β binding antibody or binding fragment thereof competes with the binding of an antibody having the light chain variable region of SEQ ID NO:1 and the heavy chain variable region of SEQ ID NO:2. In some embodiments of any of the methods described above, the anti-IL-1β binding antibody or binding fragment thereof binds to an epitope that is the same or substantially the same as an epitope that is bound by an antibody having the light chain variable region of SEQ ID NO:1 and the heavy chain variable region of SEQ ID NO:2. In some embodiments of any of the methods described above, the anti-IL-1β binding antibody or binding fragment thereof comprises a light chain variable region of SEQ ID NO:1 and a heavy chain variable region of SEQ ID NO:2.

In some embodiments, the anti-IL-1β binding antibody or binding fragment thereof binds to an epitope incorporating Glu64 of IL-1β.

In some embodiments, the anti-IL-1β binding antibody or binding fragment thereof binds to amino acids 1-34 of the N terminus of IL-1β.

In some embodiments, the anti-IL-1β binding antibody or binding fragment thereof is humanized or human.

The present disclosure also provides uses of an anti-IL-1β binding antibody or binding fragment thereof which has a lower $IC_{50}$ than an IL-1β receptor antagonist in a human whole blood IL-1β inhibition assay that measures IL-1β induced production of IL-8, in the manufacture of a composition for use in the reduction, prevention or treatment of a cardiac event or a cardiovascular disease.

In another aspect, the methods comprise administering a therapeutically effective amount of an anti-IL-1β antibody or fragment thereof, wherein the antibody or fragment thereof has a lower $IC_{50}$ than an IL-1β receptor antagonist in a human whole blood IL-1β inhibition assay that measures IL-1β induced production of IL-8. In one embodiment, the antibody or fragment has an $IC_{50}$ that is less than about 90%, 80%, 70%, 60%, 50% of the $IC_{50}$ of an IL-1β receptor antagonist in a human whole blood IL-1β inhibition assay that measures IL-1β induced production of IL-8. In a further embodiment, the antibody or fragment has an $IC_{50}$ that is less than about 40%, 30%, 20%, 10% of the $IC_{50}$ of an IL-1β receptor antagonist in a human whole blood IL-1β inhibition assay that measures IL-1β induced production of IL-8. In a preferred embodiment, the antibody or fragment has an $IC_{50}$ that is less than about 8%, 5%, 4%, 3%, 2%, 1% of the $IC_{50}$ of an IL-1β receptor antagonist in a human whole blood IL-1β inhibition assay that measures IL-1β induced production of IL-8. In one embodiment, the IL-1β receptor antagonist is anakinra (i.e., Kineret®).

In another aspect, the method provided herein comprises administering a therapeutically effective amount of an anti-IL-1β antibody or fragment thereof to the subject, wherein the antibody or fragment thereof provides in vivo inhibition of IL-1β stimulated release of IL-6 in mice compared to a control antibody using an assay that is described by Economides et al., *Nature Med.*, 9:47-52 (2003) which is incorporated by reference. In one embodiment the antibody or fragment provides in vivo inhibition of IL-1β stimulated release of IL-6 in mice of at least about 10%, 20%, 30%, 40%, 50% compared to the control antibody. In a further embodiment, the antibody or fragment provides in vivo inhibition of IL-1β stimulated release of IL-6 in mice of at least about 60%, 70%, 80%, 90%, 95% compared to the control antibody. In one embodiment, the control antibody is an isotype control antibody.

In another aspect, the disclosure provides a method comprising administering a therapeutically effective amount of an anti-IL-1β antibody or fragment thereof to the human, wherein the antibody or fragment thereof inhibits *Staphylococcus epidermidis* induced cytokine production in human whole blood compared to a control where no antibody is used. In one embodiment the antibody or fragment provides a greater level of inhibition of *Staphylococcus epidermidis* induced cytokine production in human whole blood by at least about 10%, 20%, 30%, 40%, 50% compared to the control. In a further embodiment, the antibody or fragment provides a greater level of inhibition of *Staphylococcus epidermidis* induced cytokine production in human whole blood by at least about 60%, 70%, 80%, 90%, 95% compared to the control. In one embodiment, the inhibited cytokines are IL-1β, IL-1α, IL-6, IL-8, IL-1Ra, TNFα or IFNγ.

The antibodies and antibody fragments described herein can be prepared by any suitable method. Suitable methods for preparing such antibodies and antibody fragments are known in the art. Other methods for preparing the antibodies and antibody fragments are as described herein as part of the disclosure. The antibody, antibody fragment, or polypeptide of the present disclosure, as described herein, can be isolated or purified to any degree. As used herein, an isolated compound is a compound that has been removed from its natural environment. A purified compound is a compound that has been increased in purity, such that the compound exists in a form that is more pure than it exists (i) in its natural environment or (ii) when initially synthesized and/or amplified under laboratory conditions, wherein "purity" is a relative term and does not necessarily mean "absolute purity."

Pharmaceutical Compositions

IL-1 (e.g., IL-1β) binding antibodies and antibody fragments for use according to the present disclosure can be formulated in compositions, especially pharmaceutical compositions, for use in the methods herein. Such compositions comprise a therapeutically or prophylactically effective amount of an IL-1β binding antibody or antibody fragment of the disclosure in admixture with a suitable carrier, e.g., a pharmaceutically acceptable agent. Typically, IL-1β binding antibodies and antibody fragments of the disclosure are sufficiently purified for administration to an animal before formulation in a pharmaceutical composition.

Pharmaceutically acceptable agents include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in *Remington's Pharmaceutical Sciences,* 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); poly (ethylene glycol) phenyl ethers (e.g. Triton); sodium dodecyl sulfate (SDS); sodium laurel sulfate; sodium octyl glycoside; lauryl-, myristyl-, linoleyk or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, intralesional, intrarectal, transdermal, oral, and inhaled routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) sustained release and/or increased stability or half-life in a particular local environment. The present disclosure contemplates that in certain embodiments such compositions may include a significantly larger amount of antibody or fragment in the initial deposit, while the effective amount of antibody or fragment actually released and available at any point in time for is in accordance with the disclosure herein an amount much lower than the initial deposit. The compositions can include the formulation of IL-1β binding antibodies, antibody fragments, nucleic acids, or vectors of the disclosure with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly (2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon- (rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humour of the eye. Esterified derivatives of hyaluronic acid have been used to produce microspheres for use in delivery that are biocompatible and biodegrable (see for example, Cortivo et al., Biomaterials (1991) 12:727-730; European Publication No. 517,565; International Publication No. WO 96/29998; Illum et al., J. Controlled Rel. (1994) 29:133-141). Exemplary hyaluronic acid containing compositions of the present disclosure comprise a hyaluronic acid ester polymer in an amount of approximately 0.1% to about 40% (w/w) of an IL-1β binding antibody or fragment to hyaluronic acid polymer.

Both biodegradable and non-biodegradable polymeric matrices can be used to deliver compositions in accordance with the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which can be used to form the biodegradable delivery system include: polymers of lactic acid and glycolic acid, polyamides, polycarbonates, polyalkylenes, polyalkylene glycols, polyalkylene oxides, polyalkylene terephthalates, polyvinyl alcohols, polyvinyl ethers, polyvinyl esters, poly-vinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see for example WO 04/009664, WO 05/087201, Sawhney, et al., Macromolecules, 1993, 26, 581-587,) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324).

A pharmaceutical composition comprising an IL-1β binding antibody or fragment can be formulated for inhalation, such as for example, as a dry powder. Inhalation solutions also can be formulated in a liquefied propellant for aerosol delivery. In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 μm to 5 μm; however, larger particles may be used, for example, if each particle is fairly porous.

Certain formulations containing IL-1β binding antibodies or antibody fragments can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of an IL-1β binding antibody or fragment in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations can be determined in view of the present disclosure and general knowledge of formulation technology, depending upon the intended route of administration, delivery format, and desired dosage. Regardless of the manner of administration, an effective dose can be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages can be ascertained through use of appropriate dose-response data.

Additional formulations will be evident in light of the present disclosure, including formulations involving IL-1β binding antibodies and fragments in combination with one or more other therapeutic agents. For example, in some formulations, an IL-1β binding antibody, antibody fragment, nucleic acid, or vector of the disclosure is formulated with a second inhibitor of an IL-1 signaling pathway Representative second inhibitors include, but are not limited to, antibodies, antibody fragments, peptides, polypeptides, compounds, nucleic acids, vectors and pharmaceutical compositions, such as, for example, those described in U.S. Pat. No. 6,899,878, US 2003022869, US 20060094663, US 20050186615, US 20030166069, WO/04022718, WO/05084696, WO/05019259. For example, a composition may comprise an IL-1β binding antibody, antibody fragment, nucleic acid, or vector of the disclosure in combination with an IL-1β binding antibody, fragment, or a nucleic acid or vector encoding such an antibody or fragment.

Methods of Use

Anti-IL-1β binding antibodies or binding fragments thereof in a therapeutically effective amount may be used as disclosed by the methods herein for the treatment and/or prevention of cardiovascular disease, including, for example, acute cardiovascular disease or chronic cardiovascular disease. Such methods, as well as pharmaceutical compositions for use in such methods, may be used for reducing, treating or preventing a cardiovascular event, such as myocardial infarction, stroke, cardiovascular death, congestive heart failure, cardiac arrest, acute coronary syndrome, angina, or a revascularization procedure in a subject, including in a subject with a history of a risk factor for cardiovascular disease. The methods and pharmaceutical compositions may also be used to reduce mortality following a cardiovascular event in a subject. The present disclosure also contemplates the use of other IL-1 pathway inhibitors, as an alternative or in addition to the anti-IL-1β antibodies or fragments.

The terms "prevention", "prevent", "preventing", "suppression", "suppress", "suppressing", "inhibit" and "inhibition" as used herein with respect to methods as described refer to preventing, suppressing or reducing, either temporarily or permanently, the onset of a clinical symptoms or manifestation of an event, disease or condition, such as, for example, a cardiovascular event or disease, (e.g., acute or chronic cardiovascular disease). Such preventing, suppressing or reducing need not be absolute to be useful.

The terms "reduce", "reducing" and "reduction" as used herein with respect to the methods as described refer to delaying the time to an event or disease, decreasing the likelihood or risk of an event or disease, decreasing the incidence of an event or disease (e.g., in a treatment group), preventing the occurrence of an event or disease (e.g., prevention of a cardiovascular event or disease), decreasing the magnitude or severity of an event or disease (except in the case where the event is death), and/or decreasing the time to recovery from an event or disease (except in the case where the event is death), such as, for example, treating or treatment of a cardiovascular event or disease, (e.g., acute or chronic cardiovascular disease).

The phrase "mortality following a cardiovascular event" as used herein refers to mortality (i.e., death) that occurs after a cardiovascular event (e.g., after initiation of the cardiovascular event), and which may be, but need not be, directly or indirectly caused by or influenced by the cardiovascular event. Following also refers to the proximity in time (e.g., measurable) between the cardiovascular event and mortality, regardless of whether or not a direct or indirect causal link can be determined. The proximity in time between the cardiovascular event and mortality may vary and include an amount of time that is approaching being simultaneous.

The terms "treatment", "treat" and "treating" as used with respect to methods as described herein refers eliminating, reducing, suppressing or ameliorating, either temporarily or permanently, a clinical symptom, manifestation or progression of an event, disease or condition, such as, for example, a cardiovascular event or disease, (e.g., acute or chronic cardiovascular disease). Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or compound of the disclosure.

The term "therapeutically effective amount" as used herein refers to an amount of a compound (e.g., antibody), either alone or as a part of a pharmaceutical composition, that is capable of having any detectable, positive effect on any symptom, aspect, or characteristics of a disease state or condition when administered to a subject (e.g., as one or more doses), including, for example, reducing a cardiovascular event or disease, or reducing mortality following a cardiovascular event or disease, (e.g., acute or chronic cardiovascular disease). Such effect need not be absolute to be beneficial.

The present disclosure provides methods of treating a subject with cardiovascular disease, including, for example, acute cardiovascular disease or chronic cardiovascular disease, comprising administering to said subject a therapeutically effective amount of an anti-IL-1β binding antibody or binding fragment thereof.

The present disclosure provides methods of reducing a cardiovascular event in a subject, comprising administering to said subject a therapeutically effective amount of an anti-IL-1β binding antibody or binding fragment thereof, wherein the subject is a subject with a history of a previous cardiovascular event or a history of at least one risk factor for cardiovascular disease, and wherein the cardiovascular event is myocardial infarction, stroke, cardiovascular death, congestive heart failure, cardiac arrest, acute coronary syndrome, angina, or a revascularization procedure.

The present disclosure also provides methods of reducing a cardiovascular event (e.g., delaying time to event, reducing likelihood or risk of event, preventing an event, reducing severity of event, reducing time to recovery) in a subject with a history of at least one risk factor for cardiovascular disease, comprising administering to said subject a therapeutically effective amount of an anti-IL-1β binding antibody or binding fragment thereof, and wherein the cardiovascular event is myocardial infarction, stroke, cardiovascular death, congestive heart failure, cardiac arrest, acute coronary syndrome, angina, or a revascularization procedure.

The present disclosure also provides methods of reducing a cardiovascular event (e.g., delaying time to event, reducing likelihood or risk of event, preventing an event, reducing severity of event, reducing time to recovery) in a subject with a history of a previous cardiovascular event, comprising administering to said subject a therapeutically effective amount of an anti-IL-1β binding antibody or binding fragment thereof, and wherein said cardiovascular event is myocardial infarction, stroke, cardiovascular death, congestive heart failure, cardiac arrest, acute coronary syndrome, angina or a revascularization procedure. In some embodiments, the previous cardiovascular event is a first cardiovascular event. In some embodiments, the previous or first cardiovascular event is selected from the group consisting of myocardial infarction, stroke, congestive heart failure, acute coronary syndrome, angina and a revascularization procedure.

In some embodiments, the previous or first cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG).

In some embodiments, the method of reducing a cardiovascular event is a method of reducing a second or subsequent cardiovascular event. In some embodiments, the cardiovascular event (e.g., second or subsequent cardiovascular event) is selected from the group consisting of myocardial infarction, stroke, cardiovascular death, congestive heart failure, cardiac arrest, acute coronary syndrome, angina and a revascularization procedure. In some embodiments, the first cardiovascular event and second cardiovascular event are the same types of cardiovascular events. In some embodiments, the first cardiovascular event and second cardiovascular event are different types of cardiovascular events.

In some embodiments, the revascularization procedure is a coronary, carotid or peripheral arterial revascularization procedure. In some embodiments, the coronary, carotid or peripheral arterial revascularization procedure is a percutaneous coronary intervention (PCI), a stent implant, coronary artery bypass graft (CABG), carotid endarterectomy, peripheral vascular disease bypass surgery, or peripheral angioplasty surgery.

In some preferred embodiments, the therapeutically effective amount of an anti-IL-1β binding antibody or binding fragment thereof is first administered within 1 week of the cardiovascular event, within 96 hours of the cardiovascular event, within 72 hours of the cardiovascular event, within 48 hours of the cardiovascular event, within 24 hours of the cardiovascular event, or within 12 hours of the cardiovascular event. In some embodiments, the subject also has a history of at least one risk factor for cardiovascular disease. In some embodiments, the risk factor is manifest coronary heart disease, coronary artery disease, thrombosis, transient ischaemic attack, left ventricular hypertrophy, arteriosclerosis, restenosis, tobacco smoking or peripheral vascular disease. In some embodiments the peripheral vascular disease is clinically apparent (e.g., peripheral artery disease of Fontaine Class II or greater). In some embodiments, the risk factor is elevated triglycerides, systemic inflammation, high blood phosphorus levels, high parathyroid hormone levels, microalbuminuria, or high homocysteine levels. In some embodiments, the risk factor is obesity, hyperglycemia, chronic renal failure, high blood glucose, chronic kidney disease, or metabolic syndrome. In some embodiments, the risk factor is end stage renal disease. In some embodiments, the risk factor is hypertension, dyslipidemia, hyperlipidemia, elevated total cholesterol, elevated LDL cholesterol, or low HDL cholesterol or atherosclerosis. In some embodiments, the hypertension is manifested as a blood pressure of greater than or equal to 180/110 mm Hg. In some other embodiments, the hypertension is mild-to-moderate, with systolic blood pressure (SBP) of 140 to 180 mm Hg and/or diastolic blood pressure (DBP) of 90 to 110 mm Hg. In some embodiments, the subject has elevated levels of C-reactive protein (CRP). In some embodiments, the subject is older than 55 years. In some embodiments, the subject is older than 65 years. In some embodiments, the subject is non-hypertensive. In some embodiments, the subject has poorly controlled hypertension. In some embodiments, the subject has a "Type A" personality. In some embodiments, the subject has a sedentary lifestyle. In some embodiments, the subject has diabetes mellitus. In some embodiments, the diabetes mellitus is Type 2 diabetes. In some embodiments, the subject has a history of two or more said risk factors. In some embodiments, the subject has a history of three or more said risk factors.

In some embodiments, administering said therapeutically effective amount of an anti-IL-1β binding antibody or binding fragment thereof is sufficient to achieve a decrease in CRP levels.

The present disclosure also provides methods of reducing mortality following a cardiovascular event in a subject, comprising administering to said subject a therapeutically effective amount of an anti-IL-1β binding antibody or binding fragment thereof. In some embodiments, the cardiovascular event is myocardial infarction, stroke, cardiac arrest, congestive heart failure, cardiovascular death, acute coronary syndrome (e.g., diagnosed), angina or a revascularization procedure. In some embodiments, the cardiovascular event is myocardial infarction or acute coronary syndrome. In some embodiments, the myocardial infarction is myocardial infarction with ST elevation (e.g., ST-segment elevation myocardial infarction, STEMI). In some embodiments, the myocardial infarction is myocardial infarction without ST elevation (e.g., non-ST-segment elevation myocardial infarction, NSTEMI). In some embodiments the presence or absence of ST elevation is determined by electrocardiogram (e.g., ECG, EKG).

In some embodiments, mortality is death from cardiovascular causes. In other embodiments, mortality is death from any cause. In some embodiments, the cardiovascular event is myocardial infarction, stroke, congestive heart failure, acute coronary syndrome, angina or a revascularization procedure. In some embodiments, the revascularization procedure is a coronary, carotid or peripheral arterial revascularization procedure. In some embodiments, the coronary, carotid or peripheral arterial revascularization procedure is a percutaneous coronary intervention (PCI), a stent implant, coronary artery bypass graft (CABG), carotid endarterectomy, peripheral vascular disease bypass surgery, or peripheral angioplasty surgery.

In some preferred embodiments the therapeutically effective amount of an anti-IL-1β binding antibody or binding fragment thereof is first administered within 1 week of the cardiovascular event, within 96 hours of the cardiovascular event, within 72 hours of the cardiovascular event, within 48 hours of the cardiovascular event, within 24 hours of the cardiovascular event, or within 12 hours of the cardiovascular event. In some embodiments, the subject does not have Type 2 diabetes. In some embodiments, the subject has survived a previous cardiovascular event of myocardial infarction or stroke. In some embodiments, the occurrence of said cardiovascular event is a reoccurrence of a cardiovascular event of myocardial infarction or stroke.

In some embodiments, the subject has a history of one or more risk factors for cardiovascular disease. In some embodiments, the risk factor is manifest coronary heart disease, coronary artery disease, thrombosis, transient ischaemic attack, left ventricular hypertrophy, arteriosclerosis, restenosis, tobacco smoking or peripheral vascular disease. In some embodiments the peripheral vascular disease is clinically apparent (e.g., peripheral artery disease of Fontaine Class II or greater). In some embodiments, the risk factor is elevated triglycerides, systemic inflammation, high blood phosphorus levels, high parathyroid hormone levels, microalbuminuria, or high homocysteine levels. In some embodiments, the risk factor is obesity, hyperglycemia, chronic renal failure, high blood glucose, chronic kidney disease, or metabolic syndrome. In some embodiments, the risk factor is hypertension, dyslipidemia, hyperlipidemia, elevated total cholesterol, elevated LDL cholesterol, or low HDL cholesterol or atherosclerosis. In some embodiments, the hypertension is manifested as a blood pressure of greater than or equal to 180/110 mm Hg. In some other embodiments, the hypertension is mild-to-moderate, with systolic blood pressure (SBP) of 140 to 180 mm Hg and/or diastolic blood pressure (DBP) of 90 to 110 mm Hg.

In some embodiments, the subject is non-hypertensive. In some embodiments, the subject has poorly controlled hypertension. In some embodiments, the subject has a "Type A" personality. In some embodiments, the subject has a sedentary lifestyle. In some embodiments, the subject has a history of two or more said risk factors. In some embodiments, the subject has a history of three or more said risk factors.

In some embodiments, administering said therapeutically effective amount of an anti-IL-1β binding antibody or binding fragment thereof is sufficient to achieve a decrease in CRP levels.

The present disclosure also provides methods of reducing a cardiovascular event in a subject with a history of at least one risk factor for cardiovascular disease, comprising administering to said subject a therapeutically effective amount of an anti-IL-1β binding antibody or binding fragment thereof, and wherein said risk factor is not Type 2 diabetes, obesity, hyperglycemia, dyslipidemia, hyperlipidemia, chronic renal failure, high blood glucose, chronic kidney disease, hypertension, atherosclerosis or metabolic syndrome.

In some embodiments, the cardiovascular event is myocardial infarction, stroke, cardiac arrest, congestive heart failure, cardiovascular death, acute coronary syndrome (e.g., diagnosed), angina or a revascularization procedure. In some embodiments, the revascularization procedure is a coronary, carotid or peripheral arterial revascularization procedure. In some embodiments, the coronary, carotid or peripheral arterial revascularization procedure is a percutaneous coronary intervention (PCI), a stent implant, coronary artery bypass graft (CABG), carotid endarterectomy, peripheral vascular disease bypass surgery, or peripheral angioplasty surgery.

In some embodiments, the risk factor is manifest coronary heart disease, coronary artery disease, thrombosis, transient ischaemic attack, left ventricular hypertrophy, arteriosclerosis, restenosis, tobacco smoking or peripheral vascular disease. In some embodiments, the risk factor is elevated triglycerides, systemic inflammation, high blood phosphorus levels, high parathyroid hormone levels, microalbuminuria, or high homocysteine levels.

In some embodiments, the subject has elevated levels of C-reactive protein (CRP). In some embodiments, the subject is older than 55 years. In some embodiments, the subject is older than 65 years. In some embodiments, the subject has a history of two or more said risk factors. In some embodiments, the subject has a history of three or more said risk factors.

In some embodiments, administering said therapeutically effective amount of an anti-IL-1β binding antibody or binding fragment thereof is sufficient to achieve a decrease in CRP levels.

The present disclosure also provides methods of treating a cardiovascular event in a subject, wherein the cardiovascular event is myocardial infarction, stroke, congestive heart failure, acute coronary syndrome or angina, comprising administering to said subject a therapeutically effective amount of an anti-IL-1β binding antibody or binding fragment thereof and at least one other pharmaceutical composition comprising an active agent other than an IL-1β antibody or fragment.

In some embodiments, the active agent of said at least one other pharmaceutical composition is a cholesterol lowering agent, a statin, an HMG-CoA reductase inhibitor, a calcium channel blocker, a beta blocker, an antihypertensive, a diuretic, aspirin, niacin, an angiotensin-converting enzyme (ACE) inhibitor, an angiotensin II receptor blocker, a vasodilator, an anticoagulant, a inhibitor of platelet aggregation, a thrombolytic or digitalis.

The present disclosure also provides methods of treating a cardiovascular event in a subject, wherein the cardiovascular event is myocardial infarction, stroke, congestive heart failure, acute coronary syndrome or angina, comprising administering to said subject a therapeutically effective amount of an anti-IL-1β binding antibody or binding fragment thereof and a revascularization procedure. In some embodiments, the revascularization procedure is a coronary, carotid or peripheral arterial revascularization procedure.

The present disclosure also provides methods of reducing restenosis in a subject following a revascularization procedure, comprising administering to said subject a therapeutically effective amount of an anti-IL-1β binding antibody or binding fragment thereof. In some embodiments, the revascularization procedure is a coronary, carotid or peripheral arterial revascularization procedure.

The present disclosure also provides methods of treating acute hypertension in a subject comprising administering to said subject a therapeutically effective amount of an anti-IL-1β binding antibody or binding fragment thereof and one or more antihypertensive agents. In some embodiments, the subject has a blood pressure of greater than or equal to 180/110 mm Hg. In some other embodiments, the subject has mild-to-moderate hypertension, with systolic blood pressure (SBP) of 140 to 180 mm Hg and/or diastolic blood pressure (DBP) of 90 to 110 mm Hg. In some embodiments, the antihypertensive agent is administered intravenously. In some embodiments, the antihypertensive agent is selected from the group consisting of alpha/beta-adrenergic blocking agents, angiotensin-converting enzyme inhibitors, angiotensin II receptor antagonists, antiadrenergic agents, beta-adrenergic blocking agents, calcium-channel blocking agents, diuretics, and vasodilators. In some embodiments, the antihypertensive agent is carvedilol, labetalol, benazepril, captopril, enalapril, fosinopril, lisinopril, moexipril, perindopril, quinapril, ramipril, trandolapril, candesartan, eprosartan, irbesartan, losartan, telmisartan, valsartan, clonidine, doxazosin, guanabenz, guanadrel, guanethidine, guanfacine, mecamylamine, methyldopa, prazosin, reserpine, terazosin, acebutolol, atenolol, betaxolol, bisoprolol, carteolol, metoprolol, nadolol, penbutolol, pindolol, propranolol, timolol, amlodipine, diltiazem, felodipine, isradipine, nicardipine, nifedipine, nisoldipine, verapamil, amiloride, benzthiazide, chlorothiazide, chlorthalidone, furosemide, hydrochlorothiazide, indapamide, metolazone, polythiazide, spironolactone, torsemide, trichlormethiazide, hydralazine, nitroglycerin, sodium nitroprusside, clevidipine or minoxidil. In some embodiments, the antihypertensive agent is labetalol, metoprolol, hydralazine, nitroglycerin, nicardipine, sodium nitroprusside or clevidipine.

The present disclosure also provides methods of reducing, preventing or treating a cardiovascular event or disease in a subject comprising administering to the subject an anti-IL-1β binding antibody or binding fragment thereof in combination with (e.g., before, during or after) a medical or surgical intervention. Such antibodies may be administered in therapeutically effective amounts. Such interventions may be therapeutically effective. In some embodiments, a medical intervention is an active agent, such as a drug or a biologic, including, for example, any one or more of the active agents described herein. In some embodiments, a medical intervention is an out-patient medical treatment or procedure. In some embodiments, a medical intervention is an in-patient hospitalization. In some embodiments, a surgical intervention is a revascularization procedure, including, for example, any one or more of the revascularization procedures described herein. In some embodiments, a surgical intervention involves a heart valve repair or replacement, coronary bypass surgery, heart transplant or heart pump. In some embodiments, a surgical intervention involves a biventricular cardiac pacemaker, internal cardiac defibrillator (ICD) or myectomy. In some embodiments, a medical intervention is smoking cessation medication or smoking cessation counseling.

The present disclosure also provides methods of reducing a cardiovascular event in a subject with a history of at least one risk factor for cardiovascular disease, comprising (a) identifying, diagnosing or selecting the subject with the history of at least one risk factor for cardiovascular disease and (b) administering to the subject a therapeutically effective amount of an anti-IL-1β binding antibody or binding fragment thereof, and wherein the cardiovascular event is myocardial infarction, stroke, cardiovascular death, congestive heart failure, cardiac arrest, acute coronary syndrome, angina, or a revascularization procedure.

The present disclosure also provides methods of reducing a cardiovascular event in a subject with a history of a previous cardiovascular event, comprising (a) identifying, diagnosing or selecting the subject with the history of the previous cardiovascular event and (b) administering to the subject a therapeutically effective amount of an anti-IL-1β binding antibody or binding fragment thereof, and wherein the cardiovascular event is myocardial infarction, stroke, acute coronary syndrome, angina or a revascularization procedure.

The present disclosure also provides methods of reducing mortality following a cardiovascular event in a subject, comprising (a) identifying, diagnosing or selecting the subject having the cardiovascular event and (b) administering to the subject a therapeutically effective amount of an anti-IL-1β binding antibody or binding fragment thereof.

The present disclosure also provides methods of reducing a cardiovascular event in a subject with a history of at least one risk factor for cardiovascular disease, comprising (a) identifying, diagnosing or selecting the subject with the history of at least one risk factor for cardiovascular disease and (b) administering to the subject a therapeutically effective amount of an anti-IL-1β binding antibody or binding fragment thereof, and wherein the risk factor is not Type 2 diabetes, obesity, hyperglycemia, dyslipidemia, hyperlipidemia, chronic renal failure, high blood glucose, chronic kidney disease, hypertension, atherosclerosis or metabolic syndrome.

The present disclosure also provides methods of treating a cardiovascular event in a subject, wherein the cardiovascular event is myocardial infarction, stroke, congestive heart failure, acute coronary syndrome or angina, comprising (a) identifying, diagnosing or selecting the subject with the cardiovascular event and (b) administering to the subject a therapeutically effective amount of an anti-IL-1β binding antibody or binding fragment thereof and at least one other pharmaceutical composition comprising an active agent other than an IL-1β antibody or fragment.

The present disclosure also provides methods for treating a cardiovascular event in a subject, wherein the cardiovascular event is myocardial infarction, stroke, congestive heart failure, acute coronary syndrome or angina, comprising (a) identifying, diagnosing or selecting the subject with the cardiovascular event and (b) administering to the subject a therapeutically effective amount of an anti-IL-1β binding antibody or binding fragment thereof and a revascularization procedure.

The present disclosure also provides methods of reducing restenosis in a subject following a revascularization procedure, comprising (a) identifying, diagnosing or selecting the subject with the revascularization procedure and (b) administering to the subject a therapeutically effective amount of an anti-IL-1β binding antibody or binding fragment thereof.

The present disclosure also provides methods of treating acute hypertension in a subject comprising (a) identifying, diagnosing or selecting the subject with acute hypertension and (b) administering to the subject a therapeutically effective amount of an anti-IL-1β binding antibody or binding fragment thereof and one or more antihypertensive agents. In some embodiments, the hypertension is manifested as a blood pressure of greater than or equal to 180/110 mm Hg. In some other embodiments, the hypertension is mild-to-moderate, with systolic blood pressure (SBP) of 140 to 180 mm Hg and/or diastolic blood pressure (DBP) of 90 to 110 mm Hg.

The present disclosure also provides methods of reducing in a subject with a history of recent myocardial infarction (MI), recent stroke, or established peripheral arterial disease, the rate of a combined endpoint of new ischemic stroke (fatal or not), new MI (fatal or not), and other vascular death, comprising administering to said subject a therapeutically effective amount of an anti-IL-1β binding antibody or binding fragment thereof. In some embodiments, the subject has acute coronary syndrome without ST segment elevation (e.g., unstable angina or non-Q-wave myocardial infarction). In some embodiments, the anti-IL-1β binding antibody or binding fragment thereof is administered initially within 12, 24, 48 or 72 hours of onset of the most recent episode of chest pain or symptoms consistent with ischemia. In some embodiments, the subject has either ECG changes compatible with new ischemia (e.g., without ST segment elevation) or elevated cardiac enzymes or troponin I or T to at least twice the upper limit of normal.

The present disclosure also provides methods of reducing atherothrombotic events in a subject with a history of recent myocardial infarction (MI), recent stroke, or established peripheral arterial disease, comprising administering to said subject a therapeutically effective amount of an anti-IL-1β binding antibody or binding fragment thereof. In some embodiments, the subject has acute coronary syndrome without ST segment elevation (e.g., unstable angina or non-Q-wave myocardial infarction). In some embodiments, the anti-IL-1β binding antibody or binding fragment thereof is administered initially within 72 hrs, or preferably 48 hours, or more preferably 24, 12, 6 or 3 hours of onset of the most recent episode of chest pain or symptoms consistent with ischemia. In some embodiments, the subject has either ECG changes compatible with new ischemia (e.g., without ST segment elevation) or elevated cardiac enzymes or troponin I or T to at least twice the upper limit of normal.

The present disclosure also provides methods of reducing in subjects with ST-segment elevation acute myocardial infarction, the rate of death from any cause and the rate of a combined endpoint of death, re-infarction or stroke, comprising administering to said subject a therapeutically effective amount of an anti-IL-1β binding antibody or binding fragment thereof. In some embodiments, the anti-IL-1β binding antibody or binding fragment thereof is administered initially within 72 hrs, or preferably 48 hours, or more preferably 24, 12, 6 or 3 hours of the subject presenting with symptoms of myocardial infarction.

In some embodiments of any of the methods described above, the subject is a patient with cardiovascular disease, including, for example, acute cardiovascular disease or chronic cardiovascular disease.

In some embodiments of any of the methods described above, administering said therapeutically effective amount of an anti-IL-1β binding antibody or binding fragment thereof is sufficient to achieve a decrease in CRP levels.

The present disclosure also provides uses of an anti-IL-1β binding antibody or binding fragment thereof which has a lower $IC_{50}$ than an IL-1β receptor antagonist in a human whole blood IL-1β inhibition assay that measures IL-1β induced production of IL-8, in the manufacture of a composition for use in the reduction, prevention or treatment of a cardiac event or a cardiovascular disease.

The disclosure also provides that a reduction of a cardiovascular event (e.g., delaying time to event, reducing likelihood or risk of event, preventing an event, reducing severity of event, reducing time to recovery) may be evaluated in subjects over a period of 2 or more years, 3 or more years, 4 or more years, or 5 or more years following the cardiovascular event and/or initial administration of the IL-1β binding antibody or binding fragment thereof.

In addition, the disclosure further provides that a therapeutically effective amount of anti-IL-1β binding antibody or binding fragment thereof may also be sufficient to achieve a decrease in C-reactive protein (CRP) levels. The reduction in CRP levels is readily measured using standard assays (e.g., high-sensitivity CRP, ultra-sensitive CRP). As provided by the methods disclosed herein, the decrease in C-reactive protein levels may, for example, be a decrease of ≥0.2, ≥0.4, ≥0.6, ≥0.8, ≥1.0, ≥1.4, ≥1.8, ≥2.2, ≥2.6, ≥3.0 mg/L from pre-treatment levels. Alternatively, the decrease in C-reactive protein levels may, for example, be a decrease of >20%, >30%, >40%, >50%, >60%, >70%, >80%, >90%, >95% from pre-treatment levels.

Alternatively, or in addition, subjects treated as disclosed herein may experience a measurable improvement in lipid profile (e.g., decrease in serum lipids, change in ratio of HDL and LDL). Such measurements of serum lipids and/or lipid profile may include, for example a decrease in cholesterol, a decrease in low-density lipoprotein cholesterol (LDL), a decrease in very-low-density lipoprotein cholesterol (VLDL), a decrease in triglycerides, a decrease in free fatty acids, a decrease in apolipoprotein B (Apo B), an increase in high-density lipoprotein cholesterol (HDL), maintaining the level of high-density lipoprotein cholesterol (HDL) compared to pre-treatment level, and/or an increase in apolipoprotein A (Apo A). Measurements may be using standard techniques known in the art. For example, a decrease in the level of cholesterol (e.g., total cholesterol) may be a decrease of at least 5%, 10%, 15%, 20%, 25%, 30%, 35%, 40%, 45%, 50%, 55%, 60%, or more from the pre-treatment level. A decrease in the level of low-density lipoprotein cholesterol may be a decrease of at least 5%, 10%, 15%, 20%, 25%, 30%, 35%, 40%, 45%, 50%, 55%, 60%, or more from the pre-treatment level. A decrease in the triglyceride level in the blood of the subject may be a decrease of at least 5%, 10%, 15%, 20%, 25%, 30%, 35%, 40%, 45%, 50%, 55%, 60%, 65%, 70%, or more from the pre-treatment level. A decrease in the level of free fatty acids may be a decrease of at least 5%, 10%, 15%, 20%, 25%, 30%, 35%, 40%, 45%, 50%, 55%, 60%, or more from the pre-treatment level. An increase in the level of high-density lipoprotein cholesterol may be an increase of at least 1%, 2%, 3%, 4%, 5%, 6%, 8%, 10%, 12%, 14%, 16%, or more from the pre-treatment level.

The aforementioned diagnoses and measurements may be made using standard medical practices known in the art and/or any of a variety of standard assays known in the art, such as for example assays published in Chernecky C C, Berger B J, eds. (2004). *Laboratory Tests and Diagnostic Procedures,* 4th ed. Philadelphia: Saunders; Fischbach F T, Dunning M B III, eds. (2004). *Manual of Laboratory and Diagnostic Tests,* 7th ed. Philadelphia: Lippincott Williams and Wilkins; Genest J, et al. (2003). Recommendations for the management of dyslipidemia and the prevention of cardiovascular disease: Summary of the 2003 update. *Canadian Medical Association Journal,* 169(9): 921-924. Also available online: http://www.cmaj.ca/cgi/content/full/169/9/921/DC1; *Handbook of Diagnostic Tests* (2003). 3rd ed. Philadelphia: Lippincott Williams and Wilkins; and Pagana K D, Pagana T J (2002). *Mosby's Manual of Diagnostic and Laboratory Tests,* 2nd ed. St. Louis: Mosby.

Dosing

Anti-IL-1β binding antibodies or binding fragments thereof for use in any and/or all of the aforementioned methods may be administered in one or more doses (e.g., initial dose and one or more subsequent doses). In some embodiments, the anti-IL-1β binding antibody or binding fragment thereof is administered in one or more doses of 10 mg/kg or less, 5 mg/kg or less, 3 mg/kg or less, or 2 mg/kg or less of antibody or fragment. In some embodiments, the anti-IL-1β binding antibody or binding fragment thereof is administered in one or more doses of 1 mg/kg or less, one or more doses of 0.5 mg/kg or less, one or more doses of 0.3 mg/kg or less, one or more doses of 0.1 mg/kg or less, or one or more doses of 0.03 mg/kg or less of antibody or fragment. In some of the aforementioned embodiments, the one or more doses are at least 0.01 mg/kg of anti-IL-1β binding antibody or binding fragment thereof. In some embodiments, the anti-IL-1β binding antibody or binding fragment thereof is administered in one or more doses of about 0.01 mg/kg to 1 mg/kg, about 0.03 mg/kg to 1 mg/kg, about 0.01 mg/kg to 0.3 mg/kg, or about 0.1 mg/kg to 0.3 mg/kg. In some embodiments, the anti-IL-1β binding antibody or binding fragment thereof is administered in one or more doses of about 0.001 mg/kg to 0.3 mg/kg, about 0.001 mg/kg to 0.1 mg/kg, about 0.001 mg/kg to 0.03 mg/kg or about 0.001 mg/kg to 0.01 mg/kg.

In other embodiments, the initial dose and one or more subsequent doses of anti-IL-1β binding antibody or binding fragment thereof are each from about 0.01 mg/kg to about 10 mg/kg of antibody, from about 0.05 to about 5 mg/kg of antibody, from about 0.05 mg/kg to about 3 mg/kg of antibody, from about 0.1 mg/kg to about 3 mg/kg of antibody, from about 0.1 mg/kg to about 1 mg/kg of antibody, from about 0.1 mg/kg to about 0.5 mg/kg of antibody, from about 0.3 mg/kg to about 5 mg/kg of antibody, from about 0.3 mg/kg to about 3 mg/kg of antibody, from about 0.3 mg/kg to about 1 mg/kg of antibody, from about 0.5 mg/kg to about 5 mg/kg of antibody, from about 0.5 mg/kg to about 3 mg/kg of antibody, from about 0.5 mg/kg to about 1 mg/kg of antibody, from about 1 mg/kg to about 5 mg/kg of antibody, or from about 1 mg/kg to about 3 mg/kg of antibody. In certain embodiments, two or more, three or more, four or more, five or more, six or more, seven or more, eight or more, nine or more, ten or more or eleven or more subsequent doses of the antibody are administered. The aforementioned dosage amounts refer to mg (antibody or fragment)/kg (weight of the individual to be treated).

Anti-IL-1β binding antibodies or binding fragment thereof for use in any and/or all of the aforementioned methods may be administered as a fixed dose, independent of a dose per subject weight ratio. In some embodiments, the anti-IL-1β binding antibody or binding fragment thereof is administered in one or more fixed doses of 1000 mg or less, 500 mg or less, or 250 mg or less of antibody or fragment. In some embodiments, the anti-IL-1β binding antibody or binding fragment thereof is administered in one or more fixed doses of 100 mg or less, 25 mg or less, or 10 mg or less of antibody or fragment. In some embodiments, the anti-IL-1β binding antibody or binding fragment thereof is administered in one or more doses of at least 0.5 mg of antibody or fragment. In some embodiments, the anti-IL-1β binding antibody or binding fragment thereof is administered in one or more doses of at least 1 mg of antibody or fragment. In some embodiments, the anti-IL-1β binding antibody or binding fragment thereof is administered in one or more doses of at least 10 mg of antibody or fragment. In some embodiments, the anti-IL-1β binding antibody or binding fragment thereof is administered in one or more doses of 1 mg to 100 mg of antibody or fragment.

In certain embodiments, the fixed dose of anti-IL-1β binding antibody or binding fragment thereof is from about 1 mg to about 10 mg, about 1 mg to about 25 mg, about 10 mg to about 25 mg, about 10 mg to about 50 mg, about 10 mg to about 100 mg, about 25 mg to about 50 mg, about 25 mg to about 100 mg, about 50 mg to about 100 mg, about 50 mg to about 150 mg, about 100 mg to about 150 mg, about 100 mg to about 200 mg, about 150 mg to about 200 mg, about 150 mg to about 250 mg, about 200 mg to about 250 mg, about 200 mg to about 300 mg, about 250 mg to about 300 mg, about 250 mg to about 500 mg, about 300 mg to about 400 mg, about 400 mg to about 500 mg, about 400 mg to about 600 mg, about 500 mg to about 750 mg, about 600 mg to about 750 mg, about 700 mg to about 800 mg, or about 750 mg to about 1000 mg. In other embodiments, the fixed dose anti-IL-1β binding antibody or binding fragment thereof is from about 1 mg to about 10 mg, about 1 mg to about 25 mg, about 10 mg to about 25 mg, about 10 mg to about 100 mg, about 25 mg to about 50 mg, about 50 mg to about 100 mg, about 100 mg to about 150 mg, about 150 mg to about 200 mg, or about 200 mg to about 250 mg.

In some embodiments of any and/or all of the aforementioned methods, the fixed dose of anti-IL-1β binding antibody or binding fragment thereof is administered using a pre-filled syringe or delivery device.

In some embodiments of any and/or all of the aforementioned methods, the anti-IL-1β binding antibody or binding fragment thereof is administered by subcutaneous, intravenous or intramuscular injection.

In some embodiments of any and/or all of the aforementioned methods, administration of an initial dose of anti-IL-1β binding antibody or binding fragment thereof is followed by the administration of one or more subsequent doses. In some embodiments, the initial dose and one or more subsequent doses are administered at an interval of about once every week to about once every 12 months. In some embodiments, the initial dose and one or more subsequent doses are administered at an interval of about once every two weeks to about once every 6 months. In some embodiments, the initial dose and one or more subsequent doses are administered at an interval of about once every month to about once every 6 months. In some embodiments, the initial dose and one or more subsequent doses are administered at an interval of about once every month to about once every 3 months. In some embodiments, the initial dose and one or more subsequent doses are administered at an interval of about once every 3 months to about once every 6 months.

The disclosure also provides dosing regimens for use in any and/or all of the aforementioned methods, wherein the dosing regimens comprise more than one dosing interval for administration of an IL-1β binding antibody or binding fragment thereof. In some embodiments, the dosage regimen comprises at least two (e.g., two, three, four, five, six) different dosing intervals for administration of the IL-1β antibody or fragment thereof. In some embodiments, the dosage regimen comprises two different dosing intervals for administration of the IL-1β antibody or fragment thereof. In some embodiments, the dosing regimen comprises two different dosing intervals for administration of the IL-1β binding antibody or binding fragment thereof, wherein a first dosing interval comprises administration of one or more doses of the IL-1β antibody or fragment thereof and a second dosing interval comprises administration of one or more doses of the IL-1β antibody or fragment thereof, and wherein the first dosing interval is shorter in time than the second dosing interval. For example, the first dosing interval may be days or weeks, and the second dosing interval may be months. In some embodiments, the first dosing interval is about 5 days to about 28 days, about 7 days to about 21 days, about 12 days to about 16 days, or about 14 days. In some embodiments, the second dosing interval is about 1 month to about 3 months, about 1 month to about 2 months, or about 1 month. In some embodiments, the first dosing interval is about 7 days and the second dosing interval is about 1 month.

In some embodiments, administration of an initial dose of anti-IL-1β binding antibody or binding fragment thereof is followed by administration of one or more subsequent doses, and wherein the dosing intervals between administration of the initial dose and a second dose, and the second dose and a third dose are about 7 days to about 21 days, and wherein the dosing intervals between administration of subsequent doses is about 1 month to about 3 months. In some embodiments, the dosing intervals between administration of the initial dose and a second dose, and the second dose and a third dose are about 12 to 16 days, and the dosing intervals between administration of subsequent doses is about 1 month to about 2 months. In some embodiments, the dosing intervals between administration of the initial dose and a second dose, and the second dose and a third dose are about 14 days, and the dosing intervals between administration of subsequent doses is about 1 month. In some embodiments of any and/or all of the aforementioned methods, the anti-IL-1β binding antibody or binding fragment thereof is administered to a subject such that the interval between doses is a time sufficient to maintain a plasma concentration of said antibody or antibody fragment in the subject at a level of at least about 0.1 ug/mL. In some embodiments, the anti-IL-1β binding antibody or binding fragment thereof is administered to a subject such that the interval between doses is a time sufficient to maintain a plasma concentration of said antibody or antibody fragment in the subject at a level of at least about 0.3 ug/mL. In some embodiments, the anti-IL-1β binding antibody or binding fragment thereof is administered to a subject such that the interval between doses is a time sufficient to maintain a plasma concentration of said antibody or antibody fragment in the subject at a level of at least about 1 ug/mL. In some embodiments, these plasma concentration values refer to values obtained for an individual that is treated with the antibody of fragment in accordance with the disclosure herein.

In some embodiments of any and/or all of the aforementioned methods, administration of an initial dose of the anti-IL-1β binding antibody or binding fragment thereof is followed by the administration of one or more subsequent doses, and wherein said one or more subsequent doses are in an amount that is approximately the same or less than the initial dose.

In some embodiments of any and/or all of the aforementioned methods, administration of an initial dose of the anti-IL-1β binding antibody or binding fragment thereof is followed by the administration of one or more subsequent doses, and wherein at least one of the subsequent doses is in an amount that is more than the initial dose.

In some embodiments of any and/or all of the aforementioned methods, the anti-IL-1β binding antibody or binding fragment thereof has a lower $IC_{50}$ than an IL-1β receptor antagonist in a human whole blood IL-1β inhibition assay that measures IL-1β induced production of IL-8. In some embodiments, the IL-1β receptor antagonist is anakinra.

In some embodiments of any and/or all of the aforementioned methods, an anti-IL-1β binding antibody or binding fragment is administered, wherein administration of an initial dose of the antibody or antibody fragment is followed by the administration of one or more subsequent doses, and wherein the plasma concentration of said antibody or antibody fragment in the human is permitted to decrease below a level of about 0.1 ug/mL for a period of time greater than about 1 week and less than about 6 months between administrations during a course of treatment with said initial dose and one or more subsequent doses. In some embodiments, the plasma concentration of said antibody or antibody fragment is permitted to decrease below a level of about 0.07 ug/mL, about 0.05 ug/mL, about 0.03 ug/mL or about 0.01 ug/mL for a period of time greater than about 1 week and less than about 5 months, about 4 months, about 3 months, about 2 months, about 1 month, about 3 weeks, or about 2 weeks between administrations. In some embodiments, the plasma concentration values refer to values obtained for an individual that is treated with the antibody of fragment in accordance with the disclosure herein.

Combinations

The disclosure also provides that pharmaceutical compositions comprising one or more other active agents may be administered in conjunction with (e.g., separately from) the IL-1β binding antibodies or fragments, and such administrations may be performed at the same point or different points in time, such as for example the same or different days. Administration of the other active agents may be according to standard medical practices known in the art (e.g., current standard of care), or the administration may be modified (e.g., longer intervals, smaller dosages, delayed initiation) when used in conjunction with administration of IL-1β binding antibodies or fragments, such as disclosed herein. The active agents set forth below are exemplary and not intended to be limiting. combinations can also include more than one additional agent, e.g., two or three additional agents.

Anti-IL-1β antibodies or fragments thereof administered to a subject in as disclosed herein may be administered in combination with treatment with at least one additional active agent, such as for example any of the active agents provided herein. In one embodiment, treatment with the at least one active agent is maintained. In another embodiment, treatment with the at least one active agent is reduced or discontinued (e.g., when the subject is stable), while treatment with the anti-IL-1β antibody or fragment is maintained at a constant dosing regimen. In another embodiment, treatment with the at least one active agent is reduced or discontinued (e.g., when the subject is stable), and treatment with the anti-IL-1β antibody or fragment is reduced (e.g., lower dose, less frequent dosing, shorter treatment regimen). In another embodiment, treatment with the at least one active agent is is reduced or discontinued (e.g., when the subject is stable), and treatment with the anti-IL-1β antibody or fragment is increased (e.g., higher dose, more frequent dosing, longer treatment regimen). In yet another embodiment, treatment with the at least one active agent is maintained and treatment with the anti-IL-1β antibody or fragment is reduced or discontinued (e.g., lower dose, less frequent dosing, shorter treatment regimen). In yet another embodiment, treatment with the at least one active agent and treatment with the anti-IL-1β antibody or fragment are reduced or discontinued (e.g., lower dose, less frequent dosing, shorter treatment regimen).

In some embodiments, any of the methods described above may further comprise administering at least one other pharmaceutical composition comprising an active agent other than an anti-IL-1β binding antibody or binding fragment thereof. In some embodiments, the active agent of said at least one other pharmaceutical composition is a cholesterol lowering agent. In some embodiments, the active agent of said at least one other pharmaceutical composition is a statin or an HMG-CoA reductase inhibitor (e.g., lovastatin, pravastatin, simvastatin, fluvastatin, atorvastatin, cerivastatin, mevastatin, pitavastatin, rosuvastatin or mixtures thereof or mixtures with Ezetimibe, niacin, Amlodipine Besylate). In some embodiments, the active agent of said at least one other pharmaceutical composition is a calcium channel blocker (e.g., amlodipine, diltiazem, nifedipine, nicardipine, verapamil) or a beta blocker (e.g., esmolol, metoprolol, nadolol, penbutolol). In some embodiments, the active agent of said at least one other pharmaceutical composition is an antihypertensive (e.g., labetalol, metoprolol, hydralazine, nitroglycerin, nicardipine, sodium nitroprusside, clevidipine), a diuretic (e.g., a thiazide diuretic, chlorthalidone, furosemide, hydrochlorothiazide, indapamide, metolazone, amiloride hydrochloride, spironolactone, triamterene) or aspirin. In some embodiments, the active agent of said at least one other pharmaceutical composition is an angiotensin-converting enzyme (ACE) inhibitor (e.g. ramipril, ramiprilat, captopril, lisinopril) or an angiotensin II receptor blocker (e.g., losartan, olmesartan, valsartan). In some embodiments, the active agent of said at least one other pharmaceutical composition is a vasodilator. In some embodiments, the active agent of said at least one other pharmaceutical composition is an anticoagulant (e.g., acenocoumarol, phenprocoumon, warfarin heparin, low molecular weight heparin) or inhibitor of platelet aggregation (e.g., clopidogrel, ticlopidine, cilostazol, dipyridamole, eptifibatide, aspirin, abciximab, eptifibatide, tirofiban). In some embodiments, the active agent of said at least one other pharmaceutical composition is a thrombolytic (e.g., streptokinase, urokinase, alteplase, reteplase, tenecteplase). In some embodiments, the active agent of said at least one other pharmaceutical composition is digitalis. In some embodiments, the active agent of said at least one other pharmaceutical composition is digoxin or nesiritide. In some embodiments, the active agent of said at least one other pharmaceutical composition is oxygen. In some embodiments, the active agent of said at least one other pharmaceutical composition is a thrombin inhibitor (e.g., hirudin, bivalirudin). In some embodiments, the active agent of said at least one other pharmaceutical composition is a nitrate (e.g., glyceryl trinitrate (GTN)/nitroglycerin, isosorbide dinitrate, isosorbide mononitrate). In some embodiments, the active agent of said at least one other pharmaceutical composition is an analgesic (e.g., morphine sulfate). In some embodiments, the active agent of said at least one other pharmaceutical composition is a renin inhibitor. In some embodiments, the active agent of said at least one other pharmaceutical composition is an endothelin A receptor inhibitor. In some embodiments, the active agent of said at least one other pharmaceutical composition is an aldosterone inhibitor.

In another embodiment, the use of the IL-1β antibodies or binding fragments is contemplated in the manufacture of a medicament for treating or preventing a disease or condition as disclosed herein (e.g., for the reduction, prevention or treatment of cardiovascular events and/or cardiovascular diseases). In any of the uses, the medicament can be coordinated with treatment using a second active agent.

In yet another aspect of the present disclosure, an article of manufacture is provided, comprising a container, a composition within the container comprising an anti-IL-1β antibody or fragment thereof, and a package insert containing instructions to administer the antibody or fragment to a subject (e.g., human) as disclosed herein (e.g., for the reduction, prevention or treatment of cardiovascular events and/or cardiovascular diseases). In one embodiment, the container further comprises a pharmaceutically suitable carrier, excipient or diluent. In a related embodiment, the composition within the container further comprises a second active agent.

Kits are also contemplated by the disclosure. In one embodiment, a kit comprises a therapeutically or prophylactically effective amount of an anti-IL-1β antibody or fragment thereof, packaged in a container, such as a vial or bottle, and further comprising a label attached to or packaged with the container, the label describing the contents of the container and providing indications and/or instructions regarding use of the contents of the container as disclosed herein (e.g., for the reduction, prevention or treatment of cardiovascular events and/or cardiovascular diseases). In one embodiment, the container further comprises a pharmaceutically suitable carrier, excipient or diluent. In a related embodiment, the container further contains a second active agent.

In one embodiment, the article of manufacture, kit or medicament is for the treatment or prevention of a disease or condition in a subject (e.g., human) as disclosed herein (e.g., for the reduction, prevention or treatment of cardiovascular events and/or cardiovascular diseases). In another embodiment, the instructions of a package insert of an article of manufacture or label of a kit comprise instructions for administration of the antibody or fragment according to any of the aforementioned dose amounts and/or dosing regimens. In yet another embodiment, the container of kit or article of manufacture is a pre-filled syringe.

EXAMPLES

The following examples are intended merely to further illustrate the practice of the present disclosure, but should not be construed as in any way limiting its scope. The disclosures of all patent and scientific literatures cited within are hereby expressly incorporated in their entirety by reference.

Example 1

Administration of an IL-1β Antibody to Human Subjects

IL-1β binding antibodies or binding fragments thereof may be administered to a subject for the aforementioned uses. Specifically, in one example, an IL-1β antibody designated AB7 (described above) was administered to human subjects to evaluate safety, pharmacokinetics, and in vivo biological activity. A double-blind, placebo controlled clinical study was performed in human subjects with Type 2 diabetes. Groups of subjects were given the antibody by either the intravenous (IV) or subcutaneous (SC) route, and either as a single doses or as multiple doses over a period of time.

The treatment groups and numbers of subjects for the study are shown in the following table for a single dose by the IV route of administration.

| IV Route | Antibody | | Placebo |
|---|---|---|---|
| Group | # Subjects | Dose | # Subjects |
| 1 | 5 | 0.01 mg/kg | 1 |
| 2 | 5 | 0.03 mg/kg | 1 |
| 3 | 5 | 0.1 mg/kg | 1 |
| 4 | 5 | 0.3 mg/kg | 1 |
| 5 | 5 | 1.0 mg/kg | 1 |
| 6 | 5 | 3.0 mg/kg | 1 |

Similarly, treatment groups and numbers of subjects are shown in the following table for single and multiple (3 times, biweekly) doses by the SC route of administration.

| SC Route | Antibody | | Placebo |
|---|---|---|---|
| Group | # Subjects | Dose | # Subjects |
| Single Dose | | | |
| 1 | 5 | 0.03 mg/kg | 1 |
| 2 | 5 | 0.1 mg/kg | 1 |
| 3 | 5 | 0.3 mg/kg | 1 |
| Multi Dose | | | |
| 4 | 5 | 0.03 mg/kg | 1 |
| 5 | 5 | 0.3 mg/kg | 1 |

On study Day 1, antibody or placebo was administered via constant rate IV infusion or SC injection (e.g., anterior abdomen, arm, thigh). Safety assessments, including the recording of adverse events, physical examinations, vital signs, and clinical laboratory tests (e.g., blood chemistry, hematology, urinalysis) were conducted using standard medical practices known in the art. Blood samples were collected pre-dose administration and at multiple time periods post-administration to assess various parameters, including C-reactive protein.

Alternatively or in addition, study groups also may be included to evaluate, for example, the administration of additional numbers of subsequent doses at the same or longer intervals (e.g., monthly interval), alternative dose amounts, and/or increased group sizes.

Example 2

Pharmacokinetics of an IL-1β Antibody in Human Subjects

Samples are obtained for pharmacokinetic analysis at days 0, 1, 2, 3, 4, 7, 9±1, 11±1, 14±1, 21±2, 28±2, 42±3, and 56±3. Interim analysis of pharmacokinetic data following IV administration of a single dose of antibody at the 0.01, 0.03, 0.1, 0.3, or 1.0 mg/kg dose levels showed serum concentration-time profiles with a terminal half-life of 22 days, clearance of 2.54 mL/day/kg and volume of distribution of the central compartment of 41.3 mL/kg, very similar to serum volume (FIG. 1).

Figure 2:
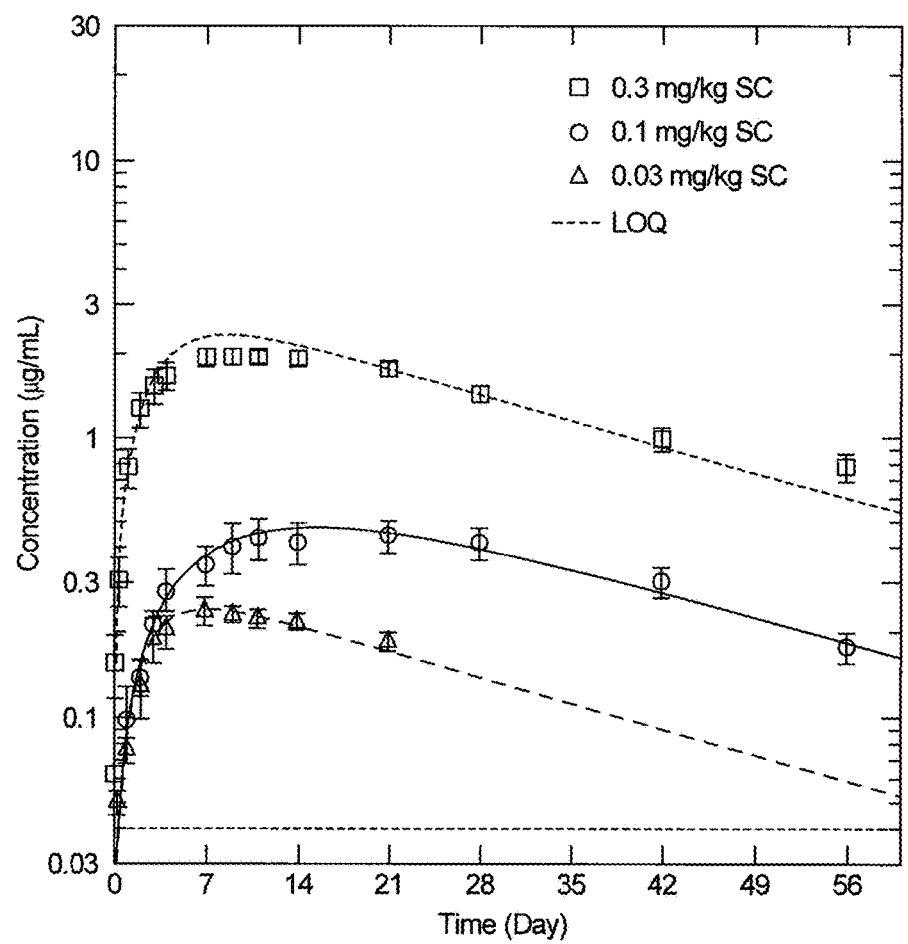
FIG. 2 is a graph showing serum concentrations following SC administration of 0.03, 0.1 and 0.3 mg/kg of an anti-IL-1β antibody in human subjects

Similarly, samples were analyzed for the single dose SC administration groups. As shown in FIG. 2, administration of the antibody at 0.03, 0.1 and 0.3 mg/kg dose levels yielded profiles with a terminal half-life of 22.7 days, clearance of 2.4 mL/day/kg and volume distribution of the central compartment of 40.7 mL/kg.

Example 3

Effect of an IL-1β Antibody on CRP in Human Subjects

Figure 3:
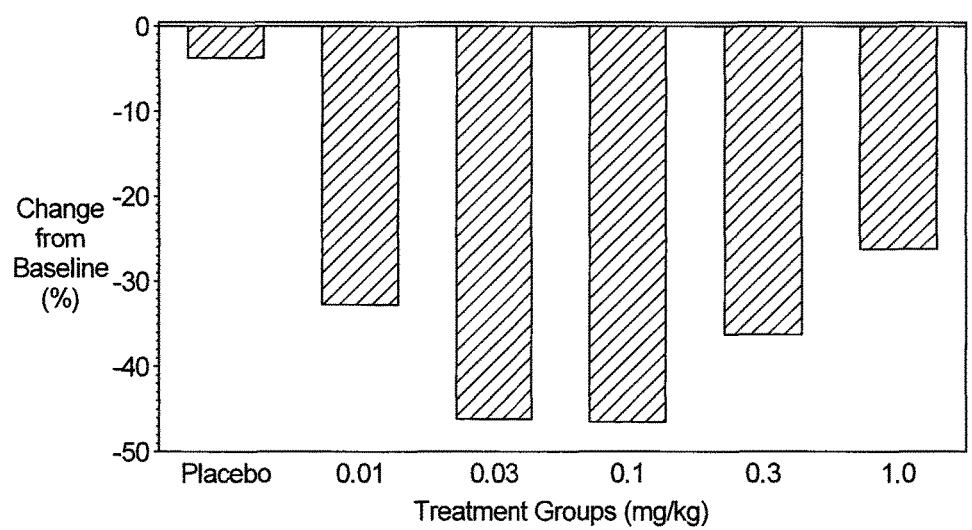
FIG. 3 is a graph showing median percent change in CRP at day 28 following administration of 0.01, 0.03, 0.1, 0.3, or 1.0 mg/kg of an anti-IL-1β antibody in human subjects.

C-reactive protein also was measured in serum at the same time points as the PK samples. A single dose of antibody reduced ultrasensitive C-reactive protein (usCRP) levels in each of the antibody treatment dose groups compared to placebo. As shown in FIG. 3, at 28 days after a single IV dose of antibody, the median percent reductions in usCRP were 33, 46, 47, 36, and 26 for the 0.01, 0.03, 0.1, 0.3, and 1.0 mg/kg dose groups, respectively, compared to 4 percent for placebo.

Example 4

Evaluation of an IL-1β Antibody in a Cardiovascular Event Model (Acute Myocardial Infarction)

To determine the cardioprotective effect (e.g., inhibiting adverse cardiac remodeling) of an IL-1β antibody or binding fragment thereof, a rodent model of acute myocardial infarction (MI) may be used (see for example, Wang et al., 2006, Tex. Heart Inst. J. 33:290-293; Salloum et al., 2009, Cardiovasc. Drugs Ther. 23:129-135). Improvements in measurements of heart function, such as for example in the MI model, are related to the chance of a subsequent cardiovascular event (e.g., congestive heart failure). Outbred mice (e.g., Institute of Cancer Research mice) and/or rats (e.g., Wistar rats) are used in the rodent MI model. Prior to surgery, the animals are evaluated by transthoracic echocardiography (TTE), for example, using a Vevo770 imaging system (VisualSonics, Toronto, Canada) or Acuson C256, to obtain measurements for the following parameters:

Left ventricular end-diastolic diameter (LVEDD)
Left ventricular end-systolic diameter (LVESD)
Anterior wall diastolic thickness (AWDT)
Posterior wall diastolic thickness (PWDT)
Anterior wall systolic thickness (AWST)
Posterior wall systolic thickness (PWST)
Left ventricular fractional-shortening (FS) is calculated as:

$$(LVEDD - LVESD)/LVEDD \times 100$$

Adult animals under anesthesia are subjected to coronary artery ligation. After thoracotomy to expose the heart, MI is induced by ligation of the proximal left descending coronary artery using a silk ligature placed around the vessel. Control animals (sham operation) are subjected to the same surgical procedure, but without the coronary ligation (see following table). Animals that die during or immediately after the postoperative period are not included in the analyses.

| | TTE | Surgery | Antibody Txt | Repeat TTE |
|---|---|---|---|---|
| Group 1 | Yes | Yes, MI induction | High dose (t = 0) | 24 hr, 7 d, 14 d |
| Group 2 | Yes | Yes, MI induction | Low dose (t = 0) | 24 hr, 7 d, 14 d |
| Group 3 | Yes | Yes, MI induction | High dose (24 hr) | 24 hr, 7 d, 14 d |

|  | TTE | Surgery | Antibody Txt | Repeat TTE |
|---|---|---|---|---|
| Group 4 | Yes | Yes, MI induction | Low dose (24 hr) | 24 hr, 7 d, 14 d |
| Group 3 | Yes | Yes, MI induction | Placebo | 24 hr, 7 d, 14 d |
| Group 4 | Yes | Yes, Sham operation | N/A | 24 hr, 7 d, 14 d |

Animals then receive either the treatment antibody or placebo (e.g., control antibody) administered intraperitoneally or intravenously at one or more pre-determined times during and/or following ischemia. For example, in one group the antibody is administered during ischemia (t=0) and in another group, the antibody is administered 24 hours after ischemia.

The animals are observed and numbers of deaths during the study period are recorded. The remaining animals again are evaluated by TTE at pre-determined post-treatment days (e.g., 24 hr, Day 7, Day 14). Systolic BP also may be measured in conscious awake awake, for example, using a noninvasive computerized tail-cuff system (BP-2000, Visitech Systems), which has been found to correlate closely with direct intraarterial measurement of BP. Animals are sacrificed, blood collected for serum, and the infarct area (size) determined. After removal, the heart is subjected to staining with Evans blue dye or 0.5% nitroblue tetrazolium (NBT), rinsed with saline and photographed to determine infarct size. The tissue is then fixed in 4% paraformaldehyde, embedded in paraffin and sectioned for staining with hematoxylin and eosin for histologic evaluation of tissue damage. Alternatively or additionally, tissue is fixed and sectioned to quantitate the level of cardiomyocyte cell death (e.g., TUNEL to determine apoptosis).

Alternatively, studies to evaluate the effect of an IL-1β antibody or fragment on heart function and/or adverse cardiac remodeling (e.g., chance of a subsequent cardiovascular event, such as for example, congestive heart failure) may be performed in adult male out-bred ICR mice (e.g., Harlan Laboratories (Indianapolis, Ind.)). CD-1 mice underwent experimental myocardial infarction as previously described (Abbate et al., 2008, Circulation 117:2670-2683). Mice were anesthetized with pentobarbital (70 mg/kg, IP), intubated orotracheally, and ventilated on a positive-pressure ventilator. Left thoracotomy was performed at the fourth intercostal space and the heart was exposed by stripping the pericardium. The left descending coronary artery was then identified with a surgical microscope (Leica F40) and ligated with a 7.0 silk ligature. A group of 4 mice underwent sham operation as previously described (Abbate, ibid). After surgery, mice were randomly assigned to treatment with the anti-IL-1β antibody XMA052 MG1K, administered intraperitoneally (0.05 mg/kg, 0.5 mg/kg, 5 mg/kg doses) or a control IgG (n=6 per group) immediately after surgery and then again 7 days later. The effect of pretreatment with an additional dose of the antibody (0.5 mg/kg) 48 hours prior to surgery also was tested.

All mice underwent transthoracic echocardiography before surgery and at 7, 14 and 28 days after coronary ligation. Doppler echocardiography was performed with the Vevo770 imaging system (VisualSonics Inc, Toronto, Ontario, Canada) and a 30-MHz probe. The heart was first imaged in the 2-dimensional mode in the parasternal and apical views and measurements were performed according to the to the American Society of Echocardiography recommendations (Gardin et al., 2002, J Am Soc Echocardiography 15:275-290). The left ventricular (LV) end-diastolic diameter (LVEDD), LV end-systolic diameters (LVESD), anterior wall diastolic thickness (AWDT), anterior wall systolic thickness (AWST), posterior wall diastolic thickness (PWDT), and posterior wall systolic thickness (PWST) were measured at M-mode. LV fractional shortening (LVFS) was calculated as follows: FS=(LVEDD−LVESD)/LVEDD×100. The number of akinetic segments (which correlates with infarct size) was determined using a 17-segment map. An apical view was used to measure the ejection time (ET), the time interval between the end of the transmitral A wave and the following E wave (AE). The myocardial performance index (MPI, or Tei index) was then computed (MPI=[AE-ET]/ET). The tricuspidal annular plane systolic excursion was also measured as a marker of right ventricular function. The investigator performing and reading the echocardiogram was blinded to the treatment allocation. The SPSS 11.0 (Chicago, Ill.) was used for the statistical analysis, using ANOVA for multiple comparisons with post-hoc T-test to explore between group differences. For comparisons of interval changes between multiple groups, random effects ANOVA for repeated-measures was used to determine the main effect of time, group, and time-by-group interaction. Statistical differences were considered significant if the P value was <0.05.

Figure 4:
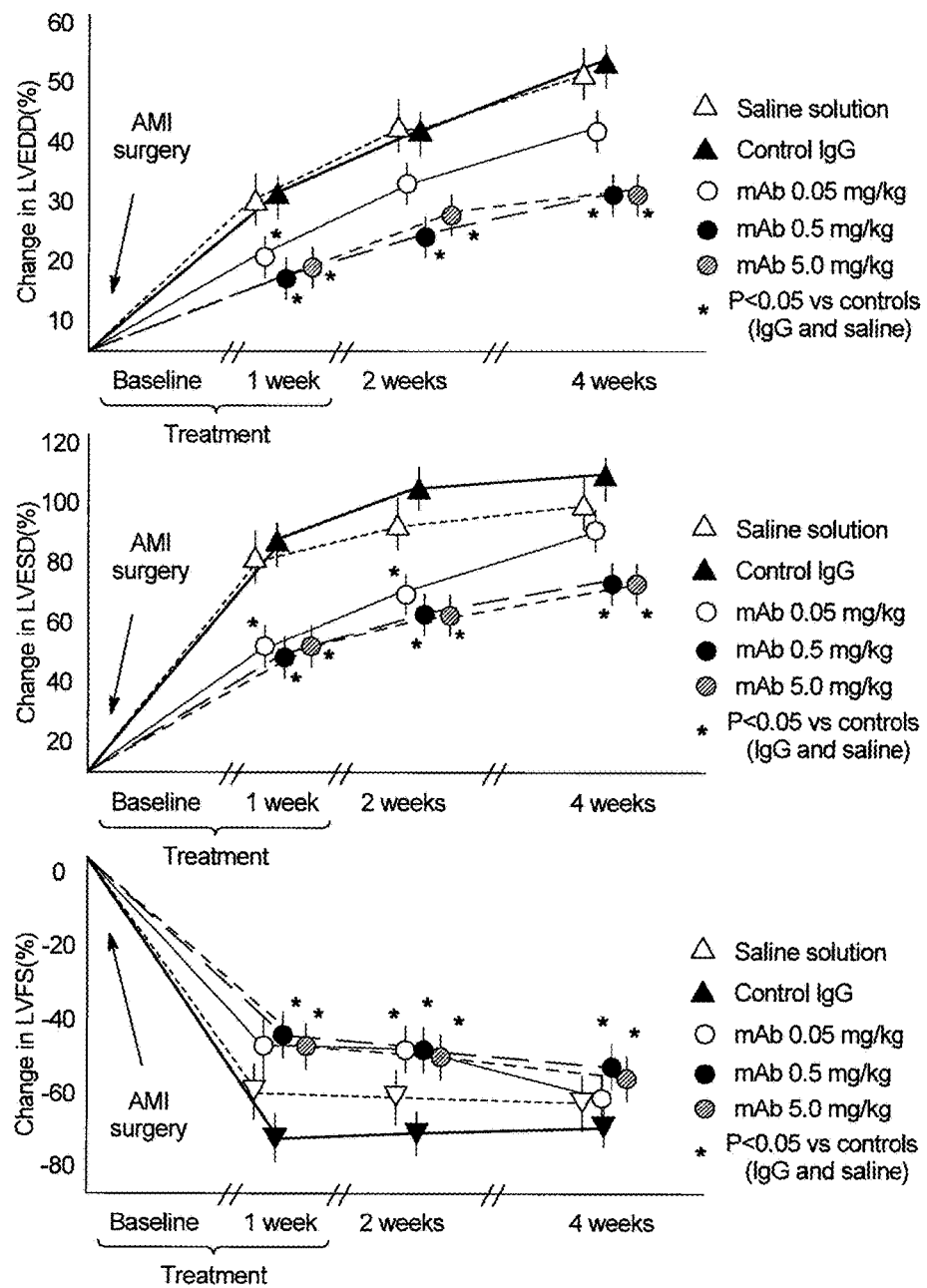
FIG. 4 is graphs showing changes in echocardiographic values in a myocardial infarction animal model.

Baseline echocardiographic values were similar in all groups. As expected, significant increases in LV diameters (LVEDD and LVESD) and a significant decrease in LVFS were observed as early as 7 days after surgery compared to baseline in all groups (except sham-operated mice). Mice receiving the XMA052 MG1K antibody had smaller increase in LVEDD, LVESD and smaller decrease in LVFS compared to controls (FIG. 4).

Figure 5:
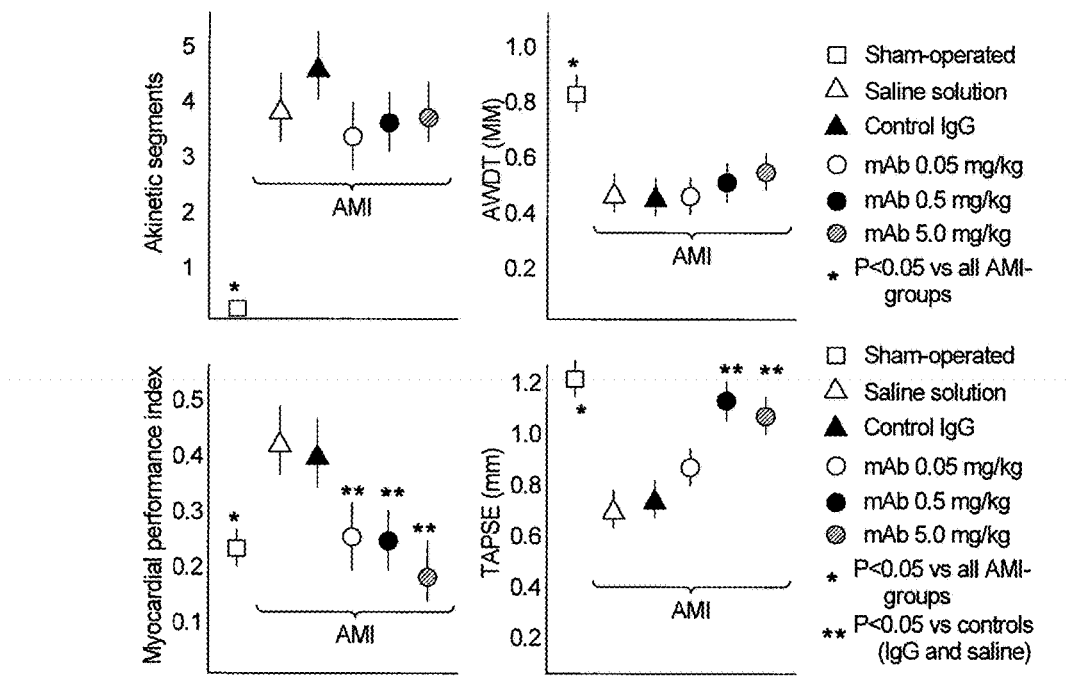
FIG. 5 is graphs showing measurements of akinetic segments (surrogate for infarct size), anterior wall (infarct) thickness, MPI or Tei index (marker of combined systolic and diastolic dysfunction and a surrogate marker for heart failure related mortality), and TAPSE (marker of right ventricular function and a surrogate marker for AMI related mortality in a myocardial infarction animal model.

The number of akinetic segments, a surrogate for infarct size, was 3.9±0.4 in the saline-treated mice, and it was not affected by treatment (FIG. 5). Accordingly, the anterior wall (infarct) thickness was 0.52±0.05 mm in the saline-treated and unaffected by treatment (FIG. 5). The MPI or Tei index, a marker of combined systolic and diastolic dysfunction and a surrogate marker for heart failure related mortality, was significantly increased after AMI (reflecting poor function) and preserved in the mice treated with the XMA052 MG1K antibody (FIG. 5). Similarly, the TAPSE, a marker of right ventricular function and a surrogate marker for AMI related mortality, was significantly decreased after AMI (reflecting poor function) and partially preserved in the mice treated with the XMA052 MG1K antibody (FIG. 5). Thus, blockade of IL-1β using the antibody ameliorates cardiac enlargement and dysfunction following AMI in the mouse, independent of infarct size. Pretreatment with an additional dose of the XMA052 MGIK antibody 48 hours prior to surgery offered no advantage over treatment after surgery in this animal model (data not shown).

Example 5

Evaluation of an IL-1β Antibody in a Cardiovascular Event Model (Stroke)

Rodent (e.g., mice, rats) models of stoke may be used to evaluate the effect of an IL-1β antibody or binding fragment thereof. For example, in one model, adult male Fischer rats are used (see for example, Morales et al., 2008, Circulation 118:1450-1459). In another model, C57BL/6 mice are used (see for example, Royl et al., 2009, Brain Res. 1265:148-157). Experiments are performed in a randomized fashion by investigators blinded to treatment groups. Permanent focal cerebral ischemia is induced by occlusion of the middle cerebral artery (MCAO), such as by cauterization or monofilament occlusion. Rats/mice in which the MCA was exposed but not occluded serve as sham-operated controls.

Control animal groups and MCAO groups then receive the treatment antibody or placebo (e.g., control antibody) administered intraperitoneally or intravenously at one or more pre-determined times following the procedure. For example, in one group the antibody is administered immediately following the procedure and in another group, the antibody is administered 24 hours later.

|  | MCAO | Antibody Txt | In-life Tests | MRI | Histology |
|---|---|---|---|---|---|
| Group 1 | Sham | N/A | Yes | Yes | Yes |
| Group 2 | Yes | Placebo | Yes | Yes | Yes |
| Group 3 | Yes | Low dose (t = 0) | Yes | Yes | Yes |
| Group 4 | Yes | High dose (t = 0) | Yes | Yes | Yes |
| Group 3 | Yes | Low dose (24 hr) | Yes | Yes | Yes |
| Group 4 | Yes | High dose (24 hr) | Yes | Yes | Yes |

Animals are evaluated for survival and body weight changes, as well as functional recovery (e.g., sensorimotor, behavioral testing, such as pole test, wire hanging test and/or neurological deficit score) and measurement of brain lesion size using MRI during the in-life stage (e.g., T2-weighted MRI), followed by histological examination (e.g., HE staining and GFAP staining of coronal brain cryostat sections) post-sacrifice (e.g., at 4 weeks). Additionally, a computer-assisted hemisphere volumetry may be performed, based on T2-weighted MRI and HE-stained coronal brain cryostat sections. Additional test groups may be evaluated to determine the effect on acute reperfusion after MCAO by measuring hemispheric cerebral blood flow with MRI (e.g., FAIR MRI).

Example 6

Evaluation of an IL-1β Antibody in a Model of Peripheral Vascular Disease

To determine the effect of an IL-1β antibody or binding fragment thereof on peripheral vascular disease, an animal model of limb ischemia may be used (see for example, Park et al., Endocrinology 149:483-491, 2008). For example, limb ischemia is induced in C57BL/6 male mice by the ligation of one femoral artery in anesthetized animals. Mice in which the artery is exposed but not ligated serve as sham-operated controls.

Control animal groups and artery ligation groups then receive the treatment antibody or placebo (e.g., control antibody) administered intraperitoneally or intravenously at one or more pre-determined times following the procedure. For example, in one group the antibody is administered immediately following the procedure and in another group, the antibody is administered 24 hours later.

|  | Ligation | Antibody Txt | LDPI | Histology |
|---|---|---|---|---|
| Group 1 | Sham | N/A | Yes | Yes |
| Group 2 | Yes | Placebo | Yes | Yes |
| Group 3 | Yes | Low dose (t = 0) | Yes | Yes |
| Group 4 | Yes | High dose (t = 0) | Yes | Yes |
| Group 3 | Yes | Low dose (24 hr) | Yes | Yes |
| Group 4 | Yes | High dose (24 hr) | Yes | Yes |

The blood flow in both hind legs is assessed with a laser Doppler perfusion image (LDPI) analyzer (Moor Instruments, Devon, UK), and the blood flow recovery is assessed by the ischemic limb to normal limb ratio of blood flow. Serial blood flow measurements by LDPI are observed at regular intervals (e.g., daily for two weeks). Mice are euthanized and the ischemic hind limb isolated for histological analysis.

After fixation with 4% paraformaldehyde, ischemic lower legs are embedded in OCT compound and frozen for cryostat sectioning. Tissue sections are stained with rat anti-mouse platelet EC adhesion molecule-1 (PECAM-1) (PharMingen), mouse anti-α smooth muscle actin (SMA) (Sigma), and rat anti-mouse CD45 (PharMingen), rabbit anti-cGKI (Calbiochem). To assess capillary density and inflammation, four random fields on two different sections (≈3 mm apart) from each mouse are photographed and by computer-assisted analysis, capillary density is calculated as the mean number of capillaries stained with PECAM-1 (endothelial marker) or α SMA (vascular smooth muscle marker). The mean number of infiltrating CD45-positive leukocytes is counted as the assessment of inflammation.

Example 7

Evaluation of an IL-1β Antibody in a Model of Atherosclerosis

Figure 6:
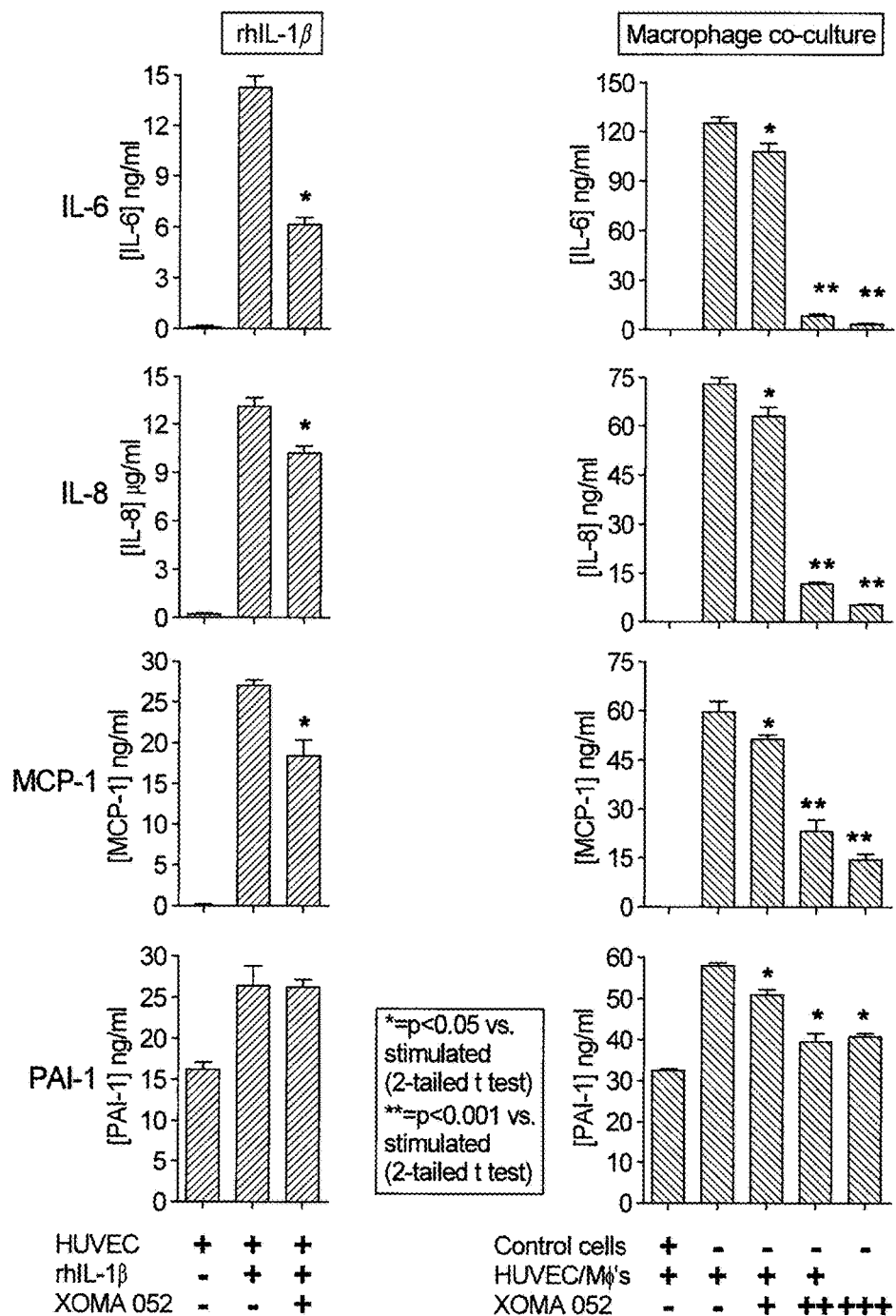
FIG. 6 is graphs showing inhibition of the release of macrophage-induced pro-inflammatory cytokines from endothelial cells.
Figure 7:
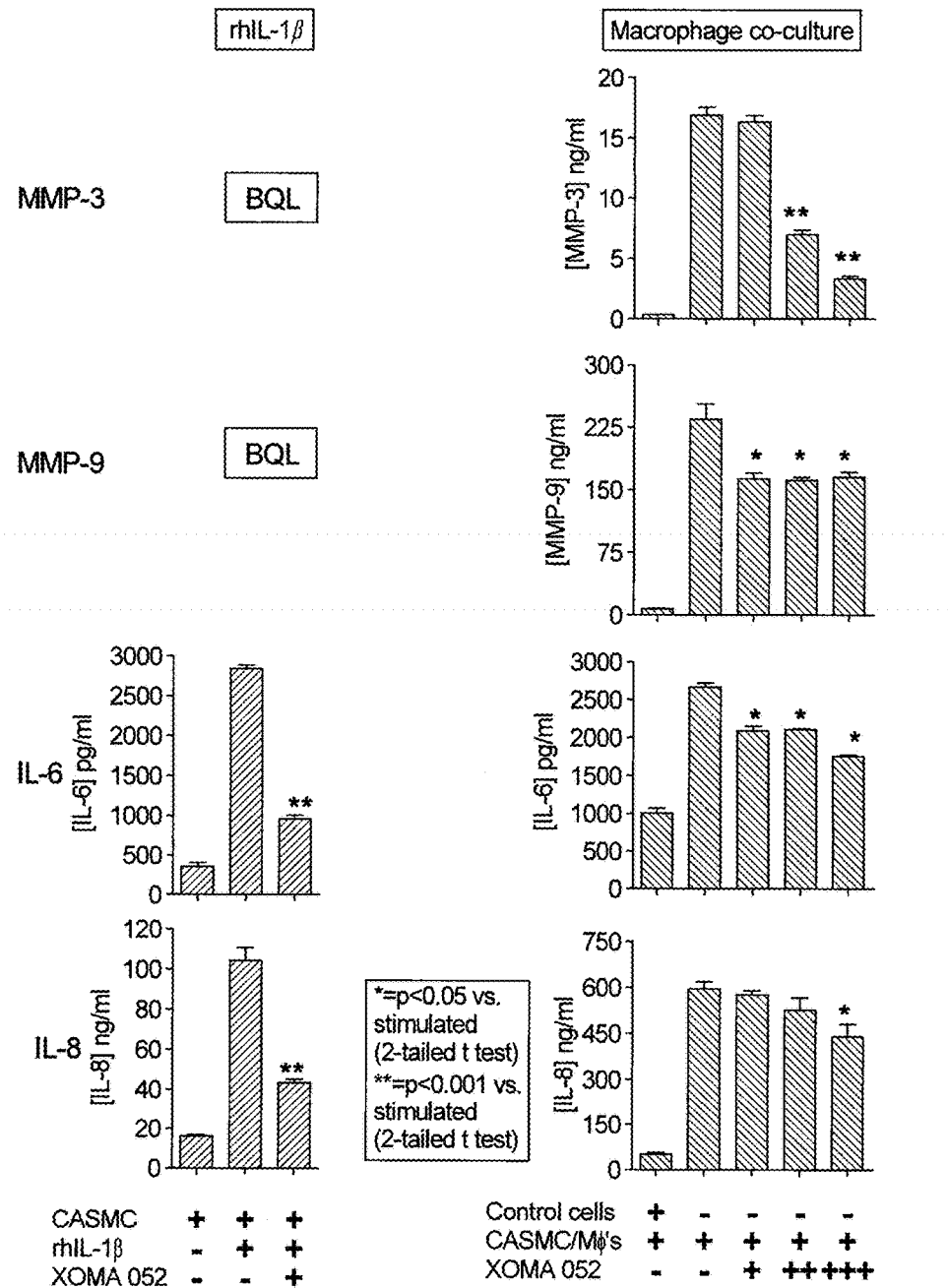
FIG. 7 is graphs showing inhibition of the release of macrophage-induced cytokines and degradative enzymes from smooth muscle cells.

The effect of an IL-1β antibody (XOMA 052) on macrophage-induced cytokine production from endothelial cells and smooth muscle cells was evaluated in a co-culture system. In this model, THP-1 cells were pre-activated to a macrophage-like phenotype with 200 nM PMA for 12 hours, washed once and added to pre-plated human umbilical vein endothelial cells (HUVEC) or human coronary artery smooth muscle cells (CASMC) at a ratio of (10:1; $10^6$ THP-1 and $10^5$ HUVEC or CASMC) in the presence or absence of XOMA 052, as indicated. Alternatively, cells were incubated with rhIL-1β (R&D Systems) in the presence or absence of XOMA 052, as indicated. After 48 hours, supernatants were removed and assessed for cytokine or enzyme content by ELISA (R&D Systems). All assays were performed in triplicate. The data demonstrate that XOMA 052 inhibits the release of IL-1β-induced pro-inflammatory molecules, such as IL-6, IL-8, MCP-1 and PAI-1 from endothelial cells (p<0.05, FIG. 6, left panel). In addition, the data show that XOMA 052 inhibits the release of IL-6 and IL-8 from smooth muscle cells, as well as IL-1β-driven MMP-3 and MMP-9 (p<0.05, FIG. 7, left panel). Importantly, it was also observed that XOMA 052 potently reduces the induction of these factors in the context of macrophage/EC or macrophage/SMC co-culture systems (p<0.05, FIGS. 6 & 7, right panel).

The ApoE knockout mouse is a well validated model of atherosclerosis that follows a similar pattern of progression to that of human. Male ApoE$^{-/-}$ mice on a C57BL/6 background were fed an atherogenic diet for 16 weeks beginning at 6 weeks and treated with an IL-1β antibody, XMA052 MG1K (i.p., twice weekly as indicated), control mouse IgG (i.p., twice weekly, 1.0 mg/kg; Jackson ImmunoResearch), or quinapril (subQ, 10 mg/kg, daily) for the duration of the study. En face analysis was carried out using Sudan IV staining as described previously (Calkin et al., 2007, Atherosclerosis 195:17-22) and as follows. Aortas were divided into arch, thoracic and abdominal aorta then cut longitudinally. After pinning en face onto wax, aortas were photographed and analyzed. Total and segmental plaque area was quantified as percentage area visualized red as stained by Sudan IV. Aortas were subsequently embedded in paraffin and sections cut for cross-sectional analysis. XMA052

Figure 8:
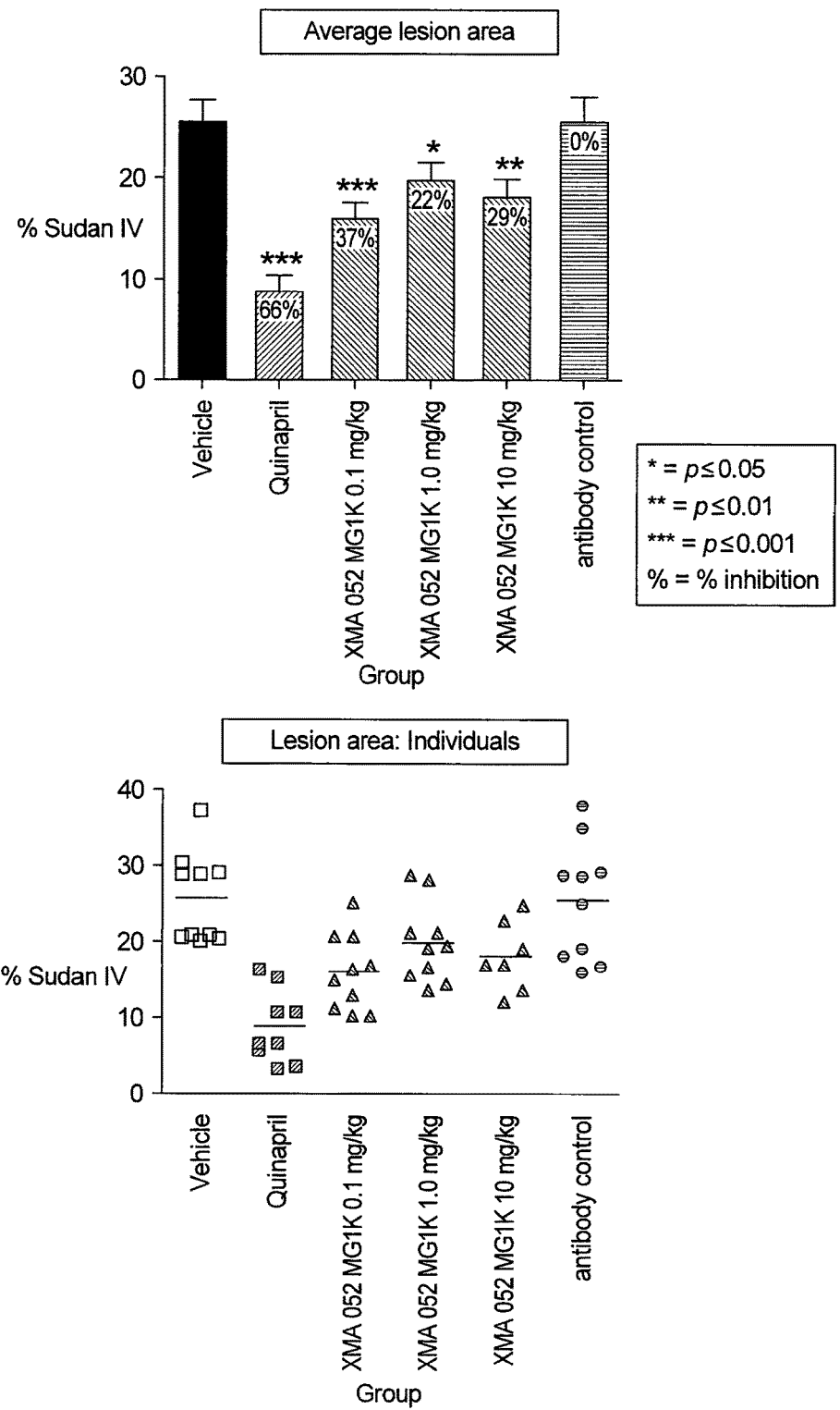
FIG. 8 is graphs showing reduction in the formation of atherosclerotic lesions in the aortas of ApoE knockout mice.

MG1K inhibited the formation of atherosclerotic lesions in ApoE knockout mice by 22-37% across the three doses tested (p<0.05, FIG. 8, 9).

Alternatively, plaque progression and in vivo coronary artery function is assessed using noninvasive high-resolution ultrasound techniques (see for example, Gronros et al., Am J Physiol Heart Circ Physiol. 295:H2046-53, 2008). Eight-week-old male ApoE mice are fed a high-fat diet with or without antibody treatment for approximately 16 weeks. During the course of treatment, total cholesterol levels are measured, as well as the degree of retardation of lesion progression in the brachiocephalic artery, as visualized in vivo using an ultrasound biomicroscope. Histological analysis is also used to determine the reduction of brachiocephalic atherosclerosis. Coronary artery function also may be measured by volumetric flow, such as for example by simultaneous recording of Doppler velocity signals and left coronary artery morphology before and during adenosine infusion.

|         | Antibody Txt | Cholesterol | Ultrasound | Histology |
|---------|--------------|-------------|------------|-----------|
| Group 1 | Placebo      | Yes         | Yes        | Yes       |
| Group 2 | Low dose     | Yes         | Yes        | Yes       |
| Group 3 | Med dose     | Yes         | Yes        | Yes       |
| Group 4 | High dose    | Yes         | Yes        | Yes       |

To further characterize the impact of IL-1β antibody on the formation of atherosclerotic lesions in the ApoE-knockout model, the aortic sinus and/or brachiocephalic artery is sectioned and assessed for lesion cross-sectional area and content (Zhou et al., 2008, Eur. J. Pharmacol. 590:297-302; Calkin et al., 2007, Atherosclerosis 195:17-22; Kirii et al., 2003, Arterioscler. Thromb. Vasc. Biol. 23:656-660). Serial 3-μm paraffin sections are dewaxed and rehydrated. Endogenous peroxidase activity is inhibited by incubation with 3% hydrogen peroxide. After blocking sections with 20% (v/v) goat serum in phosphate-buffered saline, sections are incubated overnight at 4° C. with antibodies against α-smooth muscle actin, inflammatory markers, such as IL-6, IL-8, MCP-1, ICAM-1 and VCAM-1, degradative enzymes, such as MMP-3, MMP-9 and cathepsin S or thrombotic factors, such as tissue factor or PAI-1. Sections are then incubated with the appropriate secondary antibodies. Positive areas are counted and expressed as a percentage of the whole plaque area. A negative control, in which the primary antibody is replaced with either mouse or rat IgG at the same dilution, is included. Sections are also evaluated for lipid content by staining with the lipophilic dye Oil Red O and macrophage infiltration is quantified by immunohistochemistry by staining with antibodies against CD68 (Kirii et al., 2003, Arterioscler. Thromb. Vasc. Biol. 23:656-660). Blinded analysis of positive immunostained sections is performed with an image-analysis program (Image Pro Plus, Media Cybernetics).

Alternatively, markers of inflammation and matrix degradation are interrogated by quantitative gene expression analysis (Calkin et al., 2007, Atherosclerosis 195:17-22). RNA is extracted from whole aorta by homogenization using Trizol and DNAse treated. Quantitative real time RT-PCR is carried out using the Taqman system on an ABI Prism 7700 Sequence Detector. Gene expression of the aforementioned genes are normalized to 18S mRNA and reported as ratios compared to the level of expression in untreated control mice. For statistical purposes, non-parametric data are handled as their log derivative. Differences in expression are compared using Student's t-tests (two groups) or one-way ANOVA (three or more groups).

The influence of IL-1β antibody on the aforementioned markers of inflammation, degradation and thrombosis are also assessed in the serum of antibody-treated ApoE knockout mice by ELISA or using the Mesoscale Discovery (MSD) platform. Serum obtained by cardiac puncture at the time of sacrifice is analyzed for serum lipids as described (Warnick, 1986, Methods Enzymol. 129:101-23). All lipid assays are performed in triplicate determinations. An external control sample with known analyte concentration is run for each assay to assure accuracy. Free plasma glycerol concentrations is also determined and used to correct the triglyceride values.

To quantitatively evaluate stability of atherosclerotic lesions, sections of 5 μm thickness are selected and quantified. Sections are serially cut every 50 μm from the cardiac base cross-section until the ascending aorta appears. Approximately six serial 5-μm sections per mouse are used for morphometric and immunohistochemical analysis. Collagen and foam cells in plaques are stained with a modified Movat pentachrome stain. Stained sections are inspected for buried fibrous caps within the plaque, which are also counted. Morphometry is performed with a computerized image-analysis program (Image Pro Plus, Media Cybernetics). Plaque composition, including extracellular lipids, foam cells and collagen is determined as a percentage of plaque area. The plaque area is measured directly and subtracted from the area enclosed by the internal elastic lamina to derive the patent lumen area corrected by dividing internal elastic lamina surrounding area. The effect of IL-1β antibody on plaque stability is evaluated by calculating the vulnerability index ((foam cells+extracellular lipids)/(collagens+smooth muscle cells)) and the average number of buried fibrous caps.

Systolic and diastolic blood pressure are measured using a tail-cuff system and mean blood pressure calculated (Chamberlain et al., 2009, PLoS ONE 4(4): e5073). To ensure stress levels of mice are kept to a minimum, a single handler is used throughout the experiment and mice are subjected to one week of training (blood pressure and pulse readings are taken, but the data discarded) prior to starting analysis. Measurements are taken at the same time, daily to avoid normal daily variance in blood pressure. In addition, the blood pressure is taken on the same part of the tail every day. During analysis, 10 measurements are taken each day, and mean blood pressure and standard deviation calculated for each 'data day' and week (total of 50 readings per mouse per week, 10 per day). On each day, individual data points are rejected if the blood pressure is below 40 or above 210 mmHg, or if it is outside of 2 standard deviations from the mean. All data for a day is rejected if there were less than 4 valid readings. Data for a week is rejected if it does not have at least 3 valid days of measurements. One week of baseline readings on chow diet are taken for each mouse, prior to feeding of Western or WHC diets. Data are analyzed by global non-linear regression. This statistical test analyzes an entire family of data sets simultaneously sharing one or more parameters between data sets. For each shared parameter, global non-linear regression finds one best-fit value that applies to all the data sets. In this case, blood pressure is determined under control (chow fed) and treated (diet-fed) conditions, for different mouse genotypes, and global non-linear regression determines whether the difference between each blood pressure curve is convincing. The test does not compare individual time points, but instead treats the data globally to produce a single p value per comparison.

These studies are further extended to evaluate the effect of the IL-1β antibody or fragment thereof on plaque rupture in carotid artery lesions in the ApoE deficient murine atherosclerosis model (see for example, Nakamura et al., Atherosclerosis, 2009, Feb. 21 [Epub ahead of print]). ApoE-deficient 8-week-old mice (C57BL/6) are anesthetized and subjected to ligation of the left common carotid artery just proximal to its bifurcation. Four weeks after ligation, a polyethylene cuff is applied just proximal to the ligated site. Control groups are included in which the artery is exposed but not ligated, as well as ligated but not subjected to the polyethylene cuff.

Animals then receive the treatment antibody or placebo (e.g., control antibody) administered intraperitoneally or intravenously at one or more pre-determined times following the procedure. For example, in one group the antibody is administered 24 or 48 hours preceding cuff placement. In another group, the antibody is administered at the time of cuff placement.

|  | Ligation | Cuff | Antibody Txt | Histology |
|---|---|---|---|---|
| Group 1 | Sham | N/A | N/A | Yes |
| Group 2 | Yes | No | N/A | Yes |
| Group 3 | Yes | No | Placebo | Day 0 |
| Group 4 | Yes | Yes | Placebo | Day 4 |
| Group 5 | Yes | No | Low dose (−24 hr) | Day 0 |
| Group 6 | Yes | No | High dose (−24 hr) | Day 0 |
| Group 7 | Yes | Yes | Low dose (−24 hr) | Day 4 |
| Group 8 | Yes | Yes | High dose (−24 hr) | Day 4 |
| Group 9 | Yes | Yes | Low dose (Day 0) | Day 4 |
| Group 10 | Yes | Yes | High dose (Day 0) | Day 4 |

Just before cuff placement (Day 0) and 4 days after cuff placement, mice are perfused through the left cardiac ventricle with isotonic saline and 4% paraformaldehyde in 0.01 M phosphate buffer (pH 7.4) under physiological pressure. Carotid arteries are collected and processed for histological analysis. Cross-cryosections (6 μm) are prepared from the intracuff region of each carotid artery and stained with hematoxylin and eosin (H&E), and picrosirius red for collagen. The corresponding sections on separate slides are used for immunohistochemical staining with antibodies against neutrophils.

The proportions of intraplaque hemorrhage and disruption in the neointima accompanying the intramural thrombus are compared between the antibody and control groups. Histological classification of the plaque disruption at the intracuff region of the carotid artery is done by dividing the lesions into three groups, based on the analyses of 30 sections at 60-μm intervals in each sample tissue. When there are no cracks and no mural or occlusive thrombus at the intracuff region, classification is "no disruption". When intraplaque hemorrhage, or mural or occlusive thrombus with cracks or erosion in the plaques are detected, classified is "hemorrhage" or "disruption", respectively.

Neutrophil infiltration in the neointima and collagen content is also determined. Collagen content is evaluated by the picrosirius red-stained positive area which appears bright when viewed with polarized light. Neutrophil infiltration in the intima is assessed by the neutrophils positive area which was stained by anti-neutrophil antibody (1:50; Serotec, MCA771GA).

Example 8

Cardiovascular Event Reduction in Subjects with a History of at Least One Risk Factor for Cardiovascular Disease To determine the effect of an IL-1β antibody or binding fragment thereof on reducing a cardiovascular event (e.g., time to first event) in subjects with a history of at least one risk factor for cardiovascular disease, a clinical study is performed. In one study, an IL-1β antibody is evaluated in an at risk population, measuring reduction of (e.g., preventing) a primary outcome that includes a composite of death from cardiovascular causes, myocardial infarction, or stroke, as well as each outcome separately. Measurements of reduction of (e.g., preventing) a secondary outcome may include death from any cause, the need for a revascularization procedure, heart failure, angina (e.g., hospitalization for angina, unstable angina), congestive heart failure, and acute coronary syndrome.

For a double-blind study, subjects are randomly enrolled into one of two IL-1β antibody treatment dose groups (e.g., 0.3 mg/kg, 0.1 mg/kg), or a matching placebo group. Antibody and placebo treatments are administered in conjunction with standard of care. Men and women of at least 55 years in age are included in the study if they have a history of coronary artery disease (e.g., manifest coronary artery disease), peripheral vascular disease, Type 2 diabetes, elevated total cholesterol, hypertension, low HDL cholesterol levels, tobacco smoking, atherosclerosis and/or microalbuminuria. Subjects are excluded if they are known to have experienced a recent (e.g., within 6 months of enrollment) cardiovascular event. Group sizes include sufficient numbers of subjects to detect a reduction in the relative risk of a cardiovascular event during the period of the study. All subjects provide written informed consent.

Subjects are administered the IL-1β antibody or placebo at monthly intervals and outcomes monitored throughout the study period (e.g., 3 year study period). Outcomes are determined by standard clinical diagnoses accepted by the medical field. Results indicative of an effect from the IL-1β antibody include a reduction in the relative risk of a cardiovascular event outcome (e.g., 20 percent reduction in relative risk).

Example 9

Cardiovascular Event Reduction in Subjects with a History a Previous Cardiovascular Event To determine the effect of an IL-1β antibody or binding fragment thereof on reducing a cardiovascular event (e.g., time to second event) in subjects with a history of a previous cardiovascular event, a clinical study is performed. In one study, an IL-1β antibody is evaluated in subjects in the period after the occurrence of a first documented cardiovascular event of myocardial infarction or acute coronary syndrome. The study measures reduction of (e.g., preventing) a primary cardiovascular event outcome that includes a composite of death from cardiovascular causes, myocardial infarction, or stroke, as well as each outcome separately. Measurements for reduction of (e.g., preventing) a secondary outcome may include death from any cause, the need for a revascularization procedure, heart failure, angina (e.g., hospitalization for angina, unstable angina), congestive heart failure, and acute coronary syndrome.

For a double-blind study, subjects are randomly enrolled into one of two dose groups (e.g., 0.3 mg/kg, 0.1 mg/kg) for an IL-1β antibody, or a matching placebo group. Men and women are enrolled in the study following a recent occurrence of a first cardiovascular event (e.g., within 96 hours), as described above. Group sizes include sufficient numbers of subjects to detect a reduction in the relative risk of a subsequent cardiovascular event during the period of the study. All subjects provide written informed consent.

Subjects are administered the IL-1β antibody or placebo at monthly intervals and outcomes monitored throughout the study period (e.g., 3 year study period). Outcomes are determined by standard clinical diagnoses accepted by the medical field. Results indicative of an effect from the IL-1β antibody include a reduction in the relative risk of a second cardiovascular event outcome (e.g., 20 percent reduction in relative risk).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element of the invention, it is specifically contemplated that a closed-ended term can be used in place of the open-ended term without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those working in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of reducing a cardiovascular event in a subject, comprising administering to said subject a therapeutically effective amount of an anti-IL-1β binding antibody or binding fragment thereof, wherein the subject is a subject with a history of a previous cardiovascular event wherein the cardiovascular event to be reduced is myocardial infarction, stroke, or cardiovascular death, and wherein the previous cardiovascular event is myocardial infarction.

2. The method of claim 1, wherein said subject also has a history of at least one risk factor for cardiovascular disease.

3. The method of claim 2, wherein the risk factor is manifest coronary heart disease, coronary artery disease, thrombosis, transient ischaemic attack, left ventricular hypertrophy, arteriosclerosis, restenosis, tobacco smoking or peripheral vascular disease.

4. The method of claim 2, wherein the risk factor is elevated triglycerides, systemic inflammation, high blood phosphorus levels, high parathyroid hormone levels, microalbuminuria, or high homocysteine levels.

5. The method of claim 2, wherein the risk factor is obesity, hyperglycemia, chronic renal failure, high blood glucose, chronic kidney disease, or metabolic syndrome.

6. The method of claim 2, wherein the risk factor is hypertension, dyslipidemia, hyperlipidemia, elevated total cholesterol, elevated LDL cholesterol, or low HDL cholesterol or atherosclerosis.

7. The method of claim 2, wherein the subject has a history of two or more said risk factors.

8. The method of claim 7, wherein the subject has a history of three or more said risk factors.

9. The method of claim 1, wherein the subject has elevated levels of C-reactive protein (CRP).

10. The method of claim 1, wherein the subject is older than 55 years.

11. The method of claim 1, wherein the subject is non-hypertensive.

12. The method of claim 1, wherein the subject has diabetes mellitus.

13. The method of claim 12, wherein said diabetes mellitus is Type 2 diabetes.

14. The method of claim 1, wherein administering said therapeutically effective amount of an anti-IL-1β binding antibody or binding fragment thereof is sufficient to achieve a decrease in CRP levels.

15. A method of reducing cardiovascular death in a subject wherein the subject has survived a previous cardiovascular event of myocardial infarction, comprising administering to said subject a therapeutically effective amount of an anti-IL-1β binding antibody or binding fragment thereof.

16. The method of claim 15, wherein the subject does not have Type 2 diabetes.

17. The method of claim 15, wherein the subject has a history of one or more risk factors for cardiovascular disease.

18. The method of claim 17, wherein the risk factor is manifest coronary heart disease, coronary artery disease, thrombosis, transient ischaemic attack, left ventricular hypertrophy, arteriosclerosis, restenosis, tobacco smoking or peripheral vascular disease.

19. The method of claim 17, wherein the risk factor is elevated triglycerides, systemic inflammation, high blood phosphorus levels, high parathyroid hormone levels, microalbuminuria, or high homocysteine levels.

20. The method of claim 17, wherein the risk factor is obesity, hyperglycemia, chronic renal failure, high blood glucose, chronic kidney disease, or metabolic syndrome.

21. The method of claim 17, wherein the risk factor is hypertension, dyslipidemia, hyperlipidemia, elevated total cholesterol, elevated LDL cholesterol, or low HDL cholesterol or atherosclerosis.

22. The method of claim 17, wherein the subject has a history of two or more said risk factors.

23. The method of claim 22, wherein the subject has a history of three or more said risk factors.

24. The method of claim 15, wherein the subject is non-hypertensive.

25. The method of claim 15, wherein administering said therapeutically effective amount of an anti-IL-1β binding antibody or binding fragment thereof is sufficient to achieve a decrease in CRP levels.

26. A method of reducing a cardiovascular event in a subject with a history of at least one risk factor for cardiovascular disease wherein the subject has survived a previous myocardial infarction, comprising administering to said subject a therapeutically effective amount of an anti-IL-1β binding antibody or binding fragment thereof, and wherein said risk factor is not Type 2 diabetes, obesity, hyperglycemia, dyslipidemia, hyperlipidemia, chronic renal failure, high blood glucose, chronic kidney disease, hypertension, atherosclerosis or metabolic syndrome.

27. The method of claim 26, wherein the risk factor is not Type 2 diabetes.

28. The method of claim 26, wherein the cardiovascular event is myocardial infarction.

29. The method of claim 26, wherein the cardiovascular event is stroke.

30. The method of claim 26, wherein the cardiovascular event is cardiovascular death.

31. The method of claim 26, wherein the risk factor is manifest coronary heart disease, coronary artery disease, thrombosis, transient ischaemic attack, left ventricular hypertrophy, arteriosclerosis, restenosis, tobacco smoking or peripheral vascular disease.

32. The method of claim 26, wherein the risk factor is elevated triglycerides, systemic inflammation, high blood phosphorus levels, high parathyroid hormone levels, microalbuminuria, or high homocysteine levels.

33. The method of claim 26, wherein the subject has elevated levels of C-reactive protein (CRP).

34. The method of claim 26, wherein the subject is older than 55 years.

35. The method of claim 26, wherein the subject has a history of two or more said risk factors.

36. The method of claim 35, wherein the subject has a history of three or more said risk factors.

37. The method of claim 26, wherein administering said therapeutically effective amount of an anti-IL-1β binding antibody or binding fragment thereof is sufficient to achieve a decrease in CRP levels.

38. A method of treating a cardiovascular event in a subject, wherein the cardiovascular event is myocardial infarction or stroke, and wherein the subject has survived a previous cardiovascular event of myocardial infarction, comprising administering to said subject a therapeutically effective amount of an anti-IL-1β binding antibody or binding fragment thereof and at least one other pharmaceutical composition comprising an active agent other than an IL-1β antibody or fragment.

39. The method of claim 38, wherein the active agent of said at least one other pharmaceutical composition is a cholesterol lowering agent, a statin, an HMG-CoA reductase inhibitor, a calcium channel blocker, a beta blocker, an antihypertensive, a diuretic, aspirin, niacin, an angiotensin-converting enzyme (ACE) inhibitor, an angiotensin II receptor blocker, a vasodilator, an anticoagulant, a inhibitor of platelet aggregation, a thrombolytic or digitalis.

40. A method for treating a cardiovascular event in a subject, wherein the cardiovascular event is myocardial infarction or stroke, and wherein the subject has survived a previous cardiovascular event of myocardial infarction, comprising administering to said subject a therapeutically effective amount of an anti-IL-1β binding antibody or binding fragment thereof and a revascularization procedure.

41. The method of claim 40, wherein the revascularization procedure is a coronary, carotid or peripheral arterial revascularization procedure.

42. The method of claim 38 or claim 40, wherein administering said therapeutically effective amount of an anti-IL-1β binding antibody or binding fragment thereof is sufficient to achieve a decrease in CRP levels.

43. The method of any one of claim 1, 15, 26, 38, or 40, further comprising administering at least one other pharmaceutical composition comprising an active agent other than an anti-IL-1β binding antibody or binding fragment thereof.

44. The method of any one of claim 1, 15, 26, 38, or 40, wherein the anti-IL-1β binding antibody or binding fragment thereof binds to human IL-1β with a dissociation constant of about 500 pM or less.

45. The method of any one of claim 1, 15, 26, 38, or 40, wherein the anti-IL-1β binding antibody or binding fragment thereof is administered in one or more doses of 1 mg/kg or less of antibody or fragment.

46. The method of any one of claim 1, 15, 26, 38, or 40, wherein the anti-IL-1β binding antibody or binding fragment thereof is administered as a fixed dose, independent of a dose per subject weight ratio.

47. The method of any one of claim 1, 15, 26, 38, or 40, wherein the anti-IL-1β binding antibody or binding fragment thereof is administered by subcutaneous, intravenous or intramuscular injection.

48. The method of any one of claim 1, 15, 26, 38, or 40, wherein administration of an initial dose of anti-IL-1β binding antibody or binding fragment thereof is followed by the administration of one or more subsequent doses.

* * * * *